US009527889B2

(12) United States Patent
Nichols et al.

(10) Patent No.: US 9,527,889 B2
(45) Date of Patent: Dec. 27, 2016

(54) RFAMIDE-RELATED PEPTIDES AND METHODS THEREOF

(71) Applicant: THE REGENTS OF THE UNIVERSITY OF MICHIGAN, Ann Arbor, MI (US)

(72) Inventors: Ruthann Nichols, Ann Arbor, MI (US); Margaret Westfall, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 14/582,553

(22) Filed: Dec. 24, 2014

(65) Prior Publication Data

US 2015/0183829 A1 Jul. 2, 2015

Related U.S. Application Data

(63) Continuation of application No. 13/638,946, filed as application No. PCT/US2011/030738 on Mar. 31, 2011, now abandoned.

(60) Provisional application No. 61/320,505, filed on Apr. 2, 2010.

(51) Int. Cl.

| C07K 5/04 | (2006.01) |
|---|---|
| C07K 5/10 | (2006.01) |
| C07K 7/06 | (2006.01) |
| C07K 7/08 | (2006.01) |
| A61K 38/07 | (2006.01) |
| A61K 38/08 | (2006.01) |
| A61K 38/10 | (2006.01) |
| G01N 33/68 | (2006.01) |
| G01N 33/94 | (2006.01) |
| C07K 5/08 | (2006.01) |
| C07K 5/107 | (2006.01) |
| C07K 5/117 | (2006.01) |
| G01N 33/50 | (2006.01) |
| C12Q 1/02 | (2006.01) |
| A61P 9/00 | (2006.01) |
| A61K 38/00 | (2006.01) |

(52) U.S. Cl.
CPC ............. *C07K 7/08* (2013.01); *A61K 38/07* (2013.01); *A61K 38/08* (2013.01); *A61K 38/10* (2013.01); *C07K 5/08* (2013.01); *C07K 5/1016* (2013.01); *C07K 5/1024* (2013.01); *C07K 7/06* (2013.01); *C12Q 1/025* (2013.01); *G01N 33/5008* (2013.01); *G01N 33/5061* (2013.01); *G01N 33/68* (2013.01); *G01N 33/9453* (2013.01); *A61K 38/00* (2013.01); *G01N 2500/10* (2013.01); *G01N 2800/32* (2013.01)

(58) Field of Classification Search
None
See application file for complete search history.

(56) References Cited

U.S. PATENT DOCUMENTS

| 7,192,723 B2 | 3/2007 | Watanabe et al. |
|---|---|---|
| 7,217,808 B2 | 5/2007 | Hinuma et al. |
| 7,354,724 B2 | 4/2008 | Lowery et al. |
| 7,683,031 B2 | 3/2010 | Ben-Sasson et al. |
| 2004/0132073 A1 | 7/2004 | Watanabe et al. |
| 2009/0062512 A1 | 3/2009 | Hildebrand et al. |

FOREIGN PATENT DOCUMENTS

| WO | WO-92/00995 A1 | 1/1992 |
|---|---|---|
| WO | WO-94/15958 A2 | 7/1994 |
| WO | WO-2004/026904 A1 | 4/2004 |
| WO | WO-2007/045906 A1 | 4/2007 |
| WO | WO-2009/043452 A1 | 4/2009 |

OTHER PUBLICATIONS

Angioy et al., Evidence dromyosuppressin acts at posterior and anterior pacemakers to decrease the fast and the slow cardiac activity in the blowfly Protophormia terraenovae. Peptides, 28: 585-93 (2007).
Barnard et al., Increases in arterial blood pressure in the rat in response to a new vertebrate neuropeptide, LPLRFamide, and a related molluscan peptide, FMRFamide. Regul. Pept. 8: 209-15 (1984).
Beck-Sickinger et al., Complete L-alanine scan of neuropeptide Y reveals ligands binding to Y1 and Y2 receptors with distinguished conformations. Eur. J. Biochem. 3: 947-58 (1994).
Boluyt et al., Echocardiographic assessment of age-associated changes in systolic and diastolic function of the female F344 rat heart. J. Appl. Physiol. 96: 822-8 (2004).
Braz et al., PKC-alpha regulates cardiac contractility and propensity toward heart failure. Nat. Med. 10: 248-54 (2004).
Brodde, Beta-adrenergic receptors in failing human myocardium. Basic Res. Cardiol. 91: 35-40 (1996).
Carpino et al., 9-Fluorenylmethoxycarbonyl amino-protecting group. J. Org. Chem. 37: 3404-9 (1972).
Dardente et al., RFamide-related peptide and its cognate receptor in the sheep: cDNA cloning, mRNA distribution in the hypothalamus and the effect of photoperiod. J. Neuroendocrinol. 20: 1252-9 (2008).
Dias et al., the effect of myosin regulatory light chain phosphorylation on the frequency-dependent regulation of cardiac function. J. Mol. Cell Cardiol. 41: 330-9 (2006).
DiMaio et al., Synthesis of chiral piperazin-2-ones as model peptidomimetics. J. Chem. Soc. Perkin Trans. 1687-9 (1989).
Dockray et al., A novel active pentapeptide from chicken brain identified by antibodies to FMRFamide. Nature, 305: 328-30 (1983).
Doherty et al., Structure-activity relationships of C-terminal endothelin hexapeptide antagonists. J. Med. Chem. 36: 2585-94 (1993).
EBI Accession No. AAR64934, Sequence 1 from U.S. Pat. No. 6,630,138, Neuropeptide Y analogue with amino acid substitution at position 32, dated Sep. 7, 1995.

(Continued)

*Primary Examiner* — Zachary Howard
(74) *Attorney, Agent, or Firm* — Marshall, Gerstein & Borun LLP

(57) ABSTRACT

Provided herein methods and compositions directed to RFRP-1 polypeptides for modulating cardiac contractile function, for preventing and/or treating cardiac disorders.

8 Claims, 19 Drawing Sheets

(56) References Cited

OTHER PUBLICATIONS

EBI Accession No. ABP97061, NADH dehydrogenase subunit 2, partial (mitochondrion) Otus rutilus, Rat RFRP-3 peptide, dated Jun. 23, 2003.
EBI Accession No. ADJ87486, Cytochrome oxidase subunit 1, partial (mitochondrion) [Lepidoptera sp. BOLD: AAA0243], Bovine RFRP SEQ ID No. 5, dated May 6, 2004.
EBI Accession No. ADJ87494, Cytochrome oxidase subunit 1, partial (mitochondrion) [Lepidoptera sp. BOLD:AAC5154], RFRP C-terminal peptide SEQ ID No. 13, dated May 6, 2004.
Fang et al., Cardiovascular effects of intravenous administered 26RFa, a novel RFamide peptide ligand for GPR103, in anaesthetised rats. Eur. J. Pharmacol. 621(1-3): 61-6 (2009).
Fukusumi et al., Characteristics and distribution of endogenous RFamide-related peptide-1. Biochim. Biophys. Acta. 1540: 221-32 (2001).
Fukusumi et al., Recent advances in mammalian RFamide peptides: the discovery and functional analyses of PrRP, RFRPs and QRFP. Peptides, 27: 1073-86 (2006).
Garvey et al., 3,4-Disubstituted γ-lactam rings as conformationally constrained mimics of peptide derivatives containing aspartic acid or norleucine. J. Org. Chem. 55: 936-40 (1990).
Gauspohl et al., Automated multiple peptide synthesis. Synthesis, 5: 315-20 (1992).
Gouarderes et al., Functional differences between NPFF1 and NPFF2 receptor coupling: high intrinsic activities of RFamide-related peptides on stimulation of [35S]GTPgammaS binding. Neuropharmacology, 2: 376-86 (2007).
Green et al., Calcitriol modulation of cardiac contractile performance via protein kinase C. J. Mol. Cell Cardiol. 41: 350-9 (2006).
Hinuma et al., New neuropeptides containing carboxy-terminal RFamide and their receptor in mammals., Nat. Cell Biol. 2: 703-8 (2000).
Holman et al., Primary structure and synthesis of a blocked myotropic neuropeptide isolated from the cockroach, Leucophaea maderae. Comp. Biochem. Physiol. C, 85: 219-24 (1986).
Jessup et al., Heart failure. N. Engl. J. Med. 348: 2007-18 (2003).
Jones et al., Amide bond isosteres: Imidazolines in pseudopeptide chemistry. Tetrahedron Lett. 29: 3853-6 (1988).
Kahn et al., The incorporation of β-turn prosthetic units into merrifield solid phase peptide synthesis. Tetrahedron Lett. 30: 2317-20 (1989).
Kazmierski et al., Topographic design of peptide neurotransmitters and hormones on stable backbone templates: relation of conformation and dynamics to bioactivity. J. Am. Chem. Soc. 113: 2275-83 (1991).
Kazmierski, Asymmetric synthesis of topographically constrained amino acids: synthesis of the optically pure isomers of α,β-dimethyl-phenylalanine and α,β-dimethyl-1,2,3,4-tetrahydroisoquinoline-3-carboxylic acid. Tetrahedron Lett. 32: 5769-72 (1991).
Kemp et al., (2S,5S,8S,11S)-1-Acetyl-1,4-diaza-3-keto-5-carboxy-10-thia-tricyclo -[2.8.04,8]-tridecane, 1 the preferred conformation of 1 (1 ≡ αTemp-OH) and its peptide conjugates αTemp-L-(Ala)n-OR (n=1 to 4) and α-Temp-L-Ala-L-Phe-L-Lys(εBoc)-L-Lys(ε-Boc)-NHMe studies of templates for α-helix formation. Tetrahedron Lett. 29: 4935-8 (1988).
Kemp et al., A convenient preparation of derivatives of 3(s)-amino-10(r)-carboxy-1,6-diaza-cyclodeca-2,7-dione the dilactam of L-α,γ-diaminobutyric acid and d-glutamic acid: A γ-turn template. Tetrahedron Lett. 29: 5057-60 (1988).
Kemp et al., Amino acid derivatives that stabilize secondary structures of polypeptides. 4. Practical synthesis of 4-(alkylamino)-3-cyano-6-azabicyclo[3.2.1]oct-3-enes (ben derivatives) as .gamma.-turn templates. J. Org. Chem. 54: 109-15 (1989).
Kemp et al., Conformational analysis of peptide-functionalized diacylaminoepindolidiones 1H NMR evidence for β-sheet formation. Tetrahedron Lett. 29: 5081-2 (1988).
Kemp et al., Conformationally restricted cyclic nonapeptides derived from L-cysteine and LL-3-amino-2-piperidone-6-carboxylic acid (LL-Acp), a potent .beta.-turn-inducing dipeptide analog. J. Org. Chem. 50: 5834-8 (1985).
Koch et al., The actions of RFamide neuroactive peptides on the isolated heart of the giant African snail, Achatina fulica. Compar. Biochem. Physiol. Part C, 106(2): 359-65 (1993).
Lin et al., Acute inhibition of Rho-kinase improves cardiac contractile function in streptozotocin-diabetic rats. Cardiovasc. Res. 75: 51-8 (2007).
Lingueglia et al., FMRFamide-gated sodium channel and ASIC channels: a new class of ionotropic receptors for FMRFamide and related peptides. Peptides, 27: 1138-52 (2006).
Liu et al., Identification and characterization of novel mammalian neuropeptide FF-like peptides that attenuate morphine-induced antinociception. J. Biol. Chem. 276: 36961-9 (2001).
Lymperopoulos et al., Adrenal adrenoceptors in heart failure: fine-tuning cardiac stimulation. Trends Mol. Med. 13: 503-11 (2007).
McCormick et al., Spatial and temporal expression identify dromyosuppressin as a brain-gut peptide in Drosophila melanogaster. J. Comp. Neurol. 338: 278-88 (1993).
Merrifield, Solid phase synthesis. Science, 232: 341-7 (1986).
Michele et al., Cardiac dysfunction in hypertrophic cardiomyopathy mutant tropomyosin mice is transgene-dependent, hypertrophy-independent, and improved by beta-blockade. Circ. Res. 91: 255-62 (2002).
Miyake et al., 1,2,3,4-tertrahydroisoquinoline-3-carboxylic acid angiotensin. J. Takeda Res. Labs, 43: 53-76 (1984). English Abstract Only.
Mollereau et al., Pharmacological characterization of human NPFF(1) and NPFF(2) receptors expressed in CHO cells by using NPY Y(1) receptor antagonists, Eur. J. Pharmacol., 451(3):245-256 (2002).
Mues et al., Blood pressure elevation in rats by peripheral administration of Tyr-Gly-Gly-Phe-Met-Arg-Phe and the invertebrate neuropeptide, Phe-Met-Arg-Phe-NH2. Life Sci. 31: 2555-61 (1982).
Nagai et al., Synthesis of a bicyclic dipeptide with the shape of β-turn central part. Tetrahedron Lett. 26: 647-50 (1985).
Neumann et al., Effects of adenosine analogues on contractile response and cyclic AMP content in guinea-pig isolated ventricular myocytes. Arch. Pharmacol., 340(6): 689-95 (1989).
Nichols et al., Differential processing of neuropeptides influences Drosophila heart rate. J. Neurogenet. 13: 89-104 (1999).
Nichols et al., Human RFamide-related peptide-1 diminishes cellular and integrated cardiac contractile performance. Peptides, 31(11): 2067-74 (2010).
Nichols et al., Structure-activity studies of RFamide-related peptide-1 identify a functional receptor antagonist and novel cardiac myocyte signaling pathway involved in contractile performance. J. Med. Chem., 55: 7736-45 (2012).
Nichols et al., Isolation and structural characterization of Drosophila TDVDHVFLRFamide and FMRFamide-containing neural peptides. J. Mol. Neurosci. 3: 213-8 (1992).
N-terminal Acetylation and C-terminal Amidation of Peptides, Thermo Electrical Corporation, 1-2 (2004).
Nichols, Signaling pathways and physiological functions of Drosophila melanogaster FMRFamide-related peptides. Annu. Rev. Entomol. 48: 485-503 (2003).
Noland et al., Identification of sites phosphorylated in bovine cardiac troponin I and troponin T by protein kinase C and comparative substrate activity of synthetic peptides containing the phosphorylation sites. J. Biol. Chem. 264: 20778-85 (1989).
Olson et al., Design and synthesis of a protein β-turn mimetic. J. Am. Chem. Soc. 112: 323-33 (1990).
Price et al., Structure of a molluscan cardioexcitatory neuropeptide. Science 197: 670-1 (1977).
Robb et al., Isolation, primary structure and bioactivity of schistoflrf-amide, a FMRF-amide-like neuropeptide from the locust, Schistocerca gregaria. Biochem. Biophys. Res. Commun. 160: 850-6 (1989).
Robb et al., The modulatory effect of SCHISTOFLRFamide on heart and skeletal muscle in the locust Schistocerca gregaria. J. Exp. Biol. 197: 437-42 (1994).

(56) References Cited

OTHER PUBLICATIONS

Roth et al., Elevation of arterial pressure in rats by two new vertebrate peptides FLF QPQRF-NH2 and AGEGLSSPFWSLAAPQRF-NH2 which are immunoreactive to FMRF-NH2 antiserum. *Neuopeptides*, 10(1): 37-42 (1987).

Shoelson et al., BpaB25 insulins. Photoactivatable analogues that quantitatively cross-link, radiolabel, and activate the insulin receptor. *J. Biol. Chem.* 268: 4085-91 (1993).

Stevens et al., The peptide hormone pQDLDHVFLRFamide (crustacean myosuppressin) modulates the Homarus americanus cardiac neuromuscular system at multiple sites. *J. Exp. Biol.* 212(Pt 24): 3961-76 (2009).

Thiemermann et al., FMRF-amind and L-Arg-L-Phe increase blood pressure and heart rate in the anaesthetised rat by central stimulation of the sympathetic nervous system. *Biochem. Biophys. Res. Commun.*, 175(1): 318-24 (1991).

Ubuka et al., Identification of human GnIH homologs, RFRP-1 and RFRP-3, and the cognate receptor, GPR147 in the human hypothalamic pituitary axis. *PLoS ONE*, 4(22): e8400 (2009).

Ukena, Distribution of novel RFamide-related peptide-like immunoreactivity in the mouse central nervous system. *Neurosci. Lett.* 300: 153-6 (2001).

Vahebi et al., Functional effects of rho-kinase-dependent phosphorylation of specific sites on cardiac troponin. *Circ. Res.* 96: 740-7 (2005).

Wasielewski et al., Pleiotropic effects of the neuropeptides CCAP and myosuppressin in the beetle, *Tenebrio molitor* L. *J. Comp. Physiol. B*, 178: 877-85 (2008).

Westfall et al., Adenovirus-mediated myofilament gene transfer into adult cardiac myocytes., *Meth. Cell Biol.*, 52: 307-22 (1997).

Westfall et al., Differential contribution of troponin I phosphorylation sites to the endothelin-modulated contractile response. *J. Biol. Chem.* 280: 41324-31 (2005).

Westfall et al., Role of troponin I phosphorylation in protein kinase C-mediated enhanced contractile performance of rat myocytes. *J. Biol. Chem.* 278: 33694-700 (2003).

Westfall, Myofilament protein phosphorylation by PKC in genetically engineered adult cardiac myocytes. *Methods Mol. Biol.* 219: 159-66 (2003).

Xiao et al., Ser-2030, but not Ser-2808, is the major phosphorylation site in cardiac ryanodine receptors responding to protein kinase A activation upon beta-adrenergic stimulation in normal and failing hearts. *Biochem J.* 396: 7-16 (2006).

Yano et al., Localization and neuronal response of RFamide related peptides in the rat central nervous system. *Brain Res.* 982: 156-67 (2003).

Zabrocki et al., Conformational mimicry. 1. 1,5-Disubstituted tetrazole ring as a surrogate for the cis amide bond. *J. Am. Chem. Soc.* 110: 5875-80 (1988).

Zechel et al., Synthetic glucagon antagonists and partial agonist. *Int. J. Pept. Protein Res.* 38: 131-8 (1991).

Zornik et al., Neural transmitters and a peptide modulate Drosophila heart rate. *Peptides* 20: 45-51 (1999).

International Search Report and Written Opinion of the International Searching Authority issued in connection with International Patent Application No. PCT/US2001/030738, European Patent Office, dated Jun. 21, 2011.

Extended European Search Report and Written Opinion issued in connection with European Patent Application No. 13168192.6, dated Mar. 24, 2014.

Echocardiography results in mouse in response to tail vein injections

|  | HR (bpm) | LVDs (mm$^2$) | SV (μl/beat) | EF% | CO (ml/mm) |
|---|---|---|---|---|---|
| Saline | -3% | -31% | +22% | +25% | +9% |
| 10$^{-8}$M hRFRP-1 | -64% | +36% | -75% | -60% | -91% |

SEQUENCE LISTING

```
<160> NUMBER OF SEQ ID NOS: 58

<210> SEQ ID NO 1
<211> LENGTH: 10
<212> TYPE: PRT
<213> ORGANISM: Drosophila melanogaster
<220> FEATURE:
<221> NAME/KEY: MOD_RES
<222> LOCATION: (10)..(10)
<223> OTHER INFORMATION: AMIDATION

<400> SEQUENCE: 1

Thr Asp Val Asp His Val Phe Leu Arg Phe
1               5                   10

<210> SEQ ID NO 2
<211> LENGTH: 12
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: AMIDATION

<400> SEQUENCE: 2

Met Pro His Ser Phe Ala Asn Leu Pro Leu Arg Phe
1               5                   10

<210> SEQ ID NO 3
<211> LENGTH: 5
<212> TYPE: PRT
```

```
<213> ORGANISM: Artificial Sequence
<220> FEATURE:
<223> OTHER INFORMATION: Synthetic peptide

<400> SEQUENCE: 3

Leu Pro Leu Arg Phe
1               5

<210> SEQ ID NO 4
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (11)..(11)
<223> OTHER INFORMATION: AMIDATION

<400> SEQUENCE: 4

Pro His Ser Phe Ala Asn Leu Pro Leu Arg Phe
1               5                   10

<210> SEQ ID NO 5
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa is any natural or modified amino acids
      other than L-Arg

<400> SEQUENCE: 5

Ala Pro Leu Xaa Phe
1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa is any natural or modified amino acids
      other than L-Arg

<400> SEQUENCE: 6

Ala Pro Gln Xaa Phe
1               5

<210> SEQ ID NO 7
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa is any natural or modified amino acids
      other than L-Arg

<400> SEQUENCE: 7

Ala Phe Leu Xaa Phe
1               5
```

```
<210> SEQ ID NO 8
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa is any natural or modified amino acids
      other than L-Arg

<400> SEQUENCE: 8

Ala Phe Gln Xaa Phe
1               5

<210> SEQ ID NO 9
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa is any natural or modified amino acids
      other than L-Arg

<400> SEQUENCE: 9

Val Pro Leu Xaa Phe
1               5

<210> SEQ ID NO 10
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa is any natural or modified amino acids
      other than L-Arg

<400> SEQUENCE: 10

Val Pro Gln Xaa Phe
1               5

<210> SEQ ID NO 11
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa is any natural or modified amino acids
      other than L-Arg

<400> SEQUENCE: 11

Val Phe Leu Xaa Phe
1               5

<210> SEQ ID NO 12
<211> LENGTH: 5
<212> TYPE: PRT
<213> ORGANISM: Artificial Sequence
<220> FEATURE:
```

```
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa is any natural or modified amino acids
      other than L-Arg

<400> SEQUENCE: 12

Val Phe Gln Xaa Phe
1               5

<210> SEQ ID NO 13
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is Met or is absent
<220> FEATURE:
<221> NAME/KEY: MISC_FEATURE
<222> LOCATION: (2)..(2)
<223> OTHER INFORMATION: Xaa is Pro or is absent
<220> FEATURE:
<221> NAME/KEY: MISC_FEATURE
<222> LOCATION: (3)..(3)
<223> OTHER INFORMATION: Xaa is His or is absent
<220> FEATURE:
<221> NAME/KEY: MISC_FEATURE
<222> LOCATION: (4)..(4)
<223> OTHER INFORMATION: Xaa is Ser or is absent
<220> FEATURE:
<221> NAME/KEY: MISC_FEATURE
<222> LOCATION: (5)..(5)
<223> OTHER INFORMATION: Xaa is Phe or is absent
<220> FEATURE:
<221> NAME/KEY: MISC_FEATURE
<222> LOCATION: (6)..(6)
<223> OTHER INFORMATION: Xaa is Ala or is absent
<220> FEATURE:
<221> NAME/KEY: MISC_FEATURE
<222> LOCATION: (7)..(7)
<223> OTHER INFORMATION: Xaa is Asn or is absent
<220> FEATURE:
<221> NAME/KEY: MISC_FEATURE
<222> LOCATION: (8)..(8)
<223> OTHER INFORMATION: Xaa is Leu or is absent
<220> FEATURE:
<221> NAME/KEY: MISC_FEATURE
<222> LOCATION: (9)..(9)
<223> OTHER INFORMATION: Xaa is Pro or is absent
<220> FEATURE:
<221> NAME/KEY: MISC_FEATURE
<222> LOCATION: (10)..(10)
<223> OTHER INFORMATION: Xaa is Leu or Gln or is absent
<220> FEATURE:
<221> NAME/KEY: MISC_FEATURE
<222> LOCATION: (11)..(11)
<223> OTHER INFORMATION: Xaa is Arg or is absent

<400> SEQUENCE: 13

Xaa Xaa Xaa Xaa Xaa Xaa Xaa Xaa Xaa Xaa Xaa Phe
1               5                   10

<210> SEQ ID NO 14
<211> LENGTH: 12
<212> TYPE: PRT
<213> ORGANISM: Bos primigenius
<220> FEATURE:
<221> NAME/KEY: MOD_RES
<222> LOCATION: (12)..(12)
<223> OTHER INFORMATION: AMIDATION
```

```
<400> SEQUENCE: 14

Met Pro Pro Ser Phe Ala Asn Leu Pro Leu Arg Phe
1               5                   10

<210> SEQ ID NO 15
<211> LENGTH: 12
<212> TYPE: PRT
<213> ORGANISM: Gallus gallus
<220> FEATURE:
<221> NAME/KEY: MOD_RES
<222> LOCATION: (12)..(12)
<223> OTHER INFORMATION: AMIDATION

<400> SEQUENCE: 15

Val Pro Asn Ser Val Ala Asn Leu Pro Leu Arg Phe
1               5                   10

<210> SEQ ID NO 16
<211> LENGTH: 12
<212> TYPE: PRT
<213> ORGANISM: Rattus norvegicus
<220> FEATURE:
<221> NAME/KEY: MOD_RES
<222> LOCATION: (12)..(12)
<223> OTHER INFORMATION: AMIDATION

<400> SEQUENCE: 16

Val Pro His Ser Ala Ala Asn Leu Pro Leu Arg Phe
1               5                   10

<210> SEQ ID NO 17
<211> LENGTH: 12
<212> TYPE: PRT
<213> ORGANISM: Ovis aries
<220> FEATURE:
<221> NAME/KEY: MOD_RES
<222> LOCATION: (12)..(12)
<223> OTHER INFORMATION: AMIDATION

<400> SEQUENCE: 17

Met Pro Pro Ser Ala Ala Asn Leu Pro Leu Arg Phe
1               5                   10

<210> SEQ ID NO 18
<211> LENGTH: 12
<212> TYPE: PRT
<213> ORGANISM: Rana magna
<220> FEATURE:
<221> NAME/KEY: MOD_RES
<222> LOCATION: (12)..(12)
<223> OTHER INFORMATION: AMIDATION

<400> SEQUENCE: 18

Ser Leu Lys Pro Ala Ala Asn Leu Pro Leu Arg Phe
1               5                   10

<210> SEQ ID NO 19
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (5)..(5)
<223> OTHER INFORMATION: AMIDATION

<400> SEQUENCE: 19
```

```
Ala Pro Leu Arg Phe
1               5

<210> SEQ ID NO 20
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (5)..(5)
<223> OTHER INFORMATION: AMIDATION

<400> SEQUENCE: 20

Ala Pro Gln Arg Phe
1               5

<210> SEQ ID NO 21
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (5)..(5)
<223> OTHER INFORMATION: AMIDATION

<400> SEQUENCE: 21

Ala Phe Leu Arg Phe
1               5

<210> SEQ ID NO 22
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (5)..(5)
<223> OTHER INFORMATION: AMIDATION

<400> SEQUENCE: 22

Ala Phe Gln Arg Phe
1               5

<210> SEQ ID NO 23
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (5)..(5)
<223> OTHER INFORMATION: AMIDATION

<400> SEQUENCE: 23

Val Pro Leu Arg Phe
1               5

<210> SEQ ID NO 24
<211> LENGTH: 5
<212> TYPE: PRT
<213> ORGANISM: Artificial Sequence
<220> FEATURE:
<223> OTHER INFORMATION: Synthetic peptide
<220> FEATURE:
```

```
<221> NAME/KEY: MOD_RES
<222> LOCATION: (5)..(5)
<223> OTHER INFORMATION: AMIDATION

<400> SEQUENCE: 24

Val Pro Gln Arg Phe
1               5

<210> SEQ ID NO 25
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (5)..(5)
<223> OTHER INFORMATION: AMIDATION

<400> SEQUENCE: 25

Val Phe Leu Arg Phe
1               5

<210> SEQ ID NO 26
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (5)..(5)
<223> OTHER INFORMATION: AMIDATION

<400> SEQUENCE: 26

Val Phe Gln Arg Phe
1               5

<210> SEQ ID NO 27
<211> LENGTH: 612
<212> TYPE: DNA
<213> ORGANISM: Mus musculus

<400> SEQUENCE: 27
atggaaatta tttcatcaaa gcgattcatt ttattgactt tagcaacttc aagcttctta      60
acttcaaaca cctttgttc agatgaatta atgatgcccc attttcacag caaagaaggt     120
tatggaaaat attaccagct gagaggaatc ccaaaagggg taaggaaag aagtgtcact     180 tttcaagaac tcaaagattg gggggcaaag aaagatatta agatgagtcc agcccctgcc     240
aacaaagtgc cccactcagc agccaacctt ccctgaggt ttgggaggaa catagaagac     300
agaagaagcc ccagggcacg ggccaacatg gaggcaggga ccatgagcca ttttcccagc     360
ctgccccaaa ggtttgggag aacaacagcc agacgcatca ccaagacact ggctggtttg     420
ccccagaaat ccctgcactc cctggcctcc agtgaattgc tctatgccat gacccgccag     480
catcaagaaa ttcagagtcc tggtcaagag caacctagga aacgggtgtt cacggaaaca     540
gatgatgcag aaaggaaaca agaaaaaata ggaaacctcc agccagtcct tcaagggggct     600 atgaagctgt ga                                                         612

<210> SEQ ID NO 28
<211> LENGTH: 203
<212> TYPE: PRT
<213> ORGANISM: Mus musculus
```

<400> SEQUENCE: 28

| | | | | | | | | | | | | | | |
|---|---|---|---|---|---|---|---|---|---|---|---|---|---|---|
|Met|Glu|Ile|Ile|Ser|Ser|Lys|Arg|Phe|Ile|Leu|Leu|Thr|Leu|Ala|Thr|
|1| | | |5| | | | |10| | | | |15|

Ser Ser Phe Leu Thr Ser Asn Thr Leu Cys Ser Asp Glu Leu Met Met
                20                  25                  30

Pro His Phe His Ser Lys Glu Gly Tyr Gly Lys Tyr Tyr Gln Leu Arg
            35                  40                  45

Gly Ile Pro Lys Gly Val Lys Glu Arg Ser Val Thr Phe Gln Glu Leu
        50                  55                  60

Lys Asp Trp Gly Ala Lys Lys Asp Ile Lys Met Ser Pro Ala Pro Ala
65                  70                  75                  80

Asn Lys Val Pro His Ser Ala Ala Asn Leu Pro Leu Arg Phe Gly Arg
                85                  90                  95

Asn Ile Glu Asp Arg Arg Ser Pro Arg Ala Arg Ala Asn Met Glu Ala
            100                 105                 110

Gly Thr Met Ser His Phe Pro Ser Leu Pro Gln Arg Phe Gly Arg Thr
        115                 120                 125

Thr Ala Arg Arg Ile Thr Lys Thr Leu Ala Gly Leu Pro Gln Lys Ser
130                 135                 140

Leu His Ser Leu Ala Ser Ser Glu Leu Leu Tyr Ala Met Thr Arg Gln
145                 150                 155                 160

His Gln Glu Ile Gln Ser Pro Gly Gln Glu Pro Arg Lys Arg Val
                165                 170                 175

Phe Thr Glu Thr Asp Asp Ala Glu Arg Lys Gln Glu Lys Ile Gly Asn
            180                 185                 190

Leu Gln Pro Val Leu Gln Gly Ala Met Lys Leu
        195                 200

<210> SEQ ID NO 29
<211> LENGTH: 1190
<212> TYPE: DNA
<213> ORGANISM: Homo sapiens

<400> SEQUENCE: 29
ataaacattg ggctgcacat agagacttaa ttttagattt agacaaaatg gaaattattt      60
catcaaaact attcatttta ttgactttag ccacttcaag cttgttaaca tcaaacattt     120
tttgtgcaga tgaattagtg atgtccaatc ttcacagcaa agaaaattat gacaaatatt     180
ctgagcctag aggataccca aaaggggaaa gaagcctcaa ttttgaggaa ttaaaagatt     240
ggggaccaaa aaatgttatt aagatgagta cacctgcagt caataaaatg ccacactcct     300
tcgccaactt gccattgaga tttgggagga cgttcaaga agaaagaagt gctggagcaa      360
cagccaacct gcctctgaga tctggaagaa atatggaggt gagcctcgtg agacgtgttc     420
ctaacctgcc ccaaaggttt gggagaacaa caacagccaa aagtgtctgc aggatgctga     480
gtgatttgtg tcaaggatcc atgcattcac catgtgccaa tgacttattt tactccatga     540
cctgccagca ccaagaaatc cagaatcccg atcaaaaaca gtcaaggaga ctgctattca     600
agaaaatagg tgatgcagaa ttgaaacaag aaaaataaga aacctggagc ctgtccctaa     660
agctgtggcc tgtaatctac aaatggctct atagcgaaga ccacacggaa gagtagctac     720
atacacttca tcagctatgg atcatcaacg gcaattttc cttgtcagta cagctataat       780
agtatcttga aagttgtaaa aaaattaaag catatttgtt acgtaaagtt aaaatgattt     840
ttgtctgaat aaaaaaaaag cattgcaaat gctttagaaa tctctgataa tggagagaga      900

```
gacagaggac cctcctcact accctatata aaaatcattg gcacagttac acttaataaa      960
aaaaattaaa cagaagagca ccctgaaaaa cattatgatg gaaattaaat agtatgccag     1020
aataacatgg ttgacaaata agtgaacaag gattaaaaat cacttacaaa cgtgtttctg     1080
tacacccttt ctatcgtgtc aaatgttaat gaatctgtga tcaattgaaa tgtaaatgtc     1140
tgtgtaaaac tacaaaataa aaactcttag actttaggga gaaagaaaa                1190

<210> SEQ ID NO 30
<211> LENGTH: 380
<212> TYPE: PRT
<213> ORGANISM: Homo sapiens

<400> SEQUENCE: 30

Lys His Trp Ala Ala His Arg Asp Leu Ile Leu Asp Leu Asp Lys Met
1               5                   10                  15

Glu Ile Ile Ser Ser Lys Leu Phe Ile Leu Leu Thr Leu Ala Thr Ser
            20                  25                  30

Ser Leu Leu Thr Ser Asn Ile Phe Cys Ala Asp Glu Leu Val Met Ser
        35                  40                  45

Asn Leu His Ser Lys Glu Asn Tyr Asp Lys Tyr Ser Glu Pro Arg Gly
    50                  55                  60

Tyr Pro Lys Gly Glu Arg Ser Leu Asn Phe Glu Leu Lys Asp Trp
65                  70                  75                  80

Gly Pro Lys Asn Val Ile Lys Met Ser Thr Pro Ala Val Asn Lys Met
                85                  90                  95

Pro His Ser Phe Ala Asn Leu Pro Leu Arg Phe Gly Arg Asn Val Gln
            100                 105                 110

Glu Glu Arg Ser Ala Gly Ala Thr Ala Asn Leu Pro Leu Arg Ser Gly
        115                 120                 125

Arg Asn Met Glu Val Ser Leu Val Arg Arg Val Pro Asn Leu Pro Gln
    130                 135                 140

Arg Phe Gly Arg Thr Thr Thr Ala Lys Ser Val Cys Arg Met Leu Ser
145                 150                 155                 160

Asp Leu Cys Gln Gly Ser Met His Ser Pro Cys Ala Asn Asp Leu Phe
                165                 170                 175

Tyr Ser Met Thr Cys Gln His Gln Glu Ile Gln Asn Pro Asp Gln Lys
            180                 185                 190

Gln Ser Arg Arg Leu Leu Phe Lys Ile Asp Asp Ala Glu Leu Lys
        195                 200                 205

Gln Glu Lys Glu Thr Trp Ser Leu Ser Leu Lys Leu Trp Pro Val Ile
    210                 215                 220

Tyr Lys Trp Leu Tyr Ser Glu Asp His Thr Glu Glu Leu His Thr Leu
225                 230                 235                 240

His Gln Leu Trp Ile Ile Asn Gly Asn Phe Ser Leu Ser Val Gln Leu
                245                 250                 255

Tyr Leu Glu Ser Cys Lys Lys Ile Lys Ala Tyr Leu Leu Arg Lys Val
            260                 265                 270

Lys Met Ile Phe Val Ile Lys Lys His Cys Lys Cys Phe Arg Asn
        275                 280                 285

Leu Trp Arg Glu Arg Gln Arg Thr Leu Leu Thr Thr Leu Tyr Lys Asn
    290                 295                 300

His Trp His Ser Tyr Thr Lys Lys Leu Asn Arg Arg Ala Pro Lys Thr
305                 310                 315                 320

Leu Trp Lys Leu Asn Ser Met Pro Glu His Gly Gln Ile Ser Glu Gln
```

```
                325                 330                 335
Gly Leu Lys Ile Thr Tyr Lys Arg Val Ser Val His Pro Phe Tyr Arg
            340                 345                 350
Val Lys Cys Ile Cys Asp Gln Leu Lys Cys Lys Cys Leu Cys Lys Thr
        355                 360                 365
Thr Lys Lys Leu Leu Asp Phe Arg Glu Lys Arg Lys
    370                 375                 380

<210> SEQ ID NO 31
<211> LENGTH: 19
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (19)..(19)
<223> OTHER INFORMATION: AMIDATION

<400> SEQUENCE: 31

Leu Ala Glu Glu Leu Ser Ser Tyr Ser Arg Arg Lys Gly Gly Phe Ser
1               5                   10                  15

Phe Arg Phe

<210> SEQ ID NO 32
<211> LENGTH: 8
<212> TYPE: PRT
<213> ORGANISM: Rattus norvegicus
<220> FEATURE:
<221> NAME/KEY: MOD_RES
<222> LOCATION: (8)..(8)
<223> OTHER INFORMATION: AMIDATION

<400> SEQUENCE: 32

Lys Gly Gly Phe Ser Phe Arg Phe
1               5

<210> SEQ ID NO 33
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (8)..(8)
<223> OTHER INFORMATION: AMIDATION

<400> SEQUENCE: 33

Val Asp His Val Phe Leu Arg Phe
1               5

<210> SEQ ID NO 34
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (10)..(10)
<223> OTHER INFORMATION: AMIDATION

<400> SEQUENCE: 34

Thr Asp Val Asp Ala Val Phe Leu Arg Phe
1               5                   10
```

```
<210> SEQ ID NO 35
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (10)..(10)
<223> OTHER INFORMATION: AMIDATION

<400> SEQUENCE: 35

Thr Asp Val Asp His Ala Phe Leu Arg Phe
1               5                   10

<210> SEQ ID NO 36
<211> LENGTH: 6
<212> TYPE: PRT
<213> ORGANISM: Artificial Sequence
<220> FEATURE:
<223> OTHER INFORMATION: Synthetic peptide

<400> SEQUENCE: 36

Thr Asp Val Asp His Val
1               5

<210> SEQ ID NO 37
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (3)..(3)
<223> OTHER INFORMATION: Xaa is Bpa

<400> SEQUENCE: 37

Tyr Thr Xaa Val Asp His Val Phe Leu Arg Phe
1               5                   10

<210> SEQ ID NO 38
<211> LENGTH: 12
<212> TYPE: PRT
<213> ORGANISM: Artificial Sequence
<220> FEATURE:
<223> OTHER INFORMATION: Synthetic peptide

<400> SEQUENCE: 38

Met Pro His Ser Phe Ala Asn Leu Pro Leu Arg Phe
1               5                   10

<210> SEQ ID NO 39
<211> LENGTH: 19
<212> TYPE: PRT
<213> ORGANISM: Rattus norvegicus
<220> FEATURE:
<221> NAME/KEY: MOD_RES
<222> LOCATION: (19)..(19)
<223> OTHER INFORMATION: AMIDATION

<400> SEQUENCE: 39

Leu Ala Glu Glu Leu Ser Ser Tyr Arg Arg Arg Lys Gly Gly Phe Ser
1               5                   10                  15

Phe Arg Phe

<210> SEQ ID NO 40
```

```
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (13)..(13)
<223> OTHER INFORMATION: AMIDATION

<400> SEQUENCE: 40

Tyr Met Pro His Ser Phe Ala Asn Leu Pro Leu Arg Phe
1               5                   10

<210> SEQ ID NO 41
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa is Bpa
<220> FEATURE:
<221> NAME/KEY: MOD_RES
<222> LOCATION: (12)..(12)
<223> OTHER INFORMATION: AMIDATION

<400> SEQUENCE: 41

Met Pro Xaa Ser Phe Ala Asn Leu Pro Leu Arg Phe
1               5                   10

<210> SEQ ID NO 42
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (12)..(12)
<223> OTHER INFORMATION: AMIDATION

<400> SEQUENCE: 42

Ala Pro His Ser Phe Ala Asn Leu Pro Leu Arg Phe
1               5                   10

<210> SEQ ID NO 43
<211> LENGTH: 12
<212> TYPE: PRT
<213> ORGANISM: Artificial Sequence
<220> FEATURE:
<223> OTHER INFORMATION: Synthetic peptide

<400> SEQUENCE: 43

Met Pro His Ser Phe Ala Ala Leu Pro Leu Arg Phe
1               5                   10

<210> SEQ ID NO 44
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (10)..(10)
<223> OTHER INFORMATION: AMIDATION

<400> SEQUENCE: 44
```

```
His Ser Phe Ala Asn Leu Pro Leu Arg Phe
1               5                   10

<210> SEQ ID NO 45
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (9)..(9)
<223> OTHER INFORMATION: AMIDATION

<400> SEQUENCE: 45

Ser Phe Ala Asn Leu Pro Leu Arg Phe
1               5

<210> SEQ ID NO 46
<211> LENGTH: 8
<212> TYPE: PRT
<213> ORGANISM: Artificial Sequence
<220> FEATURE:
<223> OTHER INFORMATION: Synthetic peptide

<400> SEQUENCE: 46

Phe Ala Asn Leu Pro Leu Arg Phe
1               5

<210> SEQ ID NO 47
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (7)..(7)
<223> OTHER INFORMATION: AMIDATION

<400> SEQUENCE: 47

Ala Asn Leu Pro Leu Arg Phe
1               5

<210> SEQ ID NO 48
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (6)..(6)
<223> OTHER INFORMATION: AMIDATION

<400> SEQUENCE: 48

Asn Leu Pro Leu Arg Phe
1               5

<210> SEQ ID NO 49
<211> LENGTH: 1254
<212> TYPE: DNA
<213> ORGANISM: Rattus norvegicus

<400> SEQUENCE: 49
atgggcaaga gatgggactc aaactcttca ggaagctggg atcacatctg gagtggcaat      60
gacacacagc atccttggta ttcagatatc aacatcacat acatgaacta ctatctccac     120
```

-continued

```
cagccccacg tgacagctgt cttcattagc tcctacttcc tgatcttctt cctgtgcatg      180
gtgggaaaca ctgtcgtttg ctttgttgta ataaggaata ggtacatgca cacggtcact      240
aatttcttca tcttcaacct cgcaataagt gacttactgg ttggaatatt ctgcatgcct      300
atcacattgc tggacaacat catagcagga tggccgtttg gaagcagcat gtgcaagatc      360
agcgggctgg tgcaagggat atcggttgcc gcttctgtct tcaccttggt tgccatagcc      420
gtagacagat tccggtgtgt ggtctacccc tttaagccca agctcactgt caagacagcc      480
tttgtcatga tcgtgatcat ctggggcctg gccatcacca ttatgacccc atctgcaatc      540
atgttacatg tacaggaaga aaaatactac cgtgtgaggc tcagctccca aataaaaacc      600
agcacagtct actggtgtcg ggaggattgg ccaaaccagg aaatgaggag atctacacc      660 accgtgctct tgccactat ctacctggct ccactctccc tcattgttat catgtatgca      720
aggattgggg cttccctctt caagacctca gcacacagca caggtaagca gcgcctggag      780
cagtggcatg tatccaagaa gaaacagaag gtcatcaaga tgctgctgac tgtggccctc      840 ctttcatcc tttcctggct tcccctgtgg actctgatga tgctctcaga ctatgctgac      900
ctgtcaccta acaaactacg tgtcatcaat atttatgtct acccttttgc ccactggctc      960
gccttctgca atagcagtgt caaccccatc atttatggtt tctttaatga aaatttcgc    1020 agtggtttcc aagatgcttt ccagttctgc caaaagaaag tcaaacccca ggaagcctat   1080
ggcctaagag ctaaacgcaa cctggacata aacacatctg gcctgttggt ccatgaacct   1140
gcatctcaaa acccaagtgg ggaaaacttg ggatgtagaa aaagtgcaga caatcccaca   1200
caggaatcct tgatggagga aacgggagaa gctaccaaca gtactgagac ttag         1254
```

<210> SEQ ID NO 50
<211> LENGTH: 417
<212> TYPE: PRT
<213> ORGANISM: Rattus norvegicus

<400> SEQUENCE: 50

```
Met Gly Lys Arg Trp Asp Ser Asn Ser Gly Ser Trp Asp His Ile
1               5                   10                  15

Trp Ser Gly Asn Asp Thr Gln His Pro Trp Tyr Ser Asp Ile Asn Ile
                20                  25                  30

Thr Tyr Met Asn Tyr Tyr Leu His Gln Pro His Val Thr Ala Val Phe
            35                  40                  45

Ile Ser Ser Tyr Phe Leu Ile Phe Phe Leu Cys Met Val Gly Asn Thr
        50                  55                  60

Val Val Cys Phe Val Val Ile Arg Asn Arg Tyr Met His Thr Val Thr
65                  70                  75                  80

Asn Phe Phe Ile Phe Asn Leu Ala Ile Ser Asp Leu Leu Val Gly Ile
                85                  90                  95

Phe Cys Met Pro Ile Thr Leu Leu Asp Asn Ile Ile Ala Gly Trp Pro
            100                 105                 110

Phe Gly Ser Ser Met Cys Lys Ile Ser Gly Leu Val Gln Gly Ile Ser
        115                 120                 125

Val Ala Ala Ser Val Phe Thr Leu Val Ala Ile Ala Val Asp Arg Phe
    130                 135                 140

Arg Cys Val Val Tyr Pro Phe Lys Pro Lys Leu Thr Val Lys Thr Ala
145                 150                 155                 160

Phe Val Met Ile Val Ile Trp Gly Leu Ala Ile Thr Ile Met Thr
                165                 170                 175
```

```
Pro Ser Ala Ile Met Leu His Val Gln Glu Lys Tyr Tyr Arg Val
            180                 185                 190
Arg Leu Ser Ser His Asn Lys Thr Ser Thr Val Tyr Trp Cys Arg Glu
        195                 200                 205
Asp Trp Pro Asn Gln Glu Met Arg Arg Ile Tyr Thr Thr Val Leu Phe
210                 215                 220
Ala Thr Ile Tyr Leu Ala Pro Leu Ser Leu Ile Val Ile Met Tyr Ala
225                 230                 235                 240
Arg Ile Gly Ala Ser Leu Phe Lys Thr Ser Ala His Ser Thr Gly Lys
                245                 250                 255
Gln Arg Leu Glu Gln Trp His Val Ser Lys Lys Lys Gln Lys Val Ile
            260                 265                 270
Lys Met Leu Leu Thr Val Ala Leu Leu Phe Ile Leu Ser Trp Leu Pro
        275                 280                 285
Leu Trp Thr Leu Met Met Leu Ser Asp Tyr Ala Asp Leu Ser Pro Asn
    290                 295                 300
Lys Leu Arg Val Ile Asn Ile Tyr Val Tyr Pro Phe Ala His Trp Leu
305                 310                 315                 320
Ala Phe Cys Asn Ser Ser Val Asn Pro Ile Ile Tyr Gly Phe Phe Asn
                325                 330                 335
Glu Asn Phe Arg Ser Gly Phe Gln Asp Ala Phe Gln Phe Cys Gln Lys
            340                 345                 350
Lys Val Lys Pro Gln Glu Ala Tyr Gly Leu Arg Ala Lys Arg Asn Leu
        355                 360                 365
Asp Ile Asn Thr Ser Gly Leu Leu Val His Glu Pro Ala Ser Gln Asn
    370                 375                 380
Pro Ser Gly Glu Asn Leu Gly Cys Arg Lys Ser Ala Asp Asn Pro Thr
385                 390                 395                 400
Gln Glu Ser Leu Met Glu Glu Thr Gly Glu Ala Thr Asn Ser Thr Glu
                405                 410                 415
Thr

<210> SEQ ID NO 51
<211> LENGTH: 1656
<212> TYPE: DNA
<213> ORGANISM: Homo sapiens

<400> SEQUENCE: 51
catcatgaat gagaaatggg acacaaactc ttcagaaaac tggcatccca tctggaatgt    60
caatgacaca aagcatcatc tgtactcaga tattaatatt acctatgtga actactatct   120
tcaccagcct caagtggcag caatcttcat tatttcctac tttctgatct tcttttttgtg  180
catgatggga atactgtggg tttgctttat tgtaatgagg aacaaacata tgcacacagt   240
cactaatctc ttcatcttaa acctggccat aagtgattta ctagttgcat attctgcat   300
gcctataaca ctgctggaca atattatagc aggatggcca tttggaaaca cgatgtgcaa   360
gatcagtgga ttggtccagg gaatatctgt cgcagcttca gtctttacgt tagttgcaat   420
tgctgtagat aggttccagt gtgtggtcta ccctttttaaa ccaaagctca ctatcaagac   480
agcgtttgtc attattatga tcatctgggt cctagccatc accattatgt ctccatctgc   540
agtaatgtta catgtgcaag aagaaaaata ttaccgagtg agactcaact cccagaataa   600
aaccagtcca gtctactggt gccgggaaga ctggccaaat caggaaatga ggaagatcta   660
caccactgtg ctgtttgcca acatctacct ggctcccctc tccctcattg tcatcatgta   720
```

```
tggaaggatt ggaatttcac tcttcagggc tgcagttcct cacacaggca ggaagaacca    780
ggagcagtgg cacgtggtgt ccaggaagaa gcagaagatc attaagatgc tcctgattgt    840
ggccctgctt tttattctct catggctgcc cctgtggact ctaatgatgc tctcagacta    900
cgctgacctt tctccaaatg aactgcagat catcaacatc tacatctacc cttttgcaca    960
ctggctggca ttcggcaaca gcagtgtcaa tcccatcatt tatggtttct caacgagaa    1020 tttccgccgt ggtttccaag aagctttcca gctccagctc tgccaaaaaa gagcaaagcc    1080
tatggaagct tatgccctaa aagctaaaag ccatgtgctc ataaacacat ctaatcagct    1140
tgtccaggaa tctacatttc aaaccctca tggggaaacc ttgctttata ggaaaagtgc     1200
tgaaaaaccc caacaggaat tagtgatgga agaattaaaa gaaactacta acagcagtga    1260
gatttaaaaa gagctagtgt gataatccta actctactac gcattatata tttaaatcca    1320 ttgcttttg tggctttgca cttcaaattt ttcaaagaat gttctaaata aacatttac     1380 tgaaagccct ctctggcaaa aaattaaaa ataaacaaaa atggtcataa gatcataaac     1440
aatcttatgt tgtataaaaa tacgtagagt gacttagaca tgtttgcatg aataaatata    1500
tttctagaga acagtttaca aagcctcatc tttccaaact taaccatttg tgtatgcgtc    1560
aaatcaagcc tgcacgcgtg cgtgcatgtg tgtgtgtatt ttccccaaat ggtgatgatg    1620
agcagtgctt tgcatgaaac tagattttat caattt                              1656

<210> SEQ ID NO 52
<211> LENGTH: 536
<212> TYPE: PRT
<213> ORGANISM: Homo sapiens

<400> SEQUENCE: 52

Ile Met Asn Glu Lys Trp Asp Thr Asn Ser Ser Glu Asn Trp His Pro
1               5                   10                  15

Ile Trp Asn Val Asn Asp Thr Lys His His Leu Tyr Ser Asp Ile Asn
                20                  25                  30

Ile Thr Tyr Val Asn Tyr Tyr Leu His Gln Pro Gln Val Ala Ala Ile
            35                  40                  45

Phe Ile Ile Ser Tyr Phe Leu Ile Phe Phe Leu Cys Met Met Gly Asn
        50                  55                  60

Thr Val Val Cys Phe Ile Val Met Arg Asn Lys His Met His Thr Val
65                  70                  75                  80

Thr Asn Leu Phe Ile Leu Asn Leu Ala Ile Ser Asp Leu Leu Val Gly
                85                  90                  95

Ile Phe Cys Met Pro Ile Thr Leu Leu Asp Asn Ile Ile Ala Gly Trp
            100                 105                 110

Pro Phe Gly Asn Thr Met Cys Lys Ile Ser Gly Leu Val Gln Gly Ile
        115                 120                 125

Ser Val Ala Ala Ser Val Phe Thr Leu Val Ala Ile Ala Val Asp Arg
    130                 135                 140

Phe Gln Cys Val Val Tyr Pro Phe Lys Pro Lys Leu Thr Ile Lys Thr
145                 150                 155                 160

Ala Phe Val Ile Ile Met Ile Ile Trp Val Leu Ala Ile Thr Ile Met
                165                 170                 175

Ser Pro Ser Ala Val Met Leu His Val Gln Glu Glu Lys Tyr Tyr Arg
            180                 185                 190

Val Arg Leu Asn Ser Gln Asn Lys Thr Ser Pro Val Tyr Trp Cys Arg
        195                 200                 205
```

-continued

Glu Asp Trp Pro Asn Gln Glu Met Arg Lys Ile Tyr Thr Thr Val Leu
    210                 215                 220
Phe Ala Asn Ile Tyr Leu Ala Pro Leu Ser Leu Ile Val Ile Met Tyr
225                 230                 235                 240
Gly Arg Ile Gly Ile Ser Leu Phe Arg Ala Ala Val Pro His Thr Gly
                245                 250                 255
Arg Lys Asn Gln Glu Gln Trp His Val Val Ser Arg Lys Lys Gln Lys
            260                 265                 270
Ile Ile Lys Met Leu Leu Ile Val Ala Leu Leu Phe Ile Leu Ser Trp
        275                 280                 285
Leu Pro Leu Trp Thr Leu Met Met Leu Ser Asp Tyr Ala Asp Leu Ser
    290                 295                 300
Pro Asn Glu Leu Gln Ile Ile Asn Ile Tyr Ile Tyr Pro Phe Ala His
305                 310                 315                 320
Trp Leu Ala Phe Gly Asn Ser Ser Val Asn Pro Ile Ile Tyr Gly Phe
                325                 330                 335
Phe Asn Glu Asn Phe Arg Arg Gly Phe Gln Glu Ala Phe Gln Leu Gln
            340                 345                 350
Leu Cys Gln Lys Arg Ala Lys Pro Met Glu Ala Tyr Ala Leu Lys Ala
        355                 360                 365
Lys Ser His Val Leu Ile Asn Thr Ser Asn Gln Leu Val Gln Glu Ser
    370                 375                 380
Thr Phe Gln Asn Pro His Gly Glu Thr Leu Leu Tyr Arg Lys Ser Ala
385                 390                 395                 400
Glu Lys Pro Gln Gln Glu Leu Val Met Glu Leu Lys Glu Thr Thr
                405                 410                 415
Asn Ser Ser Glu Ile Lys Glu Leu Val Ser Leu Tyr Tyr Ala Leu Tyr
            420                 425                 430
Ile Ile His Cys Phe Leu Trp Leu Cys Thr Ser Asn Phe Ser Lys Asn
        435                 440                 445
Val Leu Asn Lys Thr Phe Thr Glu Ser Pro Leu Trp Gln Lys Asn Lys
    450                 455                 460
Thr Lys Met Val Ile Arg Ser Thr Ile Leu Cys Cys Ile Lys Ile Arg
465                 470                 475                 480
Arg Val Thr Thr Cys Leu His Glu Ile Tyr Phe Arg Thr Val Tyr Lys
                485                 490                 495
Ala Ser Ser Phe Gln Thr Pro Phe Val Tyr Ala Ser Asn Gln Ala Cys
            500                 505                 510
Thr Arg Ala Cys Met Cys Val Cys Ile Phe Pro Lys Trp Ala Val Leu
        515                 520                 525
Cys Met Lys Leu Asp Phe Ile Asn
    530                 535

<210> SEQ ID NO 53
<211> LENGTH: 601
<212> TYPE: DNA
<213> ORGANISM: Rattus norvegicus

<400> SEQUENCE: 53
agaccttggg gatcctgggg cctgggatcc tatgtggcca atggtggcc actcaccccc      60 tcttctctcc ccttcctgtg ctcagatgag gtgcctctgc tcttggcttt gcctcctcct     120
gcctctgagt gcctgctttc ctctgctgga cagaagggga cccacagaca tcggtgacat     180
cggagccaga atgagctggg tccagctgac tgagggacac accccccgct cagttcaaag     240

```
tccacggcca caggccctgc tcgtggtggc caaggagcag caggcctctc gcagggagca      300
cactggcttc cgtctaggga ggcaggacag tggcagtgaa gccacggggt tcctgcccac      360
tgactcagag aaggccagcg ccccctggg  gactctggca gaggagctca gcagctacag      420
ccggcggaag gaggcttca  gcttccgctt cggccggtga gggcctgcgt ggactctgcc      480
ctgactgtcc actcaagtct gggccccaac cttgagagag aatatcacaa tgaatctggt      540
ggtgaatagg tgtgtgtttg tttttattta caactttgct aaagtgaaag acctgggtgg      600
t                                                                      601
```

<210> SEQ ID NO 54
<211> LENGTH: 198
<212> TYPE: PRT
<213> ORGANISM: Rattus norvegicus

<400> SEQUENCE: 54

```
Asp Leu Gly Asp Pro Gly Ala Trp Asp Pro Met Trp Pro Asn Gly Gly
1               5                   10                  15

His Ser Pro Pro Leu Leu Ser Pro Ser Cys Ala Gln Met Arg Cys Leu
            20                  25                  30

Cys Ser Trp Leu Cys Leu Leu Leu Pro Leu Ser Ala Cys Phe Pro Leu
        35                  40                  45

Leu Asp Arg Arg Gly Pro Thr Asp Ile Gly Asp Ile Gly Ala Arg Met
50                  55                  60

Ser Trp Val Gln Leu Thr Glu Gly His Thr Pro Arg Ser Val Gln Ser
65                  70                  75                  80

Pro Arg Pro Gln Ala Leu Leu Val Val Ala Lys Glu Gln Gln Ala Ser
                85                  90                  95

Arg Arg Glu His Thr Gly Phe Arg Leu Gly Arg Gln Asp Ser Gly Ser
            100                 105                 110

Glu Ala Thr Gly Phe Leu Pro Thr Asp Ser Glu Lys Ala Ser Gly Pro
        115                 120                 125

Leu Gly Thr Leu Ala Glu Glu Leu Ser Ser Tyr Ser Arg Arg Lys Gly
130                 135                 140

Gly Phe Ser Phe Arg Phe Gly Arg Gly Pro Ala Trp Thr Leu Pro Leu
145                 150                 155                 160

Ser Thr Gln Val Trp Ala Pro Thr Leu Arg Glu Asn Ile Thr Met Asn
                165                 170                 175

Leu Val Val Asn Arg Cys Val Phe Val Phe Ile Tyr Asn Phe Ala Lys
            180                 185                 190

Val Lys Asp Leu Gly Gly
        195
```

<210> SEQ ID NO 55
<211> LENGTH: 1302
<212> TYPE: DNA
<213> ORGANISM: Rattus norvegicus

<400> SEQUENCE: 55

```
atgcaggcgc tcaacatcac cgcggagcag ttctcccggc tgctgagcgc gcacaacctg       60
actcgggagc agttcattca tcgctatggg ctgagaccgc tggtctacac tccggagctg      120
cccgcgcgtg ctaaagtggc ctttgcgctg gcaggagcac tcattttttgc cctggcgctc      180 ttcggcaact ctctggtcat ctatgtggtg acccgcagca aggccatgcg caccgtcacc      240
aacatcttca tctgctctct ggcactcagt gatctgctca ttgccttctt ctgcatcccc      300
```

```
gtcacgatgc tccagaacat ctccgacaag tggctgggtg gtgccttcat ctgcaagatg    360
gtaccctttg tccagtccac ggccgtcgtg acagaaatcc tcaccatgac ctgcatcgct    420
gttgagaggc accaaggact tgtccatcct tttaaaatga agtggcagta caccacccga    480
agggccttca cgatcttggg cgtggtctgg ttggcggcca tcatcgtagg atcacccatg    540
tggcacgtgc aacgccttga gattaagtat gacttcctct atgaaaaaga acacatctgc    600
tgcttggaag aatgggccag ccccgtgcac cagagaatct acagcacctt cattctcgtc    660
atcctcttcc tcctgcctct tgtggtaatg ctagtcctct atagcaagat tggctatgaa    720
ctgtggatca agaagagagt gggagacagt tcagcgcttc aaactatcca cgggaaagaa    780
atgtccaaaa tagccaggaa gaagaagcgg gctgtcatta tgatggtgac tgtggtggct    840
ctctttgctg catgctgggc acctttccac gttgttcaca tgatggttga gtacagtaat    900
tttgaaaaag aatatgatga tgtcacaatc aagatggtct ttgctgtcgc gcagacaatt    960
ggcttttca actccatctg taatccctt gtgtatgcgt ttatgaatga aaacttcaaa   1020
aagaattttc tgtctgctgt ttgttattgc atagtgaaag aatcctcctc cccagcacgg   1080
aagcctggga attctggaat atcaatgatg cagaagagag caaagttatc tcgaccacag   1140
cgtccagtgg aagaaaccaa aggagacaca ttcagtgatg ccagcattga tgtcaaattg   1200
tgcgagcagc cgcgggagaa aagacaactc aagagacagc tagccttctt cagttctgaa   1260
ctttctgaaa actctacttt tggtagtggc catgaactgt aa                      1302

<210> SEQ ID NO 56
<211> LENGTH: 433
<212> TYPE: PRT
<213> ORGANISM: Rattus norvegicus

<400> SEQUENCE: 56

Met Gln Ala Leu Asn Ile Thr Ala Glu Gln Phe Ser Arg Leu Leu Ser
1               5                   10                  15

Ala His Asn Leu Thr Arg Glu Gln Phe Ile His Arg Tyr Gly Leu Arg
            20                  25                  30

Pro Leu Val Tyr Thr Pro Glu Leu Pro Ala Arg Ala Lys Val Ala Phe
        35                  40                  45

Ala Leu Ala Gly Ala Leu Ile Phe Ala Leu Ala Leu Phe Gly Asn Ser
    50                  55                  60

Leu Val Ile Tyr Val Val Thr Arg Ser Lys Ala Met Arg Thr Val Thr
65                  70                  75                  80

Asn Ile Phe Ile Cys Ser Leu Ala Leu Ser Asp Leu Leu Ile Ala Phe
                85                  90                  95

Phe Cys Ile Pro Val Thr Met Leu Gln Asn Ile Ser Asp Lys Trp Leu
            100                 105                 110

Gly Gly Ala Phe Ile Cys Lys Met Val Pro Phe Val Gln Ser Thr Ala
        115                 120                 125

Val Val Thr Glu Ile Leu Thr Met Thr Cys Ile Ala Val Glu Arg His
    130                 135                 140

Gln Gly Leu Val His Pro Phe Lys Met Lys Trp Gln Tyr Thr Thr Arg
145                 150                 155                 160

Arg Ala Phe Thr Ile Leu Gly Val Val Trp Leu Ala Ala Ile Ile Val
                165                 170                 175

Gly Ser Pro Met Trp His Val Gln Arg Leu Glu Ile Lys Tyr Asp Phe
            180                 185                 190
```

Leu Tyr Glu Lys Glu His Ile Cys Cys Leu Glu Trp Ala Ser Pro
            195                 200                 205

Val His Gln Arg Ile Tyr Ser Thr Phe Ile Leu Val Ile Leu Phe Leu
    210                 215                 220

Leu Pro Leu Val Val Met Leu Val Leu Tyr Ser Lys Ile Gly Tyr Glu
225                 230                 235                 240

Leu Trp Ile Lys Lys Arg Val Gly Asp Ser Ala Leu Gln Thr Ile
                245                 250                 255

His Gly Lys Glu Met Ser Lys Ile Ala Arg Lys Lys Arg Ala Val
            260                 265                 270

Ile Met Met Val Thr Val Val Ala Leu Phe Ala Ala Cys Trp Ala Pro
    275                 280                 285

Phe His Val Val His Met Met Val Glu Tyr Ser Asn Phe Glu Lys Glu
    290                 295                 300

Tyr Asp Asp Val Thr Ile Lys Met Val Phe Ala Val Ala Gln Thr Ile
305                 310                 315                 320

Gly Phe Phe Asn Ser Ile Cys Asn Pro Phe Val Tyr Ala Phe Met Asn
                325                 330                 335

Glu Asn Phe Lys Lys Asn Phe Leu Ser Ala Val Cys Tyr Cys Ile Val
            340                 345                 350

Lys Glu Ser Ser Ser Pro Ala Arg Lys Pro Gly Asn Ser Gly Ile Ser
            355                 360                 365

Met Met Gln Lys Arg Ala Lys Leu Ser Arg Pro Gln Arg Pro Val Glu
    370                 375                 380

Glu Thr Lys Gly Asp Thr Phe Ser Asp Ala Ser Ile Asp Val Lys Leu
385                 390                 395                 400

Cys Glu Gln Pro Arg Glu Lys Arg Gln Leu Lys Arg Gln Leu Ala Phe
                405                 410                 415

Phe Ser Ser Glu Leu Ser Glu Asn Ser Thr Phe Gly Ser Gly His Glu
            420                 425                 430

Leu

<210> SEQ ID NO 57
<211> LENGTH: 1307
<212> TYPE: DNA
<213> ORGANISM: Rattus norvegicus

<400> SEQUENCE: 57
cagacagtat ggaggcggag ccctcccagc ctcccaacgg cagctggccc ctgggtcaga      60
acgggagtga tgtggagacc agcatagcaa ccagcctcac cttctcctcc tactaccaac     120
actcctctcc ggtggcagcc atgttcatcg cggcctacgt gctcatcttc ctcctctgca     180
tggtgggcaa caccctggtc tgcttcattg tgctcaagaa ccggcacatg cgcactgtca     240
ccaacatgtt tatcctcaac ctggccgtca gcgacctgct ggtgggcatc ttctgcatgc     300
ccacaaccct tgtggacaac cttatcactg gttggccttt tgacaacgcc acatgcaaga     360
tgagcggctt ggtgcagggc atgtccgtgt ctgcatcggt tttcacactg gtggccatcg     420
ctgtggaaag gttccgctgc atcgtgcacc ctttccgcga aagctgacc cttcggaagg     480
cgctgttcac catcgcggtg atctgggctc tggcgctgc catcatgtgt ccctcggcgg     540
tcactctgac agtcacccga gaggagcatc acttcatgct ggatgctcgt aaccgctcct     600
acccgctcta tcgtgctgg aggcctggc ccgagaaggg catgcgcaag gtctacaccg     660
cggtgctctt cgcgcacatc tacctggtgc cgctggcgct catcgtagtg atgtacgtgc     720

-continued

```
gcatcgcgcg caagctatgc caggcccccg gtcctgcgcg cgacacggag gaggcggtgg      780
ccgagggtgg ccgcacttcg cgccgtaggg cccgcgtggt gcacatgctg gtcatggtgg      840
cgctcttctt cacgttgtcc tggctgccac tctgggtgct gctgctgctc atcgactatg      900
gggagctgag cgagctgcaa ctgcacctgc tgtcggtcta cgccttcccc ttggcacact      960
ggctggcctt cttccacagc agcgccaacc ccatcatcta cggctacttc aacgagaact     1020
tccgccgcgg cttccaggct gccttccgtg cacagctctg ctggcctccc tgggccgccc     1080
acaagcaagc ctactcggag cggcccaacc gcctcctgcg caggcgggtg gtggtggacg     1140
tgcaacccag cgactccggc ctgccatcag agtctggccc cagcagcggg gtcccagggc     1200
ctggccggct gccactgcga aatgggcgtg tggcccatca ggatggcccg ggggaagggc     1260
caggctgcaa ccacatgccc ctcaccatcc cggcctggaa catttga                  1307
```

<210> SEQ ID NO 58
<211> LENGTH: 434
<212> TYPE: PRT
<213> ORGANISM: Rattus norvegicus

<400> SEQUENCE: 58

```
Asp Ser Met Glu Ala Glu Pro Ser Gln Pro Pro Asn Gly Ser Trp Pro
1               5                   10                  15
Leu Gly Gln Asn Gly Ser Asp Val Glu Thr Ser Ile Ala Thr Ser Leu
            20                  25                  30
Thr Phe Ser Ser Tyr Tyr Gln His Ser Ser Pro Val Ala Ala Met Phe
        35                  40                  45
Ile Ala Ala Tyr Val Leu Ile Phe Leu Leu Cys Met Val Gly Asn Thr
    50                  55                  60
Leu Val Cys Phe Ile Val Leu Lys Asn Arg His Met Arg Thr Val Thr
65                  70                  75                  80
Asn Met Phe Ile Leu Asn Leu Ala Val Ser Asp Leu Leu Val Gly Ile
                85                  90                  95
Phe Cys Met Pro Thr Thr Leu Val Asp Asn Leu Ile Thr Gly Trp Pro
            100                 105                 110
Phe Asp Asn Ala Thr Cys Lys Met Ser Gly Leu Val Gln Gly Met Ser
        115                 120                 125
Val Ser Ala Ser Val Phe Thr Leu Val Ala Ile Ala Val Glu Arg Phe
    130                 135                 140
Arg Cys Ile Val His Pro Phe Arg Glu Lys Leu Thr Leu Arg Lys Ala
145                 150                 155                 160
Leu Phe Thr Ile Ala Val Ile Trp Ala Leu Ala Leu Ile Met Cys
                165                 170                 175
Pro Ser Ala Val Thr Leu Thr Val Thr Arg Glu Glu His His Phe Met
            180                 185                 190
Leu Asp Ala Arg Asn Arg Ser Tyr Pro Leu Tyr Ser Cys Trp Glu Ala
        195                 200                 205
Trp Pro Glu Lys Gly Met Arg Lys Val Tyr Thr Ala Val Leu Phe Ala
    210                 215                 220
His Ile Tyr Leu Val Pro Leu Ala Leu Ile Val Val Met Tyr Val Arg
225                 230                 235                 240
Ile Ala Arg Lys Leu Cys Gln Ala Pro Gly Pro Ala Arg Asp Thr Glu
                245                 250                 255
Glu Ala Val Ala Glu Gly Gly Thr Ser Arg Arg Ala Arg Val
            260                 265                 270
```

-continued

```
Val His Met Leu Val Met Val Ala Leu Phe Phe Thr Leu Ser Trp Leu
        275                 280                 285

Pro Leu Trp Val Leu Leu Leu Ile Asp Tyr Gly Glu Leu Ser Glu
    290                 295                 300

Leu Gln Leu His Leu Leu Ser Val Tyr Ala Phe Pro Leu Ala His Trp
305             310                 315                 320

Leu Ala Phe Phe His Ser Ser Ala Asn Pro Ile Ile Tyr Gly Tyr Phe
                325                 330                 335

Asn Glu Asn Phe Arg Arg Gly Phe Gln Ala Ala Phe Arg Ala Gln Leu
                340                 345                 350

Cys Trp Pro Pro Trp Ala Ala His Lys Gln Ala Tyr Ser Glu Arg Pro
        355                 360                 365

Asn Arg Leu Leu Arg Arg Val Val Val Asp Val Gln Pro Ser Asp
    370                 375                 380

Ser Gly Leu Pro Ser Glu Ser Gly Pro Ser Ser Gly Val Pro Gly Pro
385             390                 395                 400

Gly Arg Leu Pro Leu Arg Asn Gly Arg Val Ala His Gln Asp Gly Pro
                405                 410                 415

Gly Glu Gly Pro Gly Cys Asn His Met Pro Leu Thr Ile Pro Ala Trp
                420                 425                 430

Asn Ile
```

RFAMIDE-RELATED PEPTIDES AND METHODS THEREOF

CROSS REFERENCE TO RELATED APPLICATIONS AND INCORPORATION BY REFERENCES OF MATERIALS SUBMITTED ELECTRONICALLY

This application claims the priority benefit under 35 U.S.C. §119(e) of U.S. Provisional Application No. 61/320,505, filed Apr. 2, 2010, the disclosure of which is incorporated herein by reference in its entirety.
Incorporated by reference in its entirety is a computer-readable nucleotide/amino acid sequence listing submitted concurrently herewith and identified as follows: ASCII text file named "46140a_SeqListing.txt," 45,746 bytes, created Dec. 23, 2014.

STATEMENT REGARDING FEDERALLY SPONSORED RESEARCH OR DEVELOPMENT

This invention was made with government support under R21HL093627 awarded by the National Institute of Health (NIH). The government has certain rights in the invention.

BACKGROUND OF THE INVENTION

Heart failure is the leading cause of death, yet the peptidergic mechanisms involved in cardiac dysfunction are not completely understood (Jessup, M., and Brozena S. (2003)). Identifying small cardioregulatory peptides is significant because it can provide potential target molecules for drug development and therapeutic strategies to address cardiac dysfunction. Vertebrate FMRFamide-related peptides (FaRPs) are expressed in regions of the central nervous system involved in cardiac regulation (Fukusumi et al. (2001), Ukena et al. (2001), Yano et al. (2003)); however, relatively little is known about their function. The first RFamide-containing peptide discovered was the invertebrate tetrapeptide, FMRFamide (Price, D. A., and Greenberg, M. J. (1977)). The isolation of FMRFamide from clam ganglia as a cardioregulatory peptide led to the subsequent identification of structurally-related bio- and cardio-active peptides throughout the animal kingdom, in invertebrates and vertebrates (Fukusumi, S. et al. (2006), Nichols, R. (2003)).

The FaRP superfamily of FMRFamide-related peptides is subdivided into smaller groups based on the XRFamide motif, where X defines the subgroup. The invertebrate myosuppressin peptides belong to the LRFamide subgroup. The structure of Drosophila melanogaster myosuppressin, dromyosuppressin (DMS), is TDVDHVFLRFamide (SEQ ID NO: 1) (Nichols, R. (1992)). Myosuppressins have been extensively studied in invertebrates as myoinhibitory peptides that decrease heart rate and amplitude of ejection (Robb, S. et al. (1989), Robb, S., and Evans, P. (1994), Wasielewski, O., and Skonieczna, M. (2008), Stevens, J. S. et al. (2009), Angioy, A. M. et al. (2007)).

While the vast majority of FaRP-related cardiovascular research has been done in invertebrates, relatively little is known about the function of this cardioregulatory peptide family in mammals. However, mammalian RFamide-related peptide (RFRP) genes encode RFRP-1, which contains a C-terminal LRFamide (Hinuma, S. Et al. (2000), Liu, Q. Et al. (2001)). The structure of the human RFRP-1 (hRFRP-1) peptide is MPHSFANLPLRFamide (SEQ ID NO: 2) (Ubuka T. et al. (2009) PLoS One 4 (22): e8400; pages 1-7). An endogenous peptide with high structure identity to hRFRP-1 was isolated from bovine hypothalamus (Fukusumi, S. Et al. (2001)). Additionally, clusters of hRFRP-1 immunoreactive neurons and fibers are found in mammalian hypothalamus and nucleus of the solitary tract (NTS), an important site for integrative regulation of the cardiovascular system (Fukusumi, S. et al. (2001), Ukena, K., and Tsutsui, K. (2001), Yano, T. et al. (2003)).

U.S. Pat. Nos. 7,192,723 and 7,217,808 include disclosure of particular RFamide-related peptides for uses involving prolactin secretion and other therapeutic uses. WO 2007/045906, and WO 2004 026904 include disclosure of the particular RFamide-related peptides INSP207, INTP026, INTP027, and INTP028. U.S. Pat. No. 7,354,724 includes disclosure related to Drosophila melanogaster G protein coupled receptors. Particular cardiac effects of a non-vertebrate RFamide-related peptide hormone are discussed in Stevens J S et al. 2009, J Exp Biol: 212(Pt 24): 3961-76. Fang Q et al. (Eur J Pharmacol 2009 621: (1-3): 61-66) discuss cardiovascular effects of the RF amide-related peptide 26RFa.

As set forth in further detail below, methods and compositions directed to RFRP-1 polypeptides, are useful for modulating cardiac contractile function, for preventing and/or treating cardiac disorders; as well as tools for discovering agents that can modulate cardiac function, as tools for identifying the receptor of RFRP-1, and as tools for identifying diseases related to cardiac failure.

DESCRIPTION OF THE DRAWINGS

FIG. 2B; Table 1 percent change in departure velocity, peak height, and return velocity during 15 minutes perfusion with peptide. Values for each concentration (y-axis; hRFRP-1 (log [ ]) were compared to media control (C) with 1-way ANOVA followed by a Dunnett's Multiple Comparison Test with p<0.05 considered statistically significant (*; Table 1). The best-fit $EC_{50}$ values were calculated to be $5\times10^{-11}$ M (shortening rate), $5\times10^{-10}$M (shortening amplitude), and $5\times10^{-11}$ M (re-lengthening rate). Recordings were made from 7-20, 1-day and 2-day myocytes isolated from n=2-3 hearts.

Figure 7:
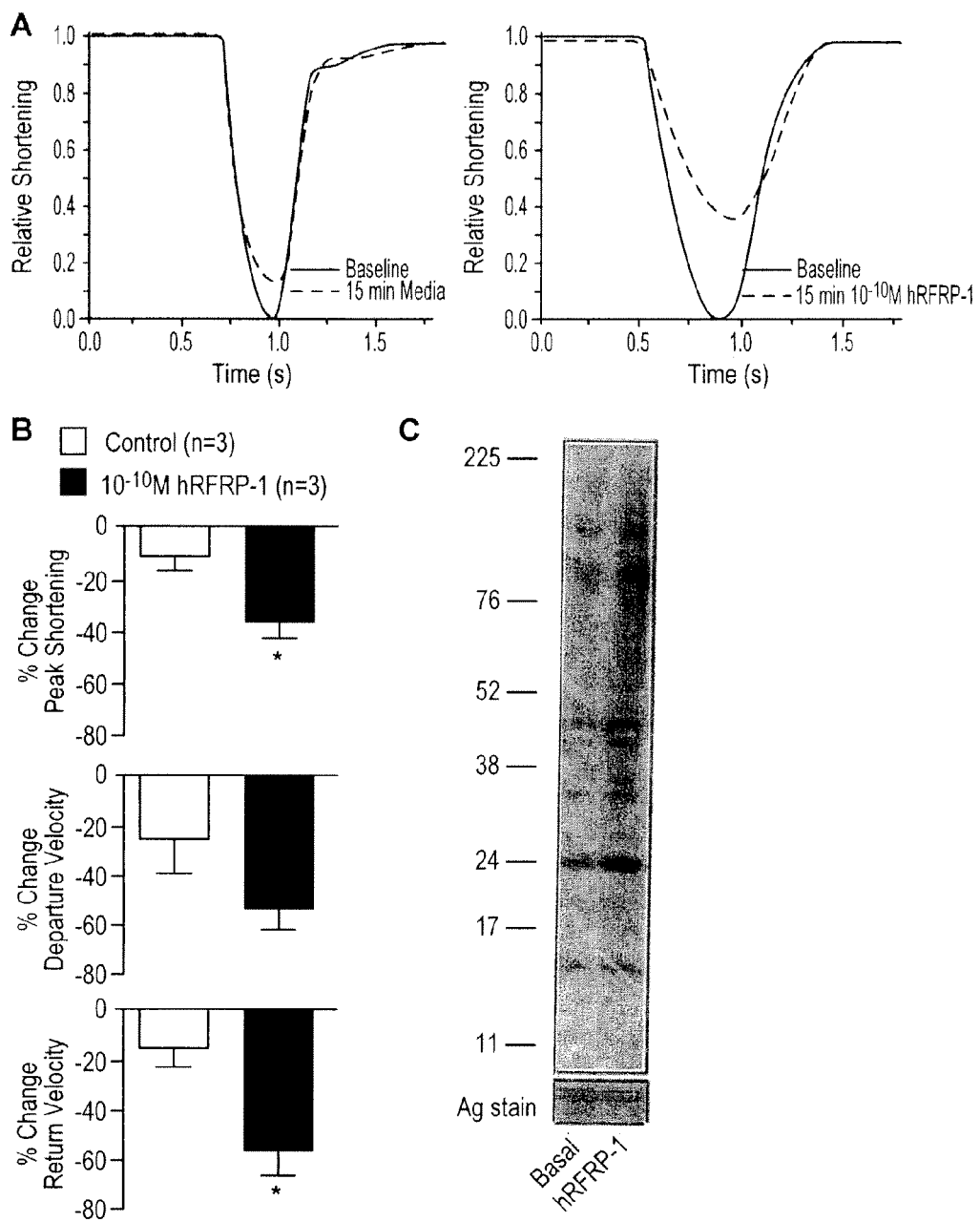
FIG. 7. A. Representative sarcomere shortening traces in isolated adult rabbit cardiac myocytes paced at 0.5 Hz. A signal-averaged recording from 10 traces was made in myocytes 1 day after isolation (n=3). Recordings show shortening before and 15 minutes after initiating perfusion with $10^{-10}$ M hRFRP-1 or media (control) at 37° C.

B. Summary of the changes in peak shortening and the rates of shortening and re-lengthening for experiments represented in FIG. 7A.

C. $^{32}$P-labeling of rabbit cardiac myocyte proteins in response to control, no peptide, (left lane) and $10^{-7}$ M hRFRP-1 (right lane). Myocytes were labeled for 1 hour in $^{32}$P-orthophosphate and then treated with hRFRP-1 ($10^{-7}$ M) in radiolabel-free media for 154 minutes. The putative phosphorylation targets include troponin I (24 kDa), troponin T (35 kDa), and myosin light chain 2 (15 kDa). Silver-stained images are shown below to indicate protein loading.

Figure 8:
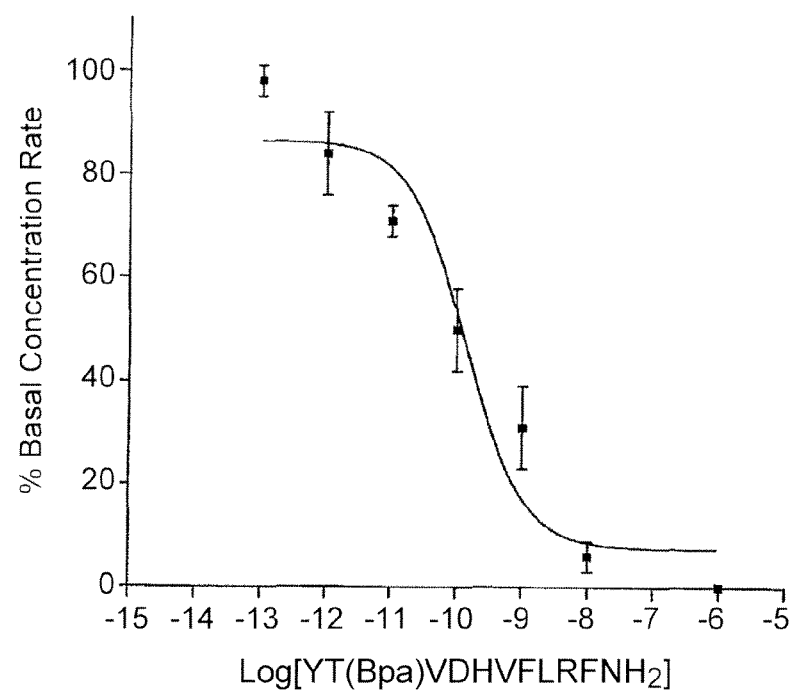

FIG. 8 Y-[Bpa2]DMS affects *D. melanogaster* heart rate in vivo. Y-[Bpa2]DMS decreased heart rate in a dose-dependent manner; EC50=1.3–$10^{-10}$M (n≥16).

Figure 9A:
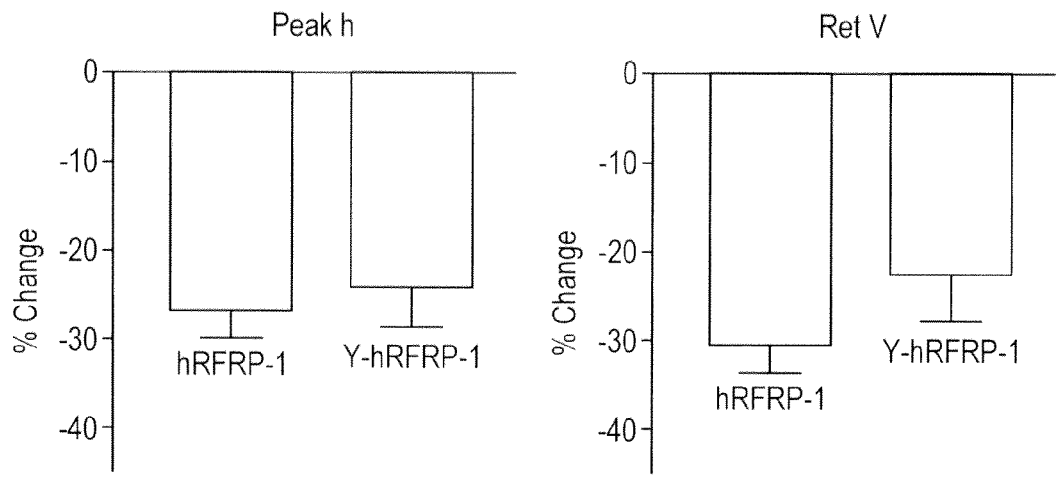

FIG. 9:

FIG. 9A: Comparison of $10^{-8}$M hRFRP-1 and Y-hRFRP-1 on peak shortening and relaxation. Results are shown for the percent change in peak shortening (peak h) and relaxation (ret v) in isolated rat myocytes (n≥14).

Figure 9B:
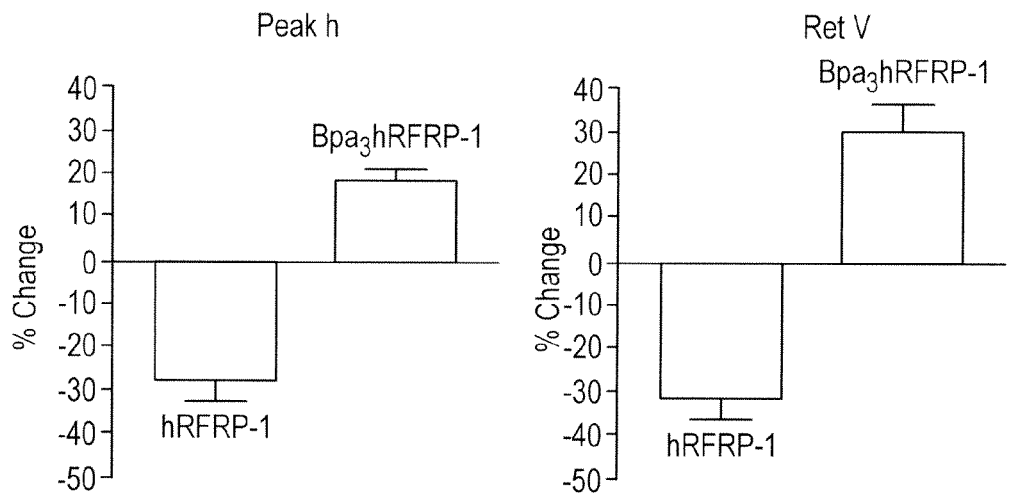

FIG. 9B: Comparison of $10^{-7}$M hRFRP-1 and [Bpa3] hRFRP-1 on peak shortening and relaxation. Results are the percent change in peak shortening (peak h) and relaxation (ret v) in isolated rat cardiac myocytes (n≥16).

Figure 10:
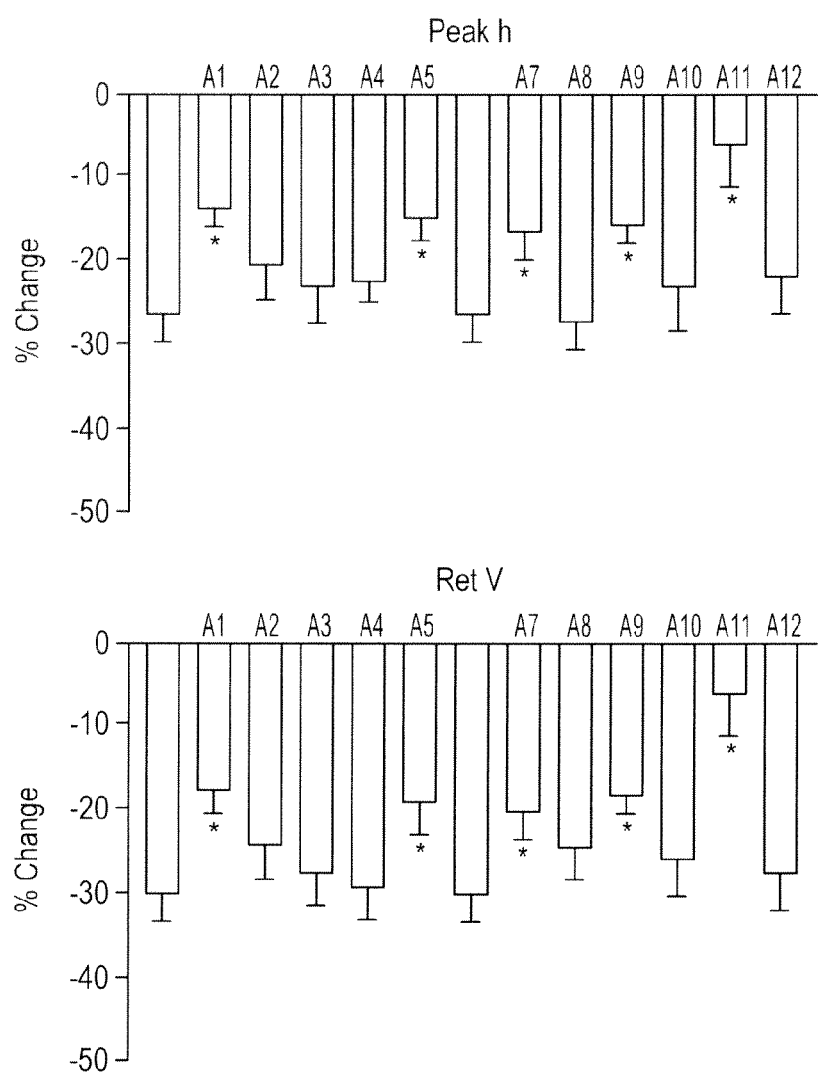

FIG. 10: Effects of $10^{-8}$M alanine analogs on peak shortening and relaxation. Results show the percent change in peak height and return velocity in rat cardiac myocytes. Analogs are indicated by A#, where # indicates the residue substituted with alanine; hRFRP-1 (open). An asterisk (*) indicates statistical significance, $p<0.05$ (n≥20).

Figure 11:
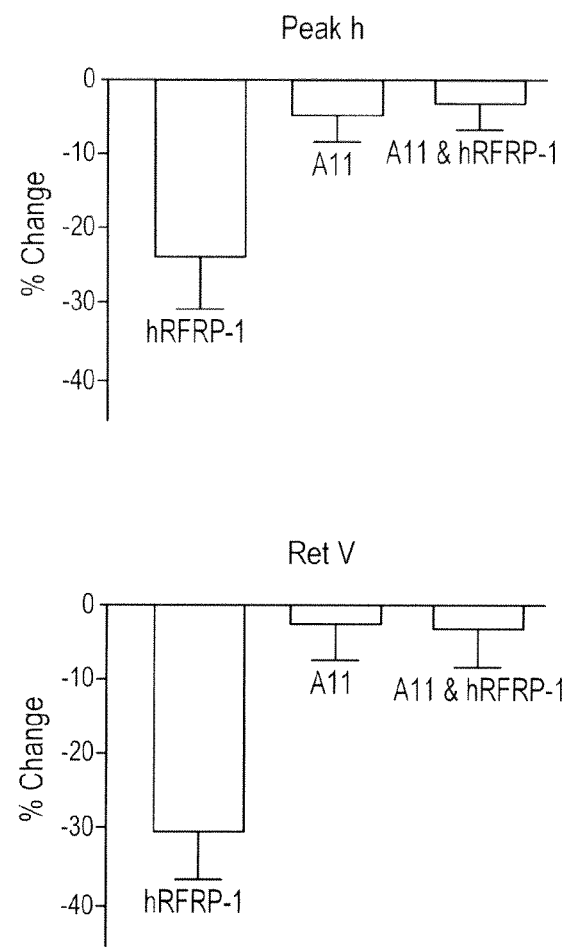

FIG. 11: The effects of $10^{-8}$M hRFRP-1 (filled), $10^{-7}$M [A11]hRFRP-1 (stippled), and $10^{-8}$M hRFRP-1 in the presence of $10^{-7}$M [A11]hRFRP-1 (vertical lines). Results show [A11]hRFRP-1 is a hRFRP-1 antagonist for the percent change in peak h and ret v in rat myocytes (n≥14).

Figure 12:
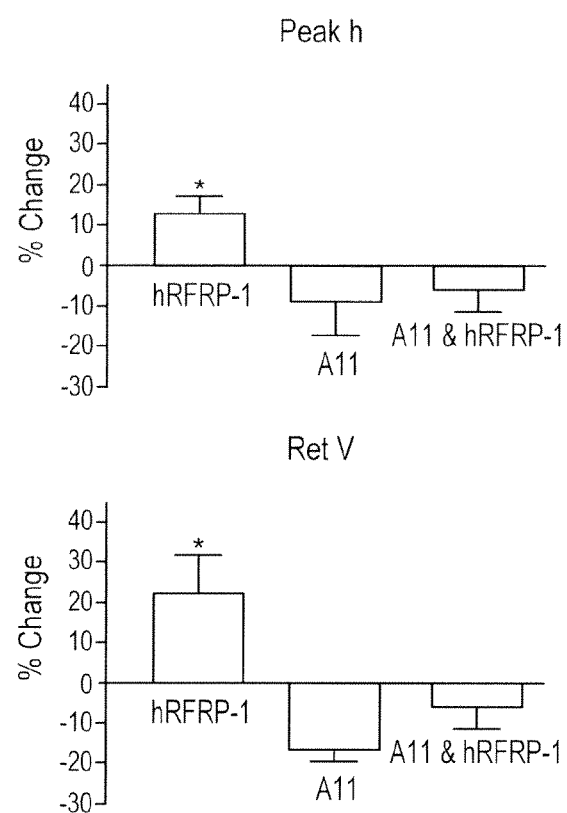

FIG. 12: The effects of $10^{-7}$M [Bpa3]hRFRP-1 (filled), $10^{-7}$M [A11]hRFRP-1 (unfilled), and $10^{-7}$M [Bpa3] hRFRP-1 in the presence of $10^{-7}$M [A11]hRFRP-1 (checkered). [A11]hRFRP-1 attenuates the effects of [Bpa3] hRFRP-1 on peak h and ret v in rat cardiac myocytes (n≥12).

Figure 13:
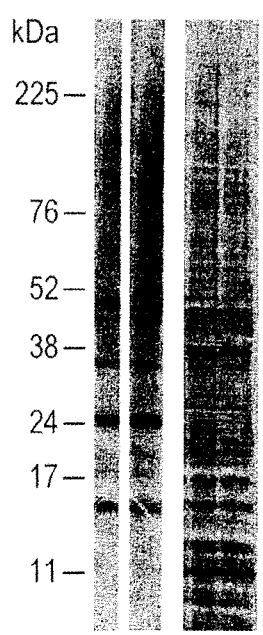

FIG. 13: (left)$^{32}$P-labeled rat myocyte proteins in response to control, no peptide, (lane 1); $10^{-8}$M hRFRP-1 (lane 2) including phosphatase inhibitor, calyculin A. Silver-stained proteins are shown in lane 3 (control) and in lane 4 ($10^{-8}$M hRFRP-1). Lanes are numbered from left to right, 1, 2, 3, and 4.

Figure 14:
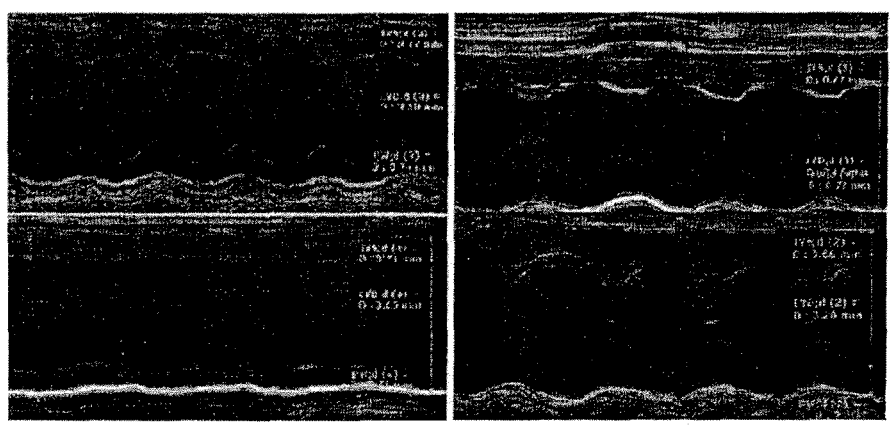

FIG. 14: Echocardiography results in mouse in response to tail vein injections. 2-D M mode images; $10^{-8}$M hRFRP-1 (left, top, pre-injection, t=0; bottom, t=10 min post-injection); saline (right), pre-injection (top; t=0) and post-injection (bottom; t=10 min).

Figure 15:
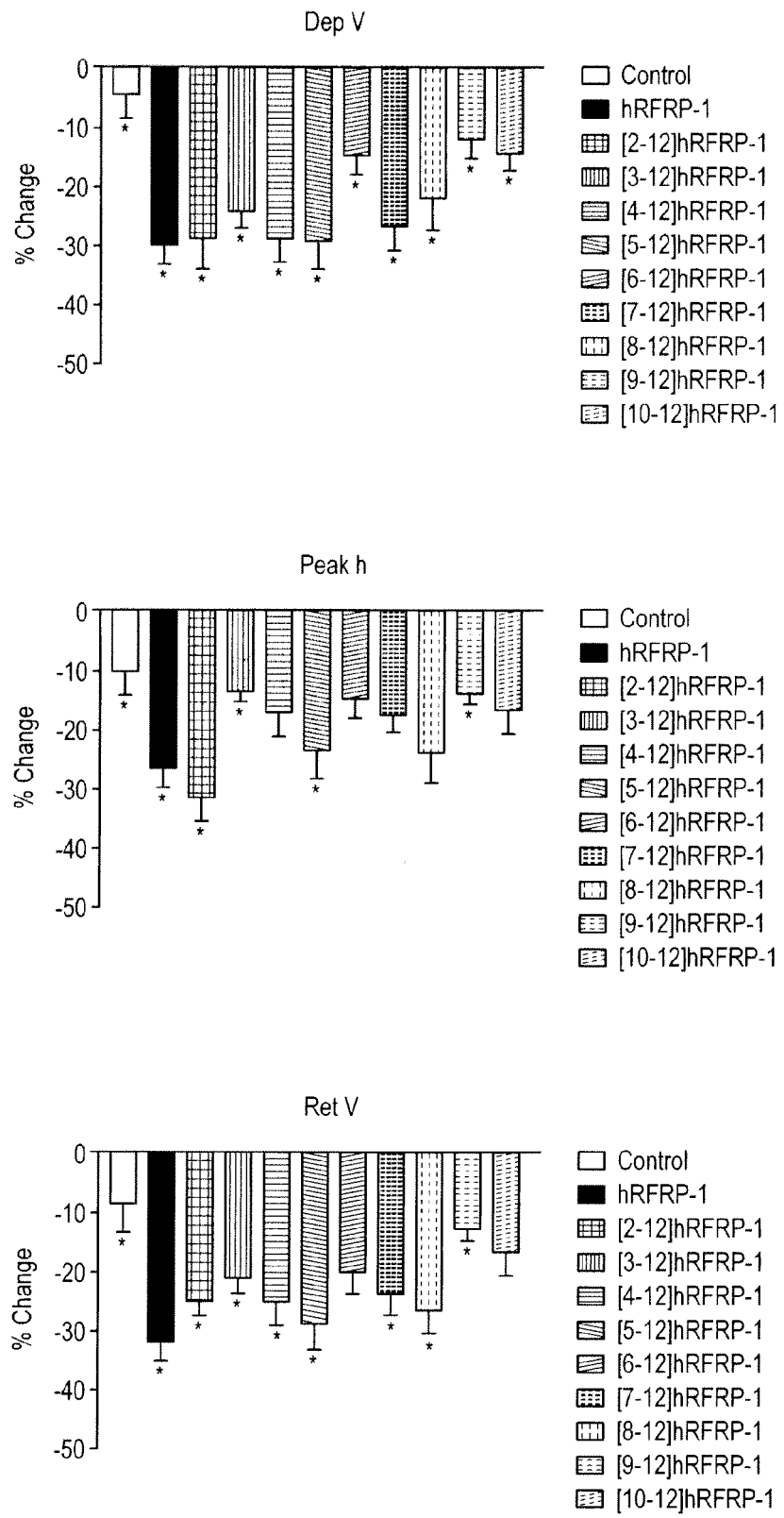

FIG. 15: The effects of control (media only), hRFRP-1, and truncated hRFRP-1 peptides on departure velocity, peak height and return velocity on isolated adult rat cardiac myocytes.

Figure 16:
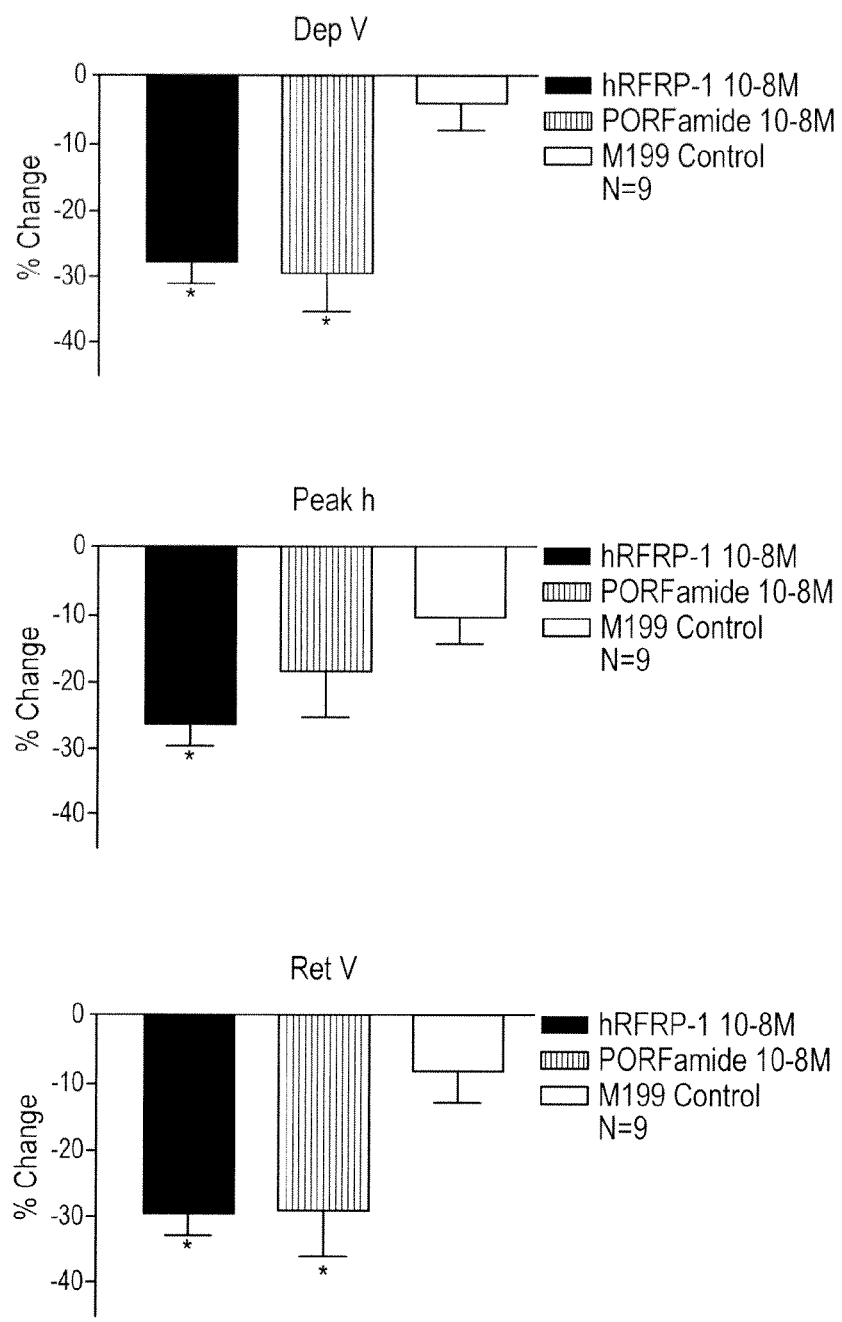

FIG. 16: The effects of $10^{-8}$ M PQRFamide compared to $10^{-8}$ M hRFRP-1 and control (media only) on isolated adult rat cardiac myocytes.

Figure 17:
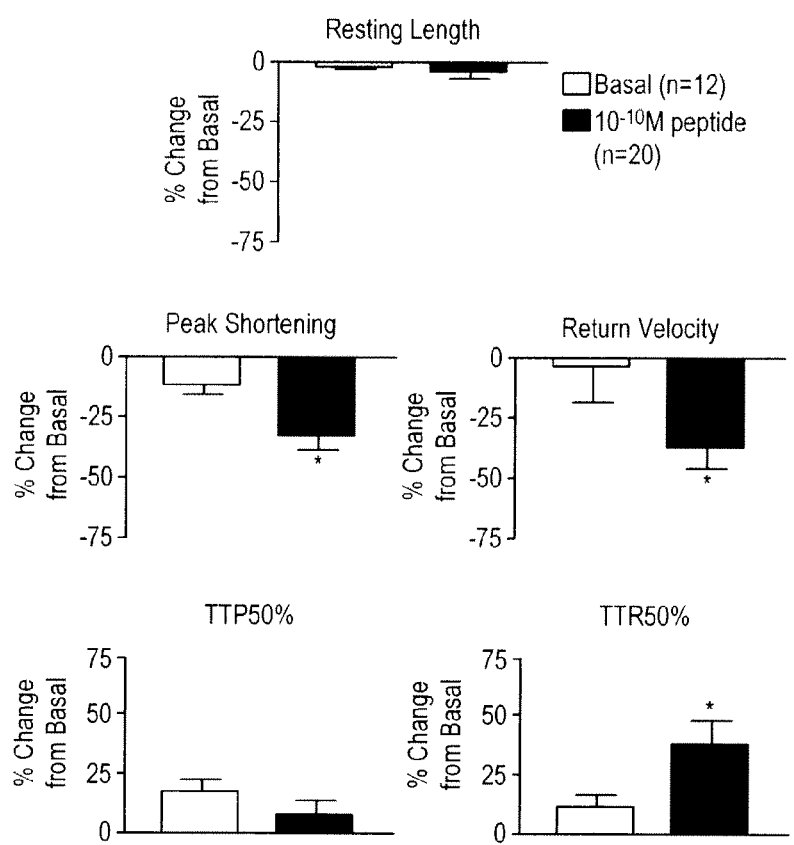

FIG. 17. The effect of $10^{-10}$M hRFRP-1 (filled; n=20), a control, media, no peptide (open; n=12) on cardiac function in isolated rabbit cardiac myocytes. Mean value t standard error of mean; $p<0.05$ (*) was considered significantly different from control.

Figure 18:
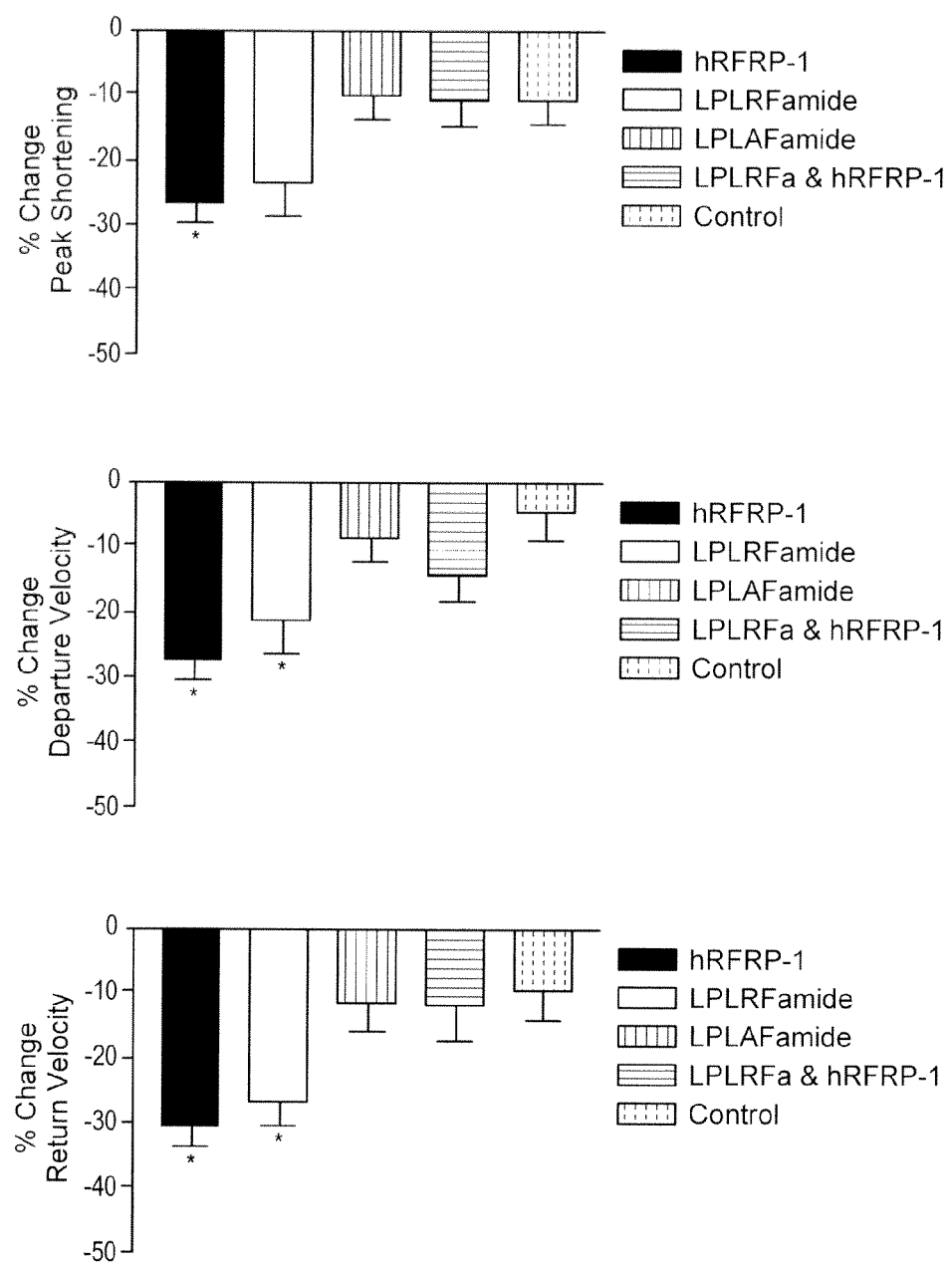

FIG. 18. The effects of $10^{-8}$M hRFRP-1 (filled), $10^{-8}$M LPLRFamide (SEQ ID NO: 3) (checkerboard), $10^{-8}$M LPLAFamide (vertical lines), and 10–8M hRFRP-1 and 10–8M LPLAFamide (horizontal lines) on peak shortening, departure velocity, and return velocity in isolated rat cardiac myocytes. Results are presented as the percent change. The data demonstrate LPLAFamide is a hRFRP-1 antagonist.

Figure 19:
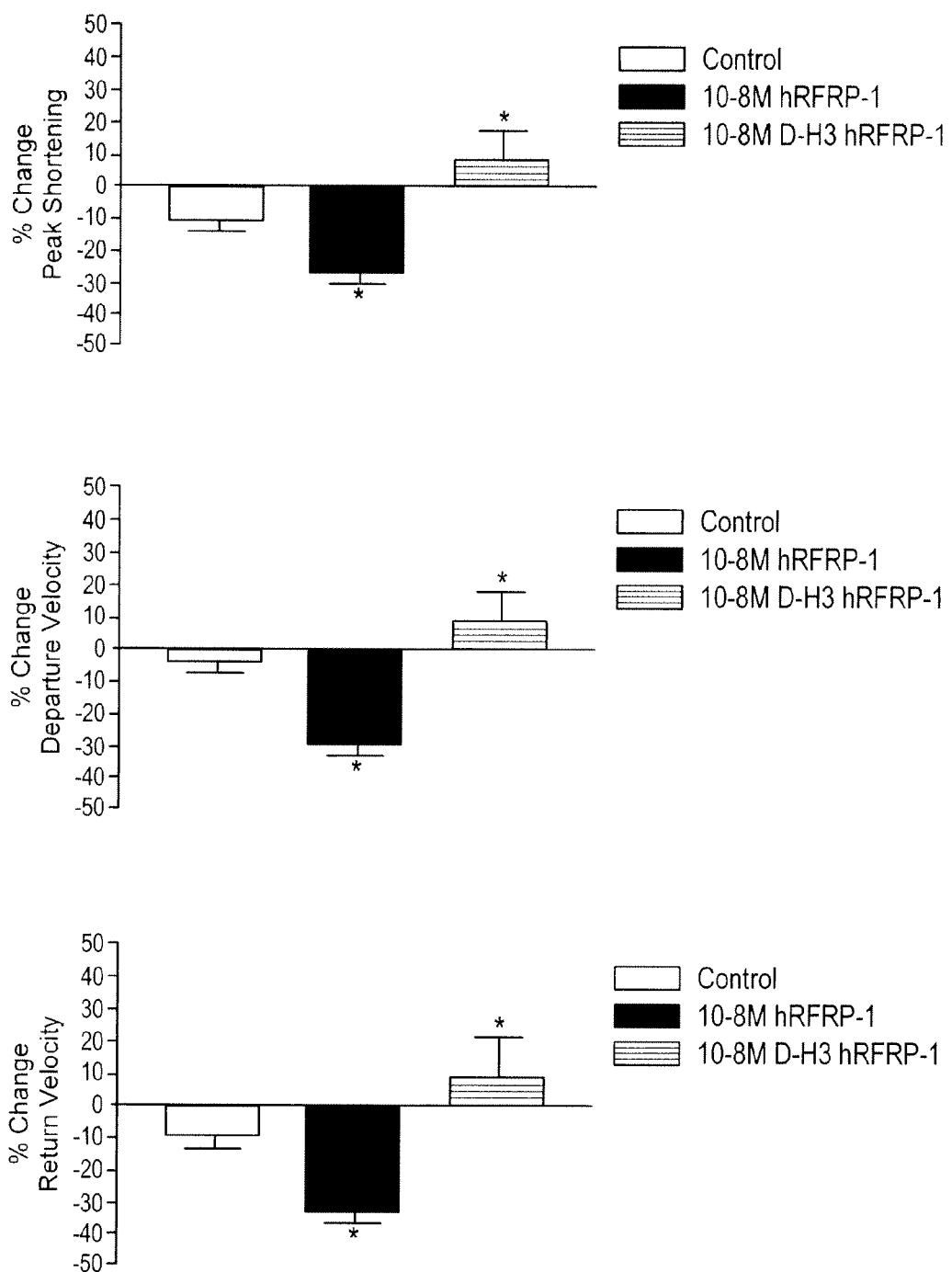

FIG. 19. Comparison of the effect of 10-8M [D-H3] hRFRP-1 (horizontal lines), $10^{-8}$M hRFRP-1 (filled), and control (open; no peptide or peptide analog, media only) on peak shortening, departure velocity, and return velocity in isolated rat cardiac myocytes. Results are presented as the percent change. The data demonstrate $10^{-8}$M [D-H3] hRFRP-1 is a hRFRP-1 reverse agonist.

DESCRIPTION OF THE INVENTION

The invention is related to the discovery that RFRP-1 peptides, mammalian orthologs of DMS produce a highly specific and dramatic depressant effect on mammalian cardiac myocytes and on in vivo cardiac performance. More particularly, the invention is related to isolated or synthetic peptide compositions, the structures of which peptides are based on modification of the human RFRP-1 (hRFRP-1) sequence: MPHSFANLPLRFamide (SEQ ID NO: 2) and its orthologs. Structure-function studies of hRFRP-1 and other members of FMRFamide-related peptides as described herein further provide that particular modified peptides of the invention, as well as hRFRP-1 are similarly capable of modulating mammalian cardiac function.

Accordingly, in one aspect, the invention is drawn to isolated or synthetic peptides comprising amino acid sequences that are modifications of the amino acid sequence of hRFRP-1 set forth above, and methods thereof. In one embodiment, the modified hRFRP-1 sequences of the invention comprise a tetrapeptide represented by the amino acid sequence X9-X10-X11-F, wherein X10 is L or Q, and X9 and X11 are each independently a natural or modified amino acid. In another, the sequences LPLRF (SEQ ID NO: 3) or PQRF motifs are retained as the C-terminal amino acids of modified hRFRP-1 sequences of the invention. In another, the C-terminal phenylalanine represented by F is amidated, or otherwise modified or selected from L-phenylalanine or D-phenylalanine. In any and all aspects of the invention described herein, the embodiments encompass those inventive peptides in which the C-terminal residue is amidated; including the C-terminal phenylalanine. Accordingly, any of the inventive peptides disclosed herein can be selected from those having a C-terminal Famide. Accordingly, whether explicitly set forth or not, a C-terminal "F" or phenylalanine includes the representation of either Famide, or phenylalanine in free acid form. It is recognized in this invention that the C-terminal tetrapeptide amino acids X9-X10-X11-F as set forth above, modulate cardiac function.

By "modulate cardiac function" or "modulates cardiac function" is meant that one or more peptides described herein determinably exert a positive or negative effect on cardiac contractile function. This positive or negative effect is determinable by in vive or in vitro methods known to the ordinarily skilled artisan, and as otherwise described herein. Thus, by utilizing methods in vivo directed to measuring heart rate, stroke volume, ejection fraction, and/or cardiac output, including the methods described herein, it is determinable whether one or more peptides described herein exhibit a positive or negative chronotropic, inotropic or lusitropic effect on the heart, including vertebrate or mammalian heart. Furthermore, by utilizing methods in vitro directed to measuring parameters of sarcomere shortening and/or relaxation in isolated myocytes, including the methods described herein, it is determinable whether one or more peptides described herein exhibit a positive or negative effect on cardiac contractile function; and therefore can modulate cardiac function. These parameters include at least one of peak height, departure velocity, and/or return velocity. Whether using the in vive or in vitro methods, it is recognized that the ordinarily skilled artisan will include appropriate controls, reference subjects, and/or samples in order to ensure that the observed positive or negative effect on cardiac contractile function are due to the action of one or more peptides of the invention. It is recognized that the inventive peptides described herein can affect cardiac function by blocking the signaling action of an RFamide-containing peptide, including hRFRP-1.

As described and illustrated below, Applicant has discovered that administration of hRFRP-1 in vivo in mammals, and in vitro in mammalian-derived myocytes, establish that hRFRP-1 can determinably decrease cardiac contractile function, and thereby modulate cardiac function. The inventive peptides described herein that are modified peptides derived from the parent hRFRP-1 peptide sequence include agonists, including reverse- and super-agonists; and antagonists of one or more actions of hRFRP-1 on cardiac contractility. In this regard, for the purposes of the invention, by an "agonist of hRFRP-1" or "hRFRP-1 agonist" is intended to mean that the inventive peptide can also determinably decrease cardiac contractile function in comparison to hRFRP-1. By a "super-agonist of hRFRP-1" or an "hRFRP-1 super-agonist" is intended to mean that the inventive peptide can determinably decrease cardiac contractile function in comparison to hRFRP-1, with more potency than the parent hRFRP-1 peptide. An example of a super-agonist peptide of the invention is the 11 mer peptide: PHSFANLPLRFamide (SEQ ID NO: 4); and the peptide is provided as a particular embodiment of the invention. By a "reverse agonist of hRFRP-1" or an "hRFRP-1 reverse agonist" is intended to mean that the inventive peptide can determinably increase cardiac contractile function in comparison to hRFRP-1. By an "antagonist of hRFRP-1" or "hRFRP-1 antagonist" is intended to mean that the inventive peptide can determinably attenuate the effect of hRFRP-1 on cardiac contractile function. In this regard, by "attenuate" is intended to mean a decrease or elimination of the effect of hRFRP-1 on cardiac contractile function. The invention provides methods of screening for compounds that are agonists; including reverse- and super-agonists; and antagonists of one or more actions of hRFRP-1 on cardiac contractility. It is recognized that the particular order of the steps of the methods described herein are not limiting, so long as the methods readily allow for determination of the effects of one or more of the inventive peptides described herein, in comparison to the effect of hRFRP-1 on cardiac contractile function. For example, it is recognized that in order to determine whether an inventive peptide described herein can attenuate the effect of hRFRP-1 on cardiac contractile function as determinable by measuring one or more parameters of sarcomere shortening in isolated myocytes based on the teachings provided herein; the ordinarily skilled artisan can include a step in which one or more myocytes are pre-incubated with hRFRP-1, and a measurement of cardiac contractility is made; followed by addition of an inventive peptide described herein as a test agent to the pre-incubated sample, and subsequent measurement of the parameter. In this manner, it is determinable whether the co-incubation of myocytes with hRFRP-1 and the test agent decreases the effect observed after incubation with hRFRP-1 alone. Alternatively, for example, the steps can include a reference sample in which one or more myocytes are incubated with hRFRP-1 alone, and a second sample in which hRFRP-1, the test agent, and one or more myocytes are co-incubated for the same period of time as the reference sample. Subsequently, the particular endpoint measurement is taken from the test sample and the reference sample, and the appropriate comparison is made. Again, it is determined from the comparison, whether the test agent attenuates the action of hRFRP-1 on cardiac contractility. Such variations of the particular assay design that are readily variable by the ordinarily skilled artisan are encompassed by the methods of the invention.

The invention encompasses methods of treatment with one or more of the inventive peptides or pharmaceutical compositions comprising the peptides, as described herein. It is recognized that the selection of a particular inventive peptide or composition for treating a particular disorder can be made by one of ordinary skilled in the art, depending on the ability of the peptide to decrease or increase cardiac contractile function when administered to a subject in need thereof; and considering whether it would be beneficial to treat the particular disorder by increasing or decreasing cardiac contractile function. It is also recognized that the inventive peptides described herein can affect cardiac function by blocking the signaling action of an RFamide-containing peptide, including hRFRP-1.

In this manner, the ordinarily skilled artisan can select among the hRFRP-1 agonists and antagonists described herein. For example, it is envisioned that in the case of heart failure, including for example decompensated congestive heart failure, it would be desirable to elicit a positive ionotropic effect and increase cardiac contractile function. Therefore, in such a case, it would be desirable to select a reverse agonist, or antagonist of hRFRP-1. On the other hand, it is further recognized that in the case of other particular disorders it may be desirable to decrease cardiac contractile function, for example, in certain surgical situations, arrhythmias, and fibrillations including for example, drug-induced arrhythmias. In this regard, by a "cardiac disorder" is intended to mean an acute or chronic pathological condition affecting the heart, which condition is associated with abnormal contractile function of the heart. It is recognized that the abnormal contractile function can be a primary disorder in a subject or symptomatic of another acute or chronic primary pathological condition. In particular embodiments, administration of one or more of the inventive peptides to cardiac cell or tissue detectably establishes rhythm in post-arrhythmic cardiac cell or tissue. In related embodiments, the administration is in vivo or in vitro.

Thus, with reference to the parent peptide MPHSFANL-PLRFamide (SEQ ID NO: 2) (referred to as "hRFRP-1" hereinafter) the invention encompasses peptides that are modified peptides derived from the parent hRFRP-1 peptide sequence. In particular embodiments, the inventive peptides retain the LPLRF (SEQ ID NO: 3), PQRF, or PLAF amino acids at their C-terminus. The modifications include truncations, substitutions, deletions, and insertions of the hRFRP-1 amino acids, as well as chemical modifications of the amino acids. In particular embodiments, the invention encompasses peptides that are modified peptides derived from the parent hRFRP-1 peptide sequence, and retain the amino acids PLXF, PQXF, FLXF, FQXF, APLXF (SEQ ID NO: 5), APQXF (SEQ ID NO: 6), AFLXF (SEQ ID NO: 7), AFQXF (SEQ ID NO: 8), VPLXF (SEQ ID NO: 9), VPQXF (SEQ ID NO: 10), VFLXF (SEQ ID NO: 11), or VFQXF (SEQ ID NO: 12) amino acids at their C-terminus; wherein X is any natural or modified amino acid other than L-arginine. In one embodiment, the C-terminal phenylalanine represented by F is amidated.

More particularly, in one aspect, the invention provides isolated peptides comprising the amino acid sequence:

X1-X2-X3-X4-X5-X6-X7-X8-X9-X10-X11-F (SEQ ID NO: 13) wherein,
any one of amino acids X1 to X8 is present or absent, X9 and X11 are present, X10 is L or Q, and said peptide modulates cardiac function in a vertebrate; or a salt, amide or ester thereof. In any of the aspects of the invention described herein, the designations X1, X2, X3, X4, X5, X6, X7, X8, X9, X10, X11 correspond to the position of the amino acids contained in the parent MPHSFANLPLRFamide peptide (SEQ ID NO: 2). The invention encompasses those peptides in which any one of X1, X2, X3, X4, X5, X6, X7, X8, X9, X10, X11 is independently selected as the amino acid contained in the corresponding position of the parent peptide. Accordingly, in particular embodiments of the invention, X1, X2, X3, X4, X5, X6, X7, X8, X9, X10, X11 is each independently and respectively selected from M, P, H, S, F, A, N, L, P, L, and R.

For the purposes of the invention, any of the amino acids comprised by the peptides of the invention, including those represented by the designations "X1", "X2", "X3", "X4", "X5", "X6", "X7", "X8", "X9", "X10", or "X11", is a natural or modified amino acid. For the purposes of the invention, the term "natural amino acid" is intended to mean the well known L-isomers of naturally occurring amino acids. The term "modified amino acid" is intended to mean amino acids other than the well known L-isomers of naturally occurring amino acids. For the purposes of the invention, the term "modified amino acid" as used herein includes amino acids that are chemically or post-translationally modified, as well as D-counterparts of L-isomers of naturally occurring amino acids, and chemical compounds used as alternatives to amino acids in synthesis of peptidomimetic compounds. Such compounds are well known to those of skill in the art and are typically produced through the substitution of certain R groups or amino acids in a peptide with non-natural substitutions. Such substitutions may increase the stability; solubility; permeability, including blood-brain barrier permeability; bioavailability; or activity of resultant peptide.

Thus, modified peptides derived from the parent hRFRP-1 peptide sequence are produced when one or more amino acids in the naturally occurring hRFRP-1 is substituted with a different natural amino acid, an amino acid derivative, a synthetic amino acid, an amino acid analog or a non-native amino acid. Such modifications include one or more conservative or non-conservative amino acid substitutions, deletions or insertions which yield an inventive peptide that modulates cardiac function. The modifications can provide for certain advantages in the use of the inventive peptides such as increased potency; solubility; permeability, including blood-brain barrier permeability; bioavailability; stability; decreased toxicity; or degradation under physiological conditions.

The conservative substitutions typically include the substitution of one amino acid for another with similar characteristics such as substitutions within the following groups: valine, glycine; glycine, alanine; valine, isoleucine; aspartic acid, glutamic acid; asparagine, glutamine; serine, threonine; lysine, arginine; and phenylalanine, tyrosine. The non-polar (hydrophobic) group of amino acids include alanine, leucine, isoleucine, valine, proline, phenylalanine, tryptophan and methionine. The polar neutral group of amino acids include glycine, serine, threonine, cysteine, tyrosine, asparagine and glutamine. The positively charged (basic) group of amino acids include arginine, lysine and histidine. The negatively charged (acidic) group of amino acids include aspartic acid and glutamic acid.

Utilizing less conservative or non-conservative substitutions can result in the particularly desired modified hRFRP-1 of the invention, e.g., by causing desirable changes in charge, conformation and other biological properties. Such substitutions would include for example, substitution of hydrophilic residue for a hydrophobic residue, substitution of a cysteine or proline for another residue, substitution of a residue having a small side chain for a residue having a bulky side chain or substitution of a residue having a net positive charge for a residue having a net negative charge. When the result of a given substitution cannot be predicted with certainty, the derivatives may be readily assayed according to the methods disclosed herein to determine the presence or absence of the desired characteristics; including for example, modulation of cardiac function, and the ability to act as an agonist or antagonist of hRFRP-1.

Just as it is possible to replace substituents of the peptide scaffold, it is also possible to substitute functional groups which decorate the scaffold with groups characterized by similar features (i.e., R-groups which are part of each amino acid). Where an agonist of hRFRP-1 is desired, these substitutions will typically be conservative, i.e., the replacement group will have approximately the same size, shape, hydrophobicity and charge as the original group. Non-sequence modifications may include chemical derivatization of portions of the parent or inventive peptide described herein.

In particular embodiments of the invention, the inventive peptides comprise chemically modified peptides that are iodinated, amidated, sulfated, singly or multiply halogenated, alkylated, carboxylated, or phosphorylated. The peptide can be singly or multiply acylated, such as with an acetyl group, with a farnesyl moiety, or with a fatty acid, which may be saturated, monounsaturated or polyunsaturated. The fatty acid may also be singly or multiply fluorinated. The invention also encompasses methionine analogs of hRFRP1, for example the methionine sulfone and methionine sulfoxide analogs. The invention also includes salts of hRFRP-1, such as ammonium salts, including alkyl or aryl ammonium salts, sulfate, hydrogen sulfate, phosphate, hydrogen phosphate, dihydrogen phosphate, thiosulfate, carbonate, bicarbonate, benzoate, sulfonate, thiosulfonate, mesylate, ethyl sulfonate and benzensulfonate salts.

The modified hRFRP-1 peptides of the invention also include peptidomimetic compounds derived from hRFRP-1. Synthesis of peptidomimetic compounds are well known to those of skill in the art and such compounds are produced through the substitution of certain R groups or amino acids in the peptide with non-natural moieties. Such substitutions are used to increase the stability; solubility; permeability; including blood-brain barrier permeability; bioavailability; or a particularly desired activity of hRFRP-1 as set forth herein; or retain the ability of hRFRP-1 to modulate cardiac function. Examples of suitable peptidomimetics include D amino acids of the corresponding L amino acids, tetrazol (Zabrocki et al., J. Am. Chem. Soc. 110:5875-5880 (1988)); isosteres of amide bonds (Jones et al., Tetrahedron Lett. 29: 3853-3856 (1988)); LL-3-amino-2-propenidone-6-carboxylic acid (LL-Acp) (Kemp et al., J. Org. Chem. 50:5834-5838 (1985)). Similar analogs are shown in Kemp et al., Tetrahedron Lett. 29:5081-5082 (1988) as well as Kemp et al., Tetrahedron Lett. 29:5057-5060 (1988). Kemp et al., Tetrahedron Lett. 29:4935-4938 (1988) and Kemp et al., J. Org. Chem. 54:109-115 (1987). Other suitable peptidomimetics are shown in Nagai and Sato, Tetrahedron Lett. 26:647-650 (1985); Di Maio et al., J. Chem. Soc. Perkin Trans., 1687 (1985); Kahn et al., Tetrahedron Lett. 30:2317 (1989); Olson et al., J. Am. Chem. Soc. 112:323-333 (1990); Garvey et al., J. Org. Chem. 56:436 (1990). Further suitable peptidomimetics include hydroxy-1,2,3,4-tetrahydroisoquinoline-3-carboxylate (Miyake et al., J. Takeda Res. Labs 43:53-76 (1989)); 1,2,3,4-tetrahydro-isoquinoline-3-carboxylate (Kazmierski et al., J. Am. Chem. Soc. 133:2275-2283 (1991)); histidine isoquinolone carboxylic acid (HIC) (Zechel et al., Int. J. Pep. Protein Res. 43 (1991)); (2S,3S)-methyl-phenylalanine, (2S,3R)-methyl-phenylalanine, (2R, 3S)-methyl-phenylalanine and (2R,3R)-methyl-phenylalanine (Kazmierski and Hruby, Tetrahedron Lett. (1991)).

The modified hRFRP-1 peptides of the invention can also include those peptides derived from hRFRP-1 wherein at least one peptidic backbone bond of the parent hRFRP-1 has been chemically modified or altered to a non-naturally occurring peptidic backbone bond. In other words, the naturally occurring peptide bond between the nitrogen atom of one amino acid residue to the carbon atom of the next has been altered to non-naturally occurring bonds by reduction, alkylation (for example methylation) on the nitrogen atom, or the bonds have been replaced by a reduced bond such as an amine, urea bond, or sulfonamide bond, etheric bond, or a thioetheric bond. In this regard, it is recognized that the side chain of the residue may be shifted to the backbone nitrogen to obtain N-alkylated-Glycine. Examples of uses of peptidomimetic moieties and synthesis of non-naturally occurring peptidic backbones and other chemical modifications of peptides include those described in U.S. Pat. Nos. 7,217,808; 7,192,723; and 7,683,031; the entire contents of which are hereby incorporated herein by reference.

The modified hRFRP-1 peptides of the invention can also include those peptides which are cyclic molecules, or are cyclized. For the purposes of the invention, a "cyclic molecule" refers, in one instance, to a peptide of the invention in which a ring is formed by the formation of a peptide bond between the nitrogen atom at the N-terminus and the carbonyl carbon at the C-terminus. "Cyclized" refers to the forming of a ring by a covalent bond between the nitrogen at the N-terminus of the compound and the side chain of a suitable amino acid in the sequence present therein, preferably the side chain of the C-terminal amino acid. For example, an amide can be formed between the nitrogen atom at the N-terminus and the carbonyl carbon in the side chain of an aspartic acid or a glutamic acid. Alternatively, the compound can be cyclized by forming a covalent bond between the carbonyl at the C-terminus of the compound and the side chain of a suitable amino acid in the sequence contained therein, preferably the side chain of the N-terminal amino acid. For example, an amide can be formed between the carbonyl carbon at the C-terminus and the amino nitrogen atom in the side chain of a lysine or an ornithine. Additionally, the compound can be cyclized by forming an ester between the carbonyl carbon at the C-terminus and the hydroxyl oxygen atom in the side chain of a serine or a threonine. "Cyclized" also refers to forming a ring by a covalent bond between the side chains of two suitable amino acids in the sequence present in the compound, preferably the side chains of the two terminal amino acids. For example, a disulfide can be formed between the sulfur atoms in the side chains of two cysteines. Alternatively, an ester can be formed between the carbonyl carbon in the side chain of, for example, a glutamic acid or an aspartic acid, and the oxygen atom in the side chain of, for example, a serine or a threonine. An amide can be formed between the carbonyl carbon in the side chain of, for example, a glutamic acid or an aspartic acid, and the amino nitrogen in the side chain of, for example, a lysine or an ornithine. Methods for preparing cyclic molecules derived from peptides, or cyclized peptides, are disclosed, for example, in U.S. Pat. No. 7,683,031; the entire contents of which are hereby incorporated herein by reference.

In addition, a compound can be cyclized with a linking group between the two termini, between one terminus and the side chain of an amino acid in the compound, or between the side chains to two amino acids in the peptide or peptide derivative. Suitable linking groups are disclosed in Lobl et al., WO 92/00995 and Chiang et al., WO 94/15958, the teachings of which are incorporated into this application by reference.

As also discussed in further detail below, a particular inventive peptide of the invention including a chemically modified, or peptidomimetic derivative of phenylalanine (Phe; F) is "[Bpa3]hRFRP-1" in which the third amino acid of the dodecameric parent hRFRP-1 (MPHSFANLPLRF-amide) (SEQ ID NO: 2) is replaced by the moiety p-benzoyl-phenylalanine (referred to as "Bpa" hereinafter). Applicants have made the inventive discovery that [Bpa3]hRFRP-1 is a reverse agonist of hRFRP-1. In particular embodiments, the modified hRFRP-1 peptides of the invention include those in which an internal histidine of the parent RFRP-1 peptide is replaced with Bpa. While not limited by theory, it is envisioned that Bpa represents a substitution that presents sufficient steric hindrance to reverse the direction of the modulatory effect of hRFRP-1 on cardiac function; that is from decreasing cardiac function to increasing cardiac function. The invention further encompasses uses of [Bpa3]hRFRP-1 and the other inventive peptides as set forth herein.

The peptides comprising the sequences described herein can be synthesized by well known manual or automated sequencing techniques employing solid phase peptide synthesis (e.g., t-BOC or F-MOC) method, by solution phase synthesis, or by other well suitable techniques including combinations of the foregoing methods. The t-BOC and F-MOC methods, which are well known and widely used, are described for example, in Merrifield, J. Am. Chem. Soc., 88:2149 (1963); Meienhofer, Hormonal Proteins and Peptides, C. H. Li, Ed., Academic Press, 1983, pp. 48-267; and Barany and Merrifield, in The Peptides, E. Gross and J. Meienhofer, Eds., Academic Press, New York, 1980, pp. 3-285. Methods of solid phase peptide synthesis are described in Merrifield, R. B., Science, 232:341 (1986); Carpino, L. A. and Han, G. Y., J. Org. Chem., 37:3404 (1972); and Gauspohl, H. et al., Synthesis 5:315 (1992)). The teachings of these references are incorporated herein by reference. Accordingly, any and all peptides according to the various aspects and embodiments of the invention described herein can be provided as synthetic peptides; and the invention encompasses providing synthetic peptides comprising the sequences described herein.

It is recognized that, as an alternative to chemical synthesis methods, particular peptides of the invention can be produced by well known recombinant techniques, including those adapted for large scale production of proteins and peptides. In this regard, by utilizing standard molecular biological techniques, including for example, those described in Molecular Cloning," 2nd Ed. (J. Sambrook et al., Cold Spring Harbor Lab. Press, 1989); nucleic acids encoding one or more of the peptides of the invention can be expressed in host cells, and the peptides can be subsequently isolated and purified from the host cells utilizing well known methods. Host cells can include bacterial, mammalian, or insect cell lines; including for example, CHO cells, E. coli, and Sf9 cells. Such methods can include use of well known fusion protein tags for ease of isolation and purification of the desired expressed peptide. Typically, such tags are conveniently removable by limited proteolysis. It is further recognized that inventive peptides produced by such recombinant techniques can be further modified by chemical means as described herein. Thus, by utilizing recombinant techniques, endogenous RFRP-1 peptides can be modified to include one or more modifications including amino acid insertions, deletions, substitutions and truncations. Thus, the peptides of the invention encompass those inventive peptides described herein that are isolated subsequent to chemical synthesis, or isolated subsequent to production by recombinant methods.

Throughout the specification and drawings of the present application, the abbreviations used in describing peptides, amino acids and so forth are those recommended by the IUPAC-IUB Commission on Biochemical Nomenclature or those conventionally used in the art; including the following amino acid abbreviations:
Gly or G: Glycine; Ala or A: Alanine; Val or V: Valine; Leu or L: Leucine; Ile or I: Isoleucine; Ser or S: Serine; Thr or T: Threonine; Cys or C: Cysteine; Met or M: Methionine; Glu or E: Glutamic acid; Asp or D: Aspartic acid; Lys or K: Lysine; Arg or R: Arginine; His or H: Histidine; Phe or F: Phenylalanine; Tyr or Y: Tyrosine; Trp or W: Tryptophan; Pro or P: Proline; Asn or N: Asparagine; Gln or Q: Glutamine. Unless otherwise specified, amino acids that may have optical isomers are intended to represent their L-isomer, and peptides are presented in the N-terminus to C-terminus direction as is conventionally understood in the art. Particular aspects and embodiments of the invention are provided in further detail below.

In one aspect, the invention provides an isolated peptide comprising the amino acid sequence
X1-X2-X3-X4-X5-X6-X7-X8-X9-X10-X11-F (SEQ ID NO: 13) wherein,
any one of amino acids X1 to X8 is present or absent, X9 and X11 are present, X10 is L or Q, and said peptide modulates cardiac function in a vertebrate; or a salt, amide or ester thereof.

In a second aspect, the invention provides an isolated peptide comprising the amino acid sequence:
X1-X2-X3-X4-X5-X6-X7-X8-X9-X10-X11-F wherein (SEQ ID NO: 13),
any one of amino acids X1 to X8 is present or absent, X9 and X11 are present, X10 is L or Q; with the provisos that:
when said peptide consists of a pentapeptide, the amino acid sequence of said pentapeptide is not LPLRF (SEQ ID NO: 3); and when
said peptide consists of a dodecapeptide and X6, X7, X8, X9, X10, and X11 are each A,N,L,P,L, and R respectively, X4 is not S or P. In one embodiment of the second aspect, the peptide modulates cardiac function in a vertebrate.

In one embodiment of any of the aspects of the invention described above, where X1 is an amino acid other than M, V, or S; X5 is other than F, or V; X7 is other than N; X9 is other than P, and X11 is other than R; and each of X1, X5, X7, X9, and X11 is independently selected from one another. In another, X11 is an amino acid other than R. In another, at least one of X1, X5, X7, X9, and X11 is A.

In another, X8 is present. In another, X8 is A, V or L; and X9 is P or F. In another, X2 is P, X4 is S; X6, X7, X8 and X9 are each respectively A, N, L, and P.

In another, at least one of X3 and X7 is an amino acid other than histidine. In a related embodiment, the inventive peptide described herein contains no internal histidine residues.

In another, X1 and X2 are absent. In another, where X1 and X2 are absent, X7 is A. In another, where X1 and X2 are absent, and X7 is A, said peptide is a reverse agonist of h-RFRP1.

In another, X3 is Bpa. In a related embodiment, an internal histidine residue of any naturally occurring decameric or dodecameric peptide having a C-terminal sequence consisting of LRFamide described herein, is replaced with Bpa.

In another, the inventive peptide according to any of the aspects of the invention comprises a tyrosyl residue. In another, the tyrosyl residue is an N-terminal tyrosyl residue. In another, the tyrosyl residue is detectably labeled.

In another, the inventive peptide is an h-RFRP1 agonist, antagonist or reverse agonist.

In another, X1 and X2 are absent and X4 is an amino acid other than D. In another, X1 and X2 are absent, and X4 is Bpa.

In a third aspect, the invention provides a pharmaceutical composition comprising a pharmaceutically acceptable carrier and an isolated peptide comprising the amino acid sequence X1-X2-X3-X4-X5-X6-X7-X8-X9-X10-X11-F (SEQ ID NO: 13) wherein, any one of amino acids X1 to X8 is present or absent, X9 and X11 are present, and X10 is L or Q; or a salt, amide, or ester thereof.

In a fourth aspect, the invention provides a pharmaceutical composition comprising a pharmaceutically acceptable carrier and an isolated peptide according to the first or second aspect of the invention, and any embodiments thereof as described above.

In a fifth aspect, the invention provides use of the pharmaceutical compositions described herein in the treatment of a disorder. In one embodiment, the disorder is a cardiac disorder. The invention further provides use of the inventive peptides for increasing or decreasing cardiac function pre-, during, or post-surgery.

In a sixth aspect, the invention provides the use of any of the inventive peptides described herein in the manufacture of a medicament for the treatment of a cardiac disorder.

In a seventh aspect, the invention provides a method of treating a cardiac disorder in a vertebrate, including a mammal, the method comprising administering to said vertebrate a therapeutically effective amount of an inventive peptide described in the first and second aspects of the invention, and any embodiment thereof as described above; or a pharmaceutical composition described above.

In an eighth aspect, the invention provides a method of screening for an agent that modulates cardiac function in a vertebrate, said method comprising:
 a) contacting a first group of one or more myocytes with an isolated peptide comprising a sequence selected from the group consisting of:
    MPHSFANLPLRF (SEQ ID NO: 2); MPPSFANLPLRF (SEQ ID NO: 14); VPNSVANLPLRF (SEQ ID NO: 15); VPHSAANLPLRF (SEQ ID NO: 16); MPPSAANLPLRF (SEQ ID NO: 17); SLKPAANLPLRF (SEQ ID NO: 18), PLRF, PQRF, FLRF, FQRF, APLRF (SEQ ID NO: 19), APQRF (SEQ ID NO: 20), AFLRF (SEQ ID NO: 21), AFQRF (SEQ ID NO: 22), VPLRF (SEQ ID NO: 23), VPQRF (SEQ ID NO: 24), VFLRF (SEQ ID NO: 25), and VFQRF (SEQ ID NO: 26), wherein F is amidated;
 b) contacting the first group set forth in a), or a second group of one or more myocytes with a test agent; and measuring the effect subsequent to the contacting with the test agent; and
 c) determining from the comparison of the measurement in step a) to that of step b) whether the test agent modulates cardiac function in a vertebrate.

In one embodiment, the peptide in step a) is selected from the group consisting of:
    MPHSFANLPLRF (SEQ ID NO: 2); MPPSFANLPLRF (SEQ ID NO: 14); VPNSVANLPLRF (SEQ ID NO: 15); VPHSAANLPLRF (SEQ ID NO: 16); MPPSAANLPLRF (SEQ ID NO: 17); PLRF, PQRF, FLRF, and FQRF,
wherein F is amidated, and said vertebrate is a mammal.

In another, the test agent is a peptide according to the first or second aspect of the invention. In another, the peptide in step a) further comprises an N-terminal tyrosine wherein said tyrosine is measurably labeled.

In a ninth aspect, the invention provides a method of screening for a compound that modulates cardiac function in a vertebrate, said method comprising:
 contacting a group of one or more myocytes with an isolated peptide comprising the amino acid sequence X1-X2-X3-X4-X5-X6-X7-X8-X9-X10-X11-F (SEQ ID NO: 13) wherein,
 any one of amino acids X1 to X8 is present or absent, X9 and X11 are present, and X10 is L or Q; or a salt, amide, or ester thereof, and determining whether said polypeptide modulates cardiac function in said first group due to said contacting.

In another related aspect, the invention provides a method of screening for a compound that modulates cardiac function in a vertebrate, said method comprising:
 contacting cardiac cell or tissue with an isolated peptide comprising the amino acid sequence X1-X2-X3-X4-X5-X6-X7-X8-X9-X10-X11-F (SEQ ID NO: 13) wherein, any one of amino acids X1 to X8 is present or absent, X9 and X11 are present, and X10 is L or Q; or a salt, amide, or ester thereof, and determining whether said polypeptide modulates cardiac function in said first group due to said contacting. As used herein, for the purposes of the invention by "contacting cardiac cell or tissue" is meant that a cell, or a population of cardiac derived cells, including myocytes, are contacted with a peptide under conditions that promote binding and/or one or more positive or negative effect on cardiac contractility. It is recognized that contacting cardiac cell or tissue can be performed in vitro; such as by the in vitro methods described herein; or in vivo, by administration of one or more peptides to a whole animal, including for example, by tail vain injection and other in vivo administration methods described herein.

In a tenth aspect, the invention provides a method of modulating cardiac function in a vertebrate, including a mammal, said method comprising administering to said vertebrate an isolated peptide comprising the amino acid sequence X1-X2-X3-X4-X5-X6-X7-X8-X9-X10-X11-F (SEQ ID NO: 13) wherein,
 any one of amino acids X1 to X8 is present or absent, X9 and X11 are present, and X10 is L or Q; or a salt, amide or ester thereof in an amount effective to modulate cardiac function in said vertebrate.

In one embodiment of ninth or tenth aspect of the invention, the peptide is an inventive peptide according to the first or second aspect of the invention, and any embodiments thereof as described above.

Particular embodiments of the invention are directed to methods or compositions utilizing an inventive peptide described herein and a pharmaceutically acceptable carrier.

As used herein, the term "pharmaceutically acceptable carrier" encompasses any of the standard pharmaceutically acceptable carriers, such as phosphate buffered saline solution, water, emulsions such as oil/water emulsion or a triglyceride emulsion, various types of wetting agents, tablets, coated tablets and capsules. Typically, such carriers contain excipients such as starch, milk, sugar, certain types of clay, gelatin, stearic acid, talc, vegetable fats or oils, gums, glycols, or other known excipients. Such carriers may also include flavor and color additives or other ingredients.

By means of well-known techniques such as titration and by taking into account the observed pharmacokinetic characteristics of the administered peptide in the individual subject, a skilled artisan can determine the appropriate dosages for treatment methods of the present invention.

All patents, patent applications, government publications, government regulations, and literature references cited in this specification are hereby incorporated herein by reference in their entirety. In case of conflict, the present description, including definitions, will control.

Additional features of the disclosure may become apparent to those skilled in the art from a review of the Detailed Description set forth herein, taken in conjunction with the Drawings, Examples, and appended claims.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is not limited only by the Claims attached herein. For the purposes of the invention, it is understood that the term "comprising" is inclusive of the term "consisting of".

EXAMPLES

Example A

Characterization of the hRFRP-1 Cardiac Receptor, which Tests the Hypothesis hRFRP-1 Binds to a G Protein-Coupled Receptor (GPCR) in Cardiac Myocytes hRFRP-1 receptor is characterized by binding a detectable hRFRP-1 agonist or antagonist to rat cardiac myocytes. Detectable analog binding will be competed out against hRFRP-1 to help confirm receptor identity and specificity. Applicant will examine whether [Bpa3]hRFRP-1, which increases cardiac function, binds to the hRFRP-1 receptor. hRFRP-1 receptor expression will be examined by immunolocalization, by using antisera generated against the identified receptor. Receptor expression in response to a cardiac stressor, myocardial infarction (MI) will be characterized. The receptor will also be examined at the nucleotide level, by using well known molecular biological techniques such as Northern- and Southern blots and polymerase chain reaction (PCR), and the like.

A detectable hRFRP-1 analog will be bound to cardiac myocyte membranes to characterize high affinity binding of the peptide to its receptor. A detectable analog may be generated by iodination of the hRFRP-1 agonist, Y-hRFRP-1. (The tyrosyl hRFRP-1 analog also decreases cardiac function similar to the hRFPR-1 peptide suggesting it binds to the same receptor. An I-Y-hRFRP-1 analog will be tested in cardiac myocytes to confirm it is an agonist or antagonist of hRFRP-1 cardiac function prior to using it to "tag" the receptor. The labeled analog is predicted to bind a myocyte protein because Y-hRFRP-1 is a hRFRP-1 agonist. Additionally, a $^{125}$I-Y-hRFRP-1 analog binds expressed rfr-2, a candidate hRFRP-1 cardiac receptor, tightly and specifically (Gouarderes et al. 2007, Neuropharmacology 2: 376-86). An alternative detectable analog is $^3$H-Y-hRFRP-1 analog (Talmont et al. Aug. 12, 2009, Neurochem Int. EPUB ahead of print, PUBMED PMID 19682524]). Specificity of the binding will be tested by competition with hRFRP-1. Also, assays will be used to compete out binding with [Bpa3] hRFRP-1; as an indirect method of determining whether the parent peptide and analog bind the same receptor. Identity of the [Bpa3]hRFRP-1 receptor will be established by probing cardiac myocytes with [Bpa3]hRFRP-1 to characterize the protein it binds.

Membranes are prepared based on established methods. Briefly, isolated cardiac myocytes prepared according to the methods herein described are incubated with a detectable hRFRP-1 analog (0.1 µM) overnight on an orbital shaker, washed to remove free analog, centrifuged and the pellet solubilized under non-denaturing conditions to maintain the integrity of peptide-receptor binding. Photoactivation of a Bpa-containing hRFRP-1 analog is performed after incubation by ultraviolet light (365 nm) for 15 minutes. Samples are separated by non-denaturing 2-dimensional gel electrophoresis (2DGFE) and processed to specifically identify labeled protein(s). A labeled 2DGE "spot" is purified to homogeneity, which is defined by a single protein under several different gel parameters, e.g., change of MW or pI gradient and/or buffer conditions, and/or a single N terminus. Once purified to homogeneity, MW and pI will be determined, and amino acid sequence obtained based on tryptic maps and mass spectrometry. Analog bound to the receptor will not interfere with amino acid sequence analysis of the protein.

The data will be compared to rfr-2 (Accession #AF268898, MW=48 kDa, pI 9.5) to determine whether this protein is the hRFRP-1 receptor. If there is no match, databases will be searched. Additional sequence data can be obtained from amplifying myocyte transcripts using primers designed to the amino acid sequence obtained. If the sequence is novel, the predicted protein will be analyzed to identify structures characteristic of GPCRs. Control studies will include cardiac myocytes incubated with detectable hRFRP-1 in the presence of excess unlabeled analog or hRFRP-1, incubation with free $^{125}$I (or $^3$H), and incubation with no peptide. Further experiments to characterize the hRFRP-1 receptor will include ligand-protein binding studies to delineate SAR, which should be consistent with the alanine scan and N-terminal truncation data.

If radiolabeled-Y-hRFRP-1 is not a hRFRP-1 agonist the unlabeled Y-hRFRP-1, which is already identified to be a hRFRP-1 agonist, can be detected bound to the receptor based on a pI shift in 2DGE. Receptor protein with and without Y-hRFRP-1, bound and unbound, will differ in pI to detect analog binding via a pI shift significant enough to detect.

The Y-hRFRP-1 bound to receptor protein can also be detected by antisera to Y-hRFRP-1.

Non-denaturing conditions will be used to maintain Y-hRFRP-1-receptor binding; however, the binding constant may not be appropriate in which case another means to tag the receptor protein will be employed. An alternative is [Bpa3]hRFRP-1. Once identified by the approach outlined above, the ability of the receptor protein to bind hRFRP-1, [A11]hRFRP-1 (an antagonist), and [Bpa3]hRFRP1 (a stimulatory analog) will be investigated in cardiac myocyte membranes and, eventually, using expressed proteins.

Y-hRFRP-1 is used as an additional independent experiments to identify the receptor(s) that [Bpa3]hRFRP-1 binds.
Expression of a hRFRP-1 Cardiac Receptor.

Polyclonal antisera to the identified receptor are raised in order to probe expression in isolated rat cardiac myocytes and in rat heart tissue. If the receptor protein is identified as rfr-2, rfr-2 antisera are used to probe for receptor expression. Several rfr-2 antisera are commercially available, each generated to a different antigen predicted from the protein sequence. Standard protocols will be used for indirect immunofluorescence to probe rat myocytes and heart tissue sections.

These data are assessed against work completed that demonstrated RFRP-1 is expressed in rat heart. RNA was isolated from rat cardiac ventricular myocytes and a cDNA was generated (SEQ ID NO: 27; amino acid sequence—SEQ ID NO: 28). Sequencing showed that the RFRP-1 transcript is expressed, providing evidence that RFRP-1 is a cardiac signaling molecule. These experiments were also carried out using human cardiac ventricular tissue and as with rat tissue, it was shown that RFRP-1 mRNA is expressed in human heart (SEQ ID NO: 29; amino acid sequence—SEQ ID NO: 30). These data were further supported by immunohistochemical staining carried out on rat cardiac myocytes which established expression of RFamide related peptide.

Protocols for immunofluorescence studies in myocytes and heart sections are briefly as follows. Vertebrate isolated cardiac myocytes will be processed for indirect immunofluorescence based on McCormick and Nichols (1993). Vertebrate hearts will be processed for cryostat sectioning. Fixed cells and sections will be incubated with rabbit polyclonal hRFRP-1 receptor antisera (~1:1000) overnight, followed by washes and incubation with goat anti-rabbit cyanine-based fluorescent secondary antibody (~1:500), with subsequent washes and processing for imaging. These conditions follow a protocol used in McCormick and Nichols (1993). Non-specific binding will be determined by incubating with antigen-absorbed primary antisera, and in the absence of primary antisera with secondary antibody alone. The exact dilutions of primary antisera and secondary antibody will be optimized under experimental conditions; the values given are typical of previous indirect immunofluorescent protocols.

RFamide immunolocalization data in isolated rat cardiac myocytes; control with preabsorbed antisera and with no primary antisera demonstrate the staining is specific to RFamide-containing peptide. e.g., RFRP-1.

In addition, expression of the receptor protein will be investigated in response to myocardial infarction (MI) induced in rat. Induced MI in rat due to left anterior descending (LAD) coronary artery ligation is an established technique offered on a recharge basis at UM CIG. This avenue of analysis is pursued because of the dramatic effect of hRFPR-1 on cardiac function, and to better understand how hRFRP-1 analogs may act to increase cardiac function under cardiac failure. Briefly, a sedated rat is intubated orally and ventilated via a pressure-controlled ventilator with 0.5-1% isoflurane in 100% oxygen at a peak respiratory pressure of 15 cm $H_2O$ and respiratory rate of 60 breaths per minute. Using a dissecting microscope, the heart is exposed via a left thoracotomy and a 7-0 silk suture tied around the proximal portion of the LAD, 1-2 mm from the left atrium. The chest is filled with warm sterile saline to evacuate air and closed in layers using 5-0 silk suture. Controls are rats which undergo the same thoracotomy protocol without LAD ligation. The technique is also offered for mouse. Expression of the hRFRP-1 receptor protein in MI heart will follow the method used to determine expression under physiological conditions (described above).

It is envisioned that a detectable hRFRP-1 analog binds a cardiac myocyte protein to identify the receptor. Based on MW, pI, and amino acid sequence the receptor will be identified; a likely candidate is rfr-2 or a GPCR protein. Human RFRP-1 binds expressed rfr-2 protein, a putative GPCR. Therefore, the hRFRP-1 cardiac receptor may be rfr-2; however, it will be critical to independently establish receptor identity and protein structure. The amino acid sequences predicted from rat and human rfr-2 cDNAs are 432 and 430 residues in length, respectively, and share 86% identity (Hinuma S et al., 2000, Nat Cell Biol 2: 703-708); thus, identifying the rat RFRP receptor is likely to provide significant information into the human receptor.

A detectable hRFRP-1 analog will identify its receptor protein, and [Bpa3]hRFRP-1 will be used to independently identify the receptor protein. Examples of detectable analogs are $^{125}$I-Y-hRFRP-1, [Bpa3]hRFRP-1, $^{3}$H-Y-hRFRP-1; fluorescently labeled hRFRP-1, and biotinylated-hRFRP-1.

Applicant will investigate whether there is a change in receptor expression in response to MI performed in rat and in mice MI models.

Alternative Approaches

Identity of a hRFRP-1 Cardiac Receptor: Low Abundance of hRFRP-1 Cardiac Receptor.

If the receptor is in low abundance, the receptor can be enriched by including an affinity purification step. Applicant's polyclonal hRFRP-1 antisera recognize analog bound to protein, which can be used to enrich for the ligand-receptor protein complex. The analog does not interfere with structural characterization; the analog-bound protein can be released from antisera by a change in buffer pH or salt. Alternatively, biotinylated hRFRP-1 analog can be an affinity ligand identified by avidin to enrich for a receptor protein from membrane preparations. In addition, polyclonal antisera to the 2DGE-isolated spot can be generated for the structural characterization of the high affinity receptor.

Identity of a hRFRP-1 Cardiac Receptor: Multimeric Receptor.

To the Applicant's knowledge, to date, all $RFNH_2$-containing peptide receptors including rfr-2 are single proteins. If the hRFRP-1 cardiac receptor is a multimeric protein, Applicant's approach identifies the subunit which binds hRFRP-1 and generates a molecular tool to identify the entire receptor complex.

Identity of a hRFRP-1 Cardiac Receptor: Non-GPCR Signaling.

Applicant's approach to identify a receptor using an agonist to tag the protein is independent of what type of molecule hRFRP-1 acts through. Evidence to date suggests hRFRP-1 receptor will be a GPCR, $RFNH_2$-containing peptides typically exert their actions through a GPCR. However, two ionotropic receptors were also identified for these peptides. Both are members of the epithelial amiloride-sensitive-Na+ channel and degenerin family of ion channels (see review Lingueglia et al. 2006, Peptides, 27: 1138-52). Invertebrate $FMRFNH_2$-gated Na+ channel (FaNaC) is directly gated by the peptide. There is evidence that mammalian acid-sensing ion channels (ASICs) are not gated, they are modulated by $FMRFNH_2$ and related peptides. A search of myocytes for a FaNaC or ASIC-like transcript or protein would then be conducted if a hRFRP-1 GPCR is not identified using the approaches outlined above.

Identity of a hRFRP-1 Cardiac Receptor: Alternative Analogs.

$^{125}$I-Y-hRFRP-1 is expected to bind to the receptor because Y-hRFRP-1 is a hRFRP-1 agonist. If the iodinated analog does not bind, another detectable analog will be investigated. However, a radiolabeled or chemically detectable analog is not required. An analog that binds but is not chemically, isotopically, or visually detectable can be used to identify the receptor, non-denaturing 2DGE distinguishes between a bound and unbound protein by an isoelectric point (pI) shift<0.01. A low affinity binding constant for hRFRP-1 also is not expected to be a problem because the peptide binds specifically and tightly to expressed rfr-2 protein; however, incorporating Bpa in order to covalently hind the analog to the receptor addresses this issue. 2DGE may identify multiple labeled proteins; controls will be performed (free $^{125}$I, analog competing out with unlabeled hRFRP-1, etc.) to help identify background, thus eliminating or identifying non-specific analog binding. Labeled proteins identified as specific and which are appropriate sizes to be candidate receptors will be characterized.

Identity of a hRFRP-1 Cardiac Receptor: Differentiation from Related Receptors.

Distinguishing a hRFRP-1 receptor from structurally-related proteins will utilize separation of myocyte proteins based on multiple independent parameters. Homogeneity is based on three independent parameters, MW, pI, and N terminus. The structurally-related proteins rfr-2 (MW=48 kDa, pI 9.5) and rfr-1 (MW=60 kDa; pI 9.4) are clearly distinguished from one another with the techniques the Applicant proposes to use [Bonini et al. 2000; Fukusumi et al. 2006].

Identity of a hRFRP-1 Cardiac Receptor.

Applicant envisions that polyclonal antisera generated to the identified receptor, or if the receptor is rfr-2, antisera generated to rfr-2, to bind the hRFRP-1 receptor protein and determine expression. Alternatively, $^3$H-Y-hRFRP-1 binding to myocytes will be used to determine the expression of labeled receptor protein via autoradiography. Applicant will first establish that $^3$H-Y-hRFRP-1 is an agonist or antagonist; Y-hRFRP-1 is an agonist. Controls will include competing out the labeled peptide with excess unlabeled peptide or using free label alone. An alternative is to detect a peptide-receptor protein complex using fluorescently-labeled hRFRP-1 antisera to recognize hRFRP-1 bound to the receptor protein. Controls include labeled antisera in the absence of peptide ligand. Direct fluorescent labeling of hRFRP-1 can be used to detect protein to which the peptide binds; a control will be to compete out fluorescence with unlabeled hRFRP-1.

Example B

Effects of hRFRP-1 on Contractility and Phosphorylation Mediated by Ser/Thr Kinases/Mechanism(s) by which hRFRP-1 Reduces Contractile Function in Myocytes Involving Protein Phosphorylation The effect of hRFRP-1 on sarcomere shortening and relaxation are measured in the absence and presence of bisindolylmaleimide-1 (bis-1, 500 nM), a PKC inhibitor and/or H-89 (1 micromolar), a PKA inhibitor. Controls include measuring the influence of hRFRP-1 on cardiac function in the absence of inhibitor(s) and measuring function under experimental conditions without peptide in the absence and presence of inhibitor(s). Contractility in response to a $RFNH_2$-containing peptide analog, which is neither a hRFRP-1 agonist nor antagonist, is also measured in the presence and absence of inhibitor(s). Taken together, these data will identify a major signaling pathway(s) involved in the influence of hRFRP-1 on relaxation. Applicant will also examine which $Ca^{2+}$-cycling/myofilament proteins are phosphorylated in response to hRFRP-1 applied to isolated rat cardiac myocytes, and extend the work to human tissue.

The influence of the peptide on myocytes will be investigated by measuring $Ca^{2+}$ transients and isometric force generation in peptide-treated myocytes. In one group of studies, the influence of $10^{-7}$-$10^{-9}$ M hRFRP-1 will be measured in Fura-2AM loaded myocytes over 15 min to determine the influence of this peptide on the cellular $Ca^{2+}$ transient following the protocol of Westfall et al. 2005. Other studies will measure isometric force generation in peptide-treated myocytes which are subsequently permeabilized. Force is measured over a range of $Ca^{2+}$ concentrations, and results from this work will determine whether the myofilaments are a direct target for hRFRP-1 signaling and whether the effects on shortening in myocytes under low load translate to comparable decreases in peak tension and myofilament $Ca^{2+}$ sensitivity. The peptide is expected to significantly reduce both peak tension and increase myofilament $Ca^{2+}$ sensitivity based upon our preliminary in vivo studies.

The Effect of Kinase Inhibitors on the Influence of hRFRP-1 on Relaxation.

Adult rat cardiac myocytes are isolated based on established protocols [Westfall et al. 1997, Meth Cell Biol, 52: 307-322; Westfall and Borton 2003)]. Sarcomere shortening and relaxation are measured in myocytes to obtain basal level data with and without hRFRP-1 ($10^{-8}$M hRFRP-1). Next, media containing a PKC inhibitor, bis-1, (500 ηM) (Green et al. 2006 J Mol Cell Cardiol, 41: 350-359) or a PKA inhibitor, H-89 (100 μM) or PKI analog (PKI-(Myr-14-22)-amide; 1 μM) (Xaio B et al. 2006, Biochem J 396: 7-16; Murray A J et al. 2008, Sci Signal 1: re4) or both a PKC and a PKA inhibitor are perfused for 1 minute prior to adding hRFRP-1, no peptide, or a $RFNH_2$-containing peptide analog which is neither an agonist nor an antagonist to determine the influence of an inhibitor on hRFRP-1 activity. In addition, controls include measuring cardiac function under the same conditions without an inhibitor, no peptide, or a peptide analog ($RFNH_2$; structurally similar to hRFRP-1, yet not a hRFRP-1 agonist nor antagonist).

Phospho-Detection by Western Blot Analysis.

In order to identify phosphorylation targets, myocytes are collected, tested to confirm hRFRP-1 activity, and protein expression which correlates to kinase activity is analyzed. Adult rat cardiac myocytes are scraped from coverslips into sample buffer as described [Westfall et al. 2005]. Proteins are separated electrophoretically on 12% SDS-polyacrylamide gels and transblotted onto PVDF membrane. Immunodetection is conducted as previously described [Westfall and Borton 2003; Westfall et al. 2005].

Antibodies include MAB 1691, a monoclonal antibody recognizing troponin I (TnI) isoforms, anti-phospho Ser/Thr PKA substrate antibody (to identify molecular weights of proteins showing changes in phosphorylation at sites sensitive to PKA) anti-phospho-PKCα/βII, anti-phospho-PKCδ, anti-phospho PKC pan, anti-phospho TnI,Ser23/24 and anti-phospho-PLB. Phosphorylation of PLB at Ser16 (PKA-dependent site) and/or Thr 17 (CaMK II dependent site), and TnI at the Ser23/24 site (PKA and PKC dependent) are detected as previously described (Braz et al. 2004 Nat Med 10: 248-54; Westfall et al. 2005).

Kinase Activity and Radiolabeling Studies.

Non-radioactive PKA and PKC activity assays (Assay Designs, Ann Arbor, Mich.) will also be conducted for these studies to determine whether one or both kinases are activated. In the event TnI appears to be a key target, 2-dimensional separation of TnI immunoprecipitated with MAB 1691 will be carried out followed by liquid chromatographic identification to determine the phospho-species involved. This strategy may be necessary if PKC is the key signaling pathway, as PKC phosphorylates 5 residues on TnI (Noland et al. 1989 J Biol Chem 264: 20778-85). If phosphorylation of other potential targets is suspected (e.g. L-type Ca2+ channel, ryanodine receptor, myosin light chain 2, myosin binding protein C, troponin T) $^{32}$P-orthophosphate labeling and incorporation in myocytes would be measured in response to hRFRP-1 with and without H-89 or PKI or bis-1 and initial identification would be made based on protein molecular weight. Anti-phospho antibodies directed to a specific protein (when available) and/or the 2-dimensional separation described above would then be used to further identify the residues phosphorylated in each target protein.

Myocytes collected for detection of phosphorylation are incubated with and without hRFRP-1 ($10^{-10}$M) and calyculin A, an inhibitor of protein phosphatases Types 1 and 2a. Additionally, hRFRP-1 is applied with and without H-89 (100 μM) or, PKI analog (1 μM) PKA inhibitors or a PKC inhibitor, bis-1, (500 ηM). Controls include no peptide and a peptide analog which is neither a hRFRP-1 agonist nor antagonist. Incubation times and concentrations follow those used previously (e.g. Westfall et al. 2005). In the event studies suggest a phosphatase is a potential and important target, studies also will be conducted in the absence of calyculin A.

Sarcomere Shortening.

The effects of hRFRP-1, [A11]hRFRP-1 (an antagonist) and [Bpa3]hRFRP-1 which increases cardiac function are measured. Measurement of sarcomere shortening and relaxation in cardiac myocytes is detected using a video-based IonOptix detection system as otherwise described herein. Signal averaged data are analyzed to determine resting sarcomere length, peak shortening normalized for resting sarcomere length, (% peak height), time to peak shortening (TTP), and time to 25, 50, 75% relaxation ($TTR_{25}$, $TTR_{50}$, $TTR_{75}$, respectively). Studies measuring $Ca^{2+}$ transient using Fura-2AM loaded myocytes will be monitored for 15 min at $10^{-8}$M hRFRP-1, [A11]hRFRP-1, or [Bpa3]hRFRP-1; Bis-I and/or H-89 are predicted to inhibit the change in the $Ca^{2+}$ transient in tandem with the effects on shortening/relaxation. It is expected that signaling will target both $Ca^{2+}$ transients and myofilaments to produce the reduction in peak shortening and slowed relaxation.

Isometric Force Measurements.

The effect of hRFRP-1 and its agonists and antagonists on force development will be measured. Isometric force measurements will be done according to the protocols in the Westfall laboratory (Westfall et al. 1997 Methods Cell Biol, 52: 307-22; Westfall et al. 2005). Isolated rat cardiac myocytes are treated with hRFRP-1, [A11]hRFRP-1, and/or [Bpa3]hRFRP-1 to study the effects of the peptide, receptor blockade, and the analog which increases cardiac function. A range of concentrations are analyzed. An intact myocyte is treated for 15 minutes, after which it is attached to motor and force transducer. Subsequently, phosphatase inhibitor calyculin A is added and the cell is permeabilized. The force will be measured over pCa 9.0 to 4.5; then de-phosphorylated with alkaline phosphatase and repeated force/pCa curve to ensure peak force does not drop below 80% of original peak. A purpose of these studies is to evaluate whether myofilaments are key targets of the effects of hRFRP-1 and hRFRP-1 analogs.

Alternative Ser/Thr Kinases.

The rapid and dramatic response to hRFRP-1 suggests this peptide acts through direct influences on target proteins rather than modulation via transcriptional control. Alternative approaches therefore include investigating the influence of other kinases or molecules known to be involved in cardiac dysfunction on hRFRP-1 activity. Additional kinases could include Rho kinase which influences myofilament calcium sensitivity to prolong relaxation in the failing heart [Vahebi et al. 2005 Circ Re. 96: 740-747; Lin et al. 2007 Cardiovasc Res 75: 51-58]. Other alternatives could include CaMK II and its role in targeting phospholamban, MAPK which targets phosphatase activity and calcineurin activity, as well as the possibility that other protein phosphatases are directly targeted.

Other Signaling Cascades.

While the major signaling pathway is predicted to involve activation of Ser/Thr kinases, it remains possible other signaling cascades also contribute to the functional response in myocytes. Potential signaling cascades could include other kinases, e.g., Rho, CaMK II, and MAPK kinases. Two dimensional electrophoresis and/or polymerase chain reaction more broadly survey molecular changes within the myocytes upon application of hRFRP-1. Protein loading is normalized using proteins from a silver-stained portion of the polyacrylamide gel. [Green et al. 2006 J Mol Cell Cardiol 41: 350-359].

Alternative to Chemical Inhibitor.

Protein kinase inhibitor (PKI) peptide is an endogenous molecule which regulates PKA activity; it is an alternative to H89. PKI analogs are available commercially (Sigma, Torcis Bioscience, and EMB Biosciences). An effect of PKI on hRFRP-1 activity is indirect evidence for a role for PKA, respectively. Investigation of the roles for PKC or PKA or both combines pharmacological and molecular approaches using RNA interference (RNAi) or a nonfunctional PKC (or PKA) mutant to establish the importance of this signaling cascade in the functional response.

Example C

In Vivo Effects on the Heart

It is recognized that reduced contractile function and phosphorylation observed in response to hRFRP-1 in isolated myocytes translates into a similar pattern of reduced contractility and phosphorylation, plus systolic and/or diastolic dysfunction in vivo.

The intravenous delivery of $10^{-8}$M hRFRP-1 via the tail vein of mice led to cardiac failure; and cardiac responses requiring phosphorylation of proteins involved in excitation-contraction coupling was investigated.

hRFRP-1 dose response studies provide an understanding of the range of concentrations that affect cardiac function in vivo. Applicant will investigate the effect of the antagonist, e.g. [A11]hRFRP-1, alone, and its influence on the effects of hRFRP-1 and on [Bpa3]hRFRP-1 in vivo. It will be determined whether reverse agonists, e.g. the analog [Bpa3] hRFRP-1, increase cardiac function and counters the effects of hRFRP-1-induced cardiac failure and the effects of hRFRP-1 and [Bpa3]hRFRP-1 in cardiac stress.

Applicant will monitor target molecules for phosphorylation in vivo in response to hRFRP-1 in mouse heart, and in response to the hRFRP-1 analog that increases cardiac function. The effects of hRFRP-1 alone, and antagonists, e.g. LPLAFamide and [A11]hRFRP-1, in the presence and absence of hRFRP-1, and reverse agonists, e.g. [Bpa$_3$] hRFRP-1 on cardiac function in vivo under cardiac stressors including myocardial infarction, will additionally be explored. Echocardiography will be performed as described herein.

A first set of studies included $10^{-8}$M hRFRP-1 (n=3) and saline (n=3). Based on the results, a power analysis indicates 95% confidence level will be achieved for the data at n=4. $10^{-8}$M analogs will be included in injections; however, concentrations can be varied due to binding conditions or degradation. The effects of the hRFRP-1 analogs and competition between the parent peptide, hRFRP-1, and analogs on cardiac parameters including HR, LVDs, SV, EF %, and CO will be explored. In addition, the effects of hRFRP-1 and analogs on cardiac function in vivo in response to a cardiac stressor myocardial infarction due to left anterior descending (LAD) coronary artery ligation model will be explored.

To identify molecular components of the signaling pathway in vivo, Applicant will analyze cardiac tissue via Western blot and immunohistochemistry, and polymerase chain reaction to determine whether there are any changes in hRFRP-1 receptor expression and in response to a cardiac stressor, MI. Additionally, hearts can be isolated and processed for performing a "back-phosphorylation" assay as described (Michele et al. 2002 Circ Res 91: 255-262). PKC and/or PKA can be utilized to back-phosphorylate.

Alternative Approaches

Some analogs can be more susceptible to degradation when delivered intravenously. The life times of peptides, a measure of degradation, in hemolymph, can be compared by monitoring the presence of a detectable analog(s), including a "tracer" on an analog. Alternative approaches would include incorporating D-amino acids, which are typically less susceptible to degradation than L-amino acids, into the peptide or analog, or by including protease inhibitors with the injectant (a control is protease inhibitor alone).

Experimental Procedures

*Drosophila melanogaster* Heart Rate—

*D. melanogaster* Oregon R wild-type strain flies were maintained on cornmeal molasses media at 24° C. under a 12 hour light/dark cycle. The animals selected for analysis were larvae, prepupae, or adults; both females and males were analyzed and no difference in response was observed. An animal was positioned onto double-stick tape adhered to a microscope stage and heart rate was monitored for 2 minutes before and 10 minutes after saline (control) or peptide was delivered as previously described (Nichols, R. Et al. (1999), Zornik, E. et al. (1999)). A drawn-out micropipette was used to deliver saline or peptide (40 ηl) into the hemolymph (blood) at a site anterior to the brain to avoid tissue damage to the central nervous system and dorsal vessel (aorta and heart). Each animal received only one microinjection of saline or peptide. In some cases, recordings were extended up to 1 hour to establish the return to baseline. Data were averaged from several animals (n≥10) and reported relative to the basal heart rate.

Myocyte Isolation and Measurement of Sarcomere Length Shortening in Single Myocytes—

Adult rat and rabbit ventricular cardiac myocytes were isolated as previously described (Westfall, M. V. Et al. (1997), Westfall, M. V. and Borton, A. R. (2003)). Hearts from Sprague-Dawley rats and New Zealand white rabbits were perfused and enzymatically digested to isolate myocytes; the protocol was approved by The University of Michigan University Committee on Use and Care of Animals (UCUCA) in accordance with university and federal regulatory guidelines. Aliquots of isolated ventricular myocytes were plated on laminin-coated glass coverslips in serum-containing Dulbecco's Modified Eagle Media (Invitrogen, CA, US) supplemented with 5% fetal bovine serum, and 50 U/ml penicillin and 50 μg/ml streptomycin (pen/strep; Sigma-Aldrich, MO, US). Two hours later, media was replaced with serum-free M199 (Invitrogen) supplemented with 1.8 mM Ca$^{2+}$, 10 mM HEPES, 10 mM glutathione, and pen/strep. Rat myocytes were transferred to a stimulation chamber and electrically paced the day after isolation (Zornik, E. Et al. (1999), Westfall, M. V. Et al. (1997)). Media was changed daily for all myocyte preparations.

Sarcomere shortening was detected using a video-based detection system (IonOptix, MA, USA) as described earlier (Westfall, M. V. and Borton, A. R. (2003)). Rat myocytes were paced at 0.2 Hz and rabbit myocytes were paced at 0.5 Hz or 1.0 Hz for these studies. Recordings were made prior to application of each peptide concentration, the protein kinase C (PKC) inhibitor bisindolylmaleimide-1, (bis-1; CalBiochem/EMD, NJ, US), or media only (control, C) and at 1, 3, 5, 10 and 15 minutes after application of peptide, bis-1, or media. Signal averaged data were analyzed to determine resting sarcomere length, shortening amplitude (peak shortening), shortening rate (departure velocity), and re-lengthening rate (return velocity), as previously described (Westfall, M. V. Et al. (1997), Westfall, M. V. and Borton, A. R. (2003)), in 7-20 myocytes from 3-4 rats for each peptide concentration, bis-1, and media.

Peptide Syntheses—

Peptides were synthesized by standard Fmoc protocol. The structures, TDVDHVFLRFamide (DMS) (SEQ ID NO: 1), MPHSFANLPLRFamide (hRFRP-1) (SEQ ID NO: 2), VPHSAANLPLRFamide, (rat RFRP-1; rRFRP-1) (SEQ ID NO: 16); LAEELSSYSRRKGGFSFRFamide (26RFa(8-26)) (SEQ ID NO: 31); and KGGFSFRFamide (26RFa(19-26)) (SEQ ID NO: 32) were confirmed by amino acid analysis and mass spectrometry.

Analysis of Myocyte Protein Phosphorylation in Response to hRFRP-1—

Isolated rabbit cardiac myocytes were loaded with 100 μCi $^{32}$P-orthophosphate for 1 hour at 37° C. in M199 media supplemented with pen/strep. Radioactive media was replaced with unlabeled media containing the phosphatase inhibitor, calyculin A (10 ηM; Sigma-Aldrich) alone or in addition to $10^{-10}$ M hRFRP-1 for 15 minutes at 37° C. The phosphorylation reaction was terminated by briefly rinsing coverslips in ice-cold relaxing solution (RS: 7 mM EDTA, 20 mM imidazole, pH 7.0, 1 mM free Mg$^{2+}$, 14.5 mM creatine phosphate, and 4 mM MgATP with sufficient KCl to yield an ionic strength of 180 mM, pH 7.0), followed by ice-cold RS+0.1% Triton X-100 followed by several rinses in ice-cold RS alone. Cells were collected in sample buffer, and proteins were separated by SDS-PAGE and detected by silver stain as previously described (Westfall, M. V., Lee, A. M., and Robinson, D. A. (2005)). Phosphorylation was quantified using Quantity One software (Bio-Rad Laboratories, CA, USA) after exposure of dried gels to a phosphorimage cassette.

Echocardiography—

Echocardiograms were performed as previously described (Boluyl, M. O. Et al. (2004)) according to the recommendations of the American Society of Echocardiography. All echocardiography was performed by one registered echocardiographer. Female C57BL/6 mice were weighed to accurately calculate the amount of peptide delivered per kilogram body weight (kg bw). Animal use for echocardiography was approved by The University of Michigan UCUCA in accordance with university and federal regulatory guidelines. Physiological saline or peptide was intravenously delivered via tail-vein injections to a total volume of 150 μl to achieve 5 μmols or 500 ηmols hRFRP-1/kg bw. Each animal was used only once for an injectant, either physiological saline or peptide (n=4-5). Briefly, a mouse was placed in an induction chamber and lightly sedated with 4% isoflurane mixed with 100% oxygen, then placed in a supine position on a heated platform with electrocardiogram contact pads (VEVO™ mouse handling platform; VisualSonics, ON, CA), and its nose placed in a cone with 1% isoflurane in 100% oxygen. High-resolution, two-dimensionally guided recordings of amplitude and rate of motion (M-mode) were obtained with a real-time 30-MHz microvisualization scanhead, RMV™ 707B, interfaced to a Vevo 770™ in vivo micro-imaging system (VisualSonics). Heart rate along with left ventricular end-systolic and end-diastolic dimensions were measured from the two-dimensional sector scans obtained from the parasternal long axis and apical four chamber views using the conventions of the American Society of Echocardiography. For each M-mode measurement, at least three consecutive cardiac cycles were sampled. Left ventricular volumes were measured at end systole ($Vol_s$) and end diastole ($Vol_d$) and used to calculate stroke volume ($SV=Vol_d-Vol_s$) and ejection fraction (EF %=endocardial SV/endocardial $Vol_d \times 100$). Cardiac output (CO=endocardial SV×heart rate) was calculated from stroke volume and heart rate.

Statistical Analysis—

All values reported are expressed as mean±standard error of mean (SEM). Data were analyzed using a 1-way analysis of variance (ANOVA) and a Dunnett's Multiple Comparison Test was performed as a post hoc test; statistical significance was established at a p value<0.05. The half maximal effective concentration ($EC_{50}$) values were calculated from best-fit curves using either Microsoft Excel XP or GraphPad Prism 3.0 statistics software (GraphPad, CA, USA).

Example 1

Cardiovascular Effects of DMS (Dromyosuppressin Peptide)

DMS Diminishes *D. melanogaster* Heart Rate.

Figure 1:
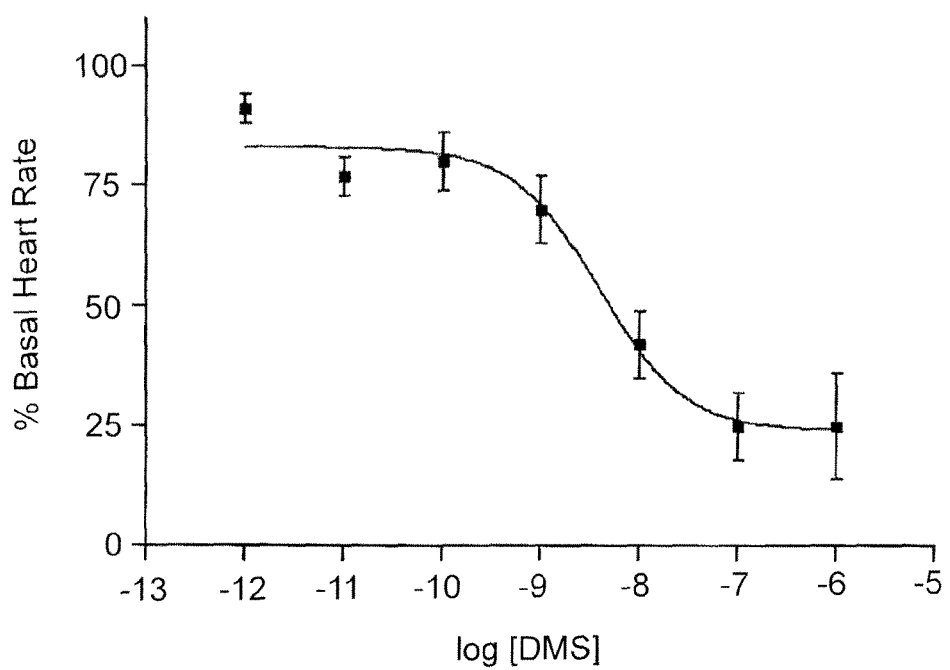
FIG. 1. Dose dependency of a range of DMS concentrations on the frequency of D. melanogaster heart contractions in vivo. Results are the maximal effects observed 1 minute after microinjection compared to basal contraction rate measured prior to microinjection of $10^{-11}$ M, $10^{-10}$ M, $10^{-9}$ M, $10^{-8}$ M, $10^{-7}$ M, or $10^{-6}$ M DMS or control, physiological saline only (n=18). The data point at $10^{-12}$M represents the effect of saline. Data (mean±SEM) were averaged from several animals (n≥10) and reported relative to basal contraction rate measured for each animal. A single animal was used for one microinjection, either peptide or control. The effect of $10^{-10}$ M (n=16) DMS on heart rate was not statistically different from saline; however, $10^{-9}$ M, $10^{-8}$ M, $10^{-7}$ M, or $10^{-6}$ M DMS (n=16; 18; 14; 16, respectively) were statistically significant from control with p<0.05 considered significantly different. The best-fit $EC_{50}$ value was calculated to be $3\times10^{-9}$ M.

The influence of DMS (Dromyosuppressin peptide; TDVDHVFLRFamide—SEQ ID NO: 1) on in vivo heart rate in *D. melanogaster* was compared to physiological saline to evaluate dose-dependent effects of myosuppressin in cardiac function in a model amenable to molecular genetics. *Drosophila melanogaster* myosuppressin dramatically decreased the in vivo frequency of spontaneous pupal heart contractions in a dose-dependent manner (FIG. 1). The dose-dependent effects of dromyosuppressin reported were evaluated in pupae because the animals are immobile and, thus, this developmental stage is the easiest to observe and record heart contractions. The effects of DMS were measured over a range of ten-fold concentrations from $10^{-6}$ M to $10^{-11}$ M and compared to the influence of physiological saline (mean±SEM; 91±3% basal contraction rate at 1 minute; n=18). The maximal effect of subnanomolar $10^{-10}$ M DMS (FIG. 1) was observed within 1 minute and decreased heart rate to 77±4% of the basal contraction rate (n=16), although the reduction in heart rate was not statistically different from the saline control response (p>0.05). Significant reductions in heart rate were detected in response to DMS concentrations of $10^{-9}$ M and higher, and the peak responses were observed within 1 minute of microinjection of the peptide. The DMS-induced effects typically were observed over 2-3 minutes, and were reversible, returning to approximately basal contraction rate levels in about 5 minutes in response to $10^{-8}$ M and $10^{-9}$ M. At the highest concentrations tested, $10^{-6}$ M and $10^{-7}$ M, DMS decreased heart rate to 25±11% (n=14) and 25±7% (n=16), respectively, within 1 minute. The DMS-induced effects were sustained for 3-5 minutes before they returned to approximately basal contraction rate levels within 30 minutes. The best-fit $EC_{50}$ value was $3 \times 10^{-9}$ M.

A similar range of DMS concentrations produced less robust but significant responses on heart contractions in larvae and in adults; the effects of DMS on heart rate were varied in amplitude and were more complex with age (data not shown). The results demonstrate a dose-dependent cardiac response to nanomolar DMS concentrations which suggests this peptide activates a signaling pathway with high affinity.

Further analysis of singly-substituted alanine analogs and N-terminally truncated DMS analogs identified the DMS activity and binding cores, a DMS antagonist, and DMS analogs with the opposite effects of DMS (a reverse agonist). In these analyses, the activity core for the effect of DMS on fly heart was identified as VDHVFLRFamide (SEQ ID NO: 33), in order to achieve an activity similar to the parent DMS peptide; as determined by one or more measures of contractility. In these analyses, the binding core was identified as FLRFamide. The binding core is a DMS antagonist. The alanyl-substituted DMS analogs [A5]DMS (i.e. TDVDAV-FLRFamide—SEQ ID NO: 34) and [A6]DMS (i.e. TDVD-HAFLRFamide—SEQ ID NO: 35) increase heart rate, the opposite effect of DMS, the parent peptide (TDVDHVFL-RFamide—SEQ ID NO: 1). In further experiments in fly, it was determined that the truncated peptides AFLRFamide (SEQ ID NO: 21) or VFLRFamide (SEQ ID NO: 25) are capable of not only binding, but exerting an effect on cardiac contractility. In other words, both truncated peptides are each individually capable of binding and activity when administered to in vivo. In this regard, exertion of one or more effects on contractility is determinable by assessing contractility frequency, contractility amplitude, ejection fraction, and cardiac output.

In order to determine the effect of DMS on cardiac arrest in a larger invertebrate various concentrations of DMS were applied to intact *Protophormia terraenovae*, a blowfly, and electrocardiograms were recorded continuously [Angioy et al. 2007]. At 10 μM, 1 μM, and 0.1 ηM DMS cardiac arrest was observed in 100% of animals (n=10 at each concentration); at lower concentrations cardiac arrest was observed in ~50% of animals. Signal resumed in animals; the recovery time shortened at lower DMS concentrations. Saline did not result in cardiac arrest (n=10).

DMS is Expressed in the Brain and Heart.

Antisera were generated to TDVDHV (SEQ ID NO: 36), the N terminal portion of DMS but did not include the C-terminal RFamide (RF—$NH_2$); a structure present in other $RFNH_2$-containing peptides. Staining with peptide-specific antisera were used to establish DMS spatial and temporal distribution [McCormick and Nichols 1993]. DMS is present in the CNS throughout development. Expression begins late in embryo and continues throughout development to the adult. In general, cells produce DMS in early development and at all stages of life of the animal. Although relatively few cells produce DMS, it is delivered through an extensive arborized network of processes to many targets within the brain. DMS synthesis and release may be under extensive regulatory and sensory input.

DMS-immunoreactive fibers project from the brain to innervate the heart. Applicant's data indicate that the peptide is synthesized in the brain and delivered to the heart. DMS imnmunoreactive processes project from superior protocerebrum neurons in the brain to innervate the anterior region of the dorsal vessel, aorta and heart (right arrow), a region that contains a cardiac pacemaker. The processes are present at all stages of development [McCormick and Nichols 1993]. The presence of DMS throughout development in a region of the *D. melanogaster* heart that contains a pacemaker and DMS activity supports our hypothesis that neural DMS plays an important role(s) in cardiovascular physiology.

DMS Agonists:

Applicant's further SAR analysis for DMS activity on fly heart shows that the amino acids V6, F7, and F10 (referring to the amino acids in the corresponding positions in the parent DMS peptide: TDVDHVFLRFamide (SEQ ID NO: 1) are essential for activity and binding based on analysis of alanyl-substituted and N-terminally truncated analogs. Using these data, Applicant designed Y-[Bpa2]DMS, a detectable DMS analog with a photoactivatable crosslinker p-benzoyl-phenylalanine, Bpa [Shoelson et al. 1993] and tyrosyl, Y, a labeling site (EC50=$1.3×10^{-10}$M; FIG. 8). Applicant used this Bpa-containing analog to identify a DMS receptor [Egerod et al. 2003]; first, it was confirmed the substituted analog was a DMS agonist (see FIG. 8). Data obtained with this Y-analog were used to produce a similar analog for experiments with mammalian myocytes. Y-[Bpa2]DMS refers to the modified peptide: YT(Bpa)VDHVFLRFamide (SEQ ID NO: 37).

That is, with reference to the parent peptide: TDVDHVFLRFamide (SEQ ID NO: 1), the second amino acid (D) is substituted with Bpa, and a tyrosyl residue is added N-terminal of the first amino acid (T).

Example 2

Figure 2:
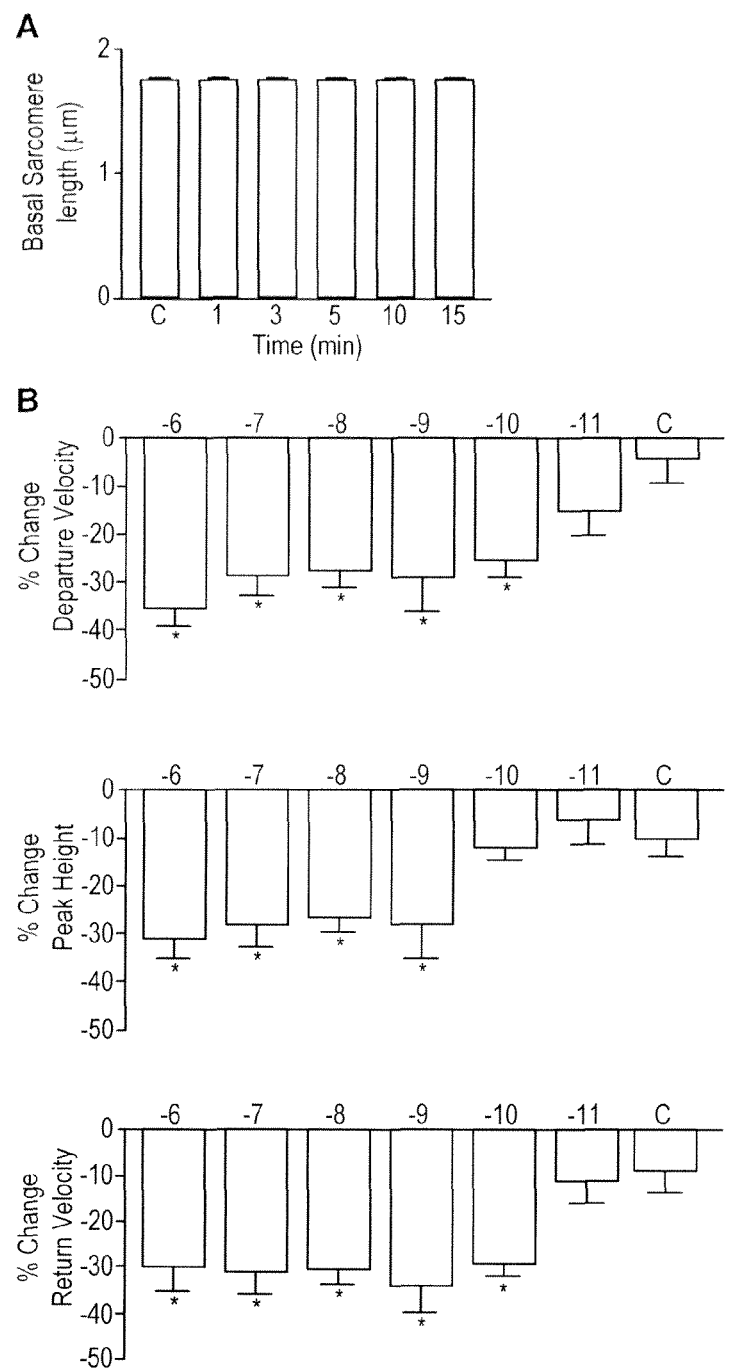
FIG. 2. Adult rat cardiac myocyte contractile function in response to 15 minute perfusion with hRFRP-1, at ten-fold intervals, from $10^{-6}$ M to $10^{-11}$ M at 37° C. and paced at 0.2 Hz. Results are shown for (FIG. 1A; Table 1) baseline sarcomere length (μm) during 15 minutes of perfusion with peptide. The resting sarcomere lengths were 1.76±0.01 μm (C), 1.76±0.01 μm (1 minute), 1.76±0.01 μm (3 minutes), 1.76±0.01 μm (5 minutes), 1.75±0.01 μm (10 minutes), and 1.75±0.01 μm (15 minutes).

Human RFRP-1 Produces Dose-Dependent Effects on Rat Cardiac Myocyte Contractile Function The influence of hRFRP-1 on cardiac function was measured in isolated adult rat cardiac myocytes to test Applicant's hypothesis that this vertebrate FaRP is a myosuppressin-like peptide in mammals. Acute dose-dependent alterations in shortening were measured over 15 minutes in response to $10^{-6}$ M to $10^{-11}$ M hRFRP-1 in isolated adult rat myocytes. Human RFRP-1 peptide dramatically decreased shortening amplitude, and shortening and re-lengthening rates in the isolated cardiac myocytes (FIG. 2B; Table 1). There was no significant effect of $10^{-11}$ M hRFRP-1 compared to control, and resting length remained unchanged at all peptide concentrations. Significant reductions in the shortening and re-lengthening rates were detected in response to concentrations of $10^{-10}$ M hRFRP-1 and higher (FIG. 2B; Table 1). A ten-fold increase, $10^{-9}$ M hRFRP-1, and higher was required to detect significant reductions in shortening amplitude (FIG. 2B; Table 1). The best-fit $EC_{50}$ values were $5×10^{-11}$ M, $5×10^{-11}$ M, and $5×10^{-10}$ M for shortening and re-lengthening rates, and shortening amplitude, respectively. These results demonstrate hRFRP-1 acutely modulates contractile function at the cellular level by directly acting on mammalian cardiac myocytes, and follows a similar dose dependence observed in the *D. melanogaster* chronotropic response to DMS.

TABLE 1

The influence of hRFRP-1 on adult rat cardiac myocyte contractile function over 15 minutes (*denotes statistical significance from control, $p < 0.05$).

| | | | % Change (mean ± SEM) | | |
|---|---|---|---|---|---|
| log [ ] | | baseline | dep v | peak h | ret v |
| hRFRP-1 | n | SL (µm) | (µm/sec) | (µm) | (µm/sec) |
| −6 | 10 | 0.3 ± 0.3 | −35.2 ± 3.8* | −31.2 ± 4.4* | −29.7 ± 5.4* |
| −7 | 18 | −0.3 ± 0.2 | −28.2 ± 4.6* | −27.9 ± 4.9* | −31.0 ± 4.6* |
| −8 | 14 | −0.01 ± 0.2 | −27.7 ± 3.5* | −26.6 ± 2.9* | −30.1 ± 3.2* |
| −9 | 10 | 0.3 ± 0.1 | −29.5 ± 7.9* | −26.8 ± 7.4* | −31.7 ± 6.2* |
| −10 | 7 | −0.06 ± 0.2 | −23.1 ± 4.3* | −9.6 ± 2.7 | −21.8 ± 2.9* |
| −11 | 10 | −0.2 ± 0.2 | −14.7 ± 5.2 | −6.3 ± 4.7 | −11.2 ± 4.5 |
| Control | 20 | −0.1 ± 0.1 | −4.0 ± 4.5 | −10.3 ± 3.4 | −8.7 ± 4.6 |

Example 3

Figure 3:
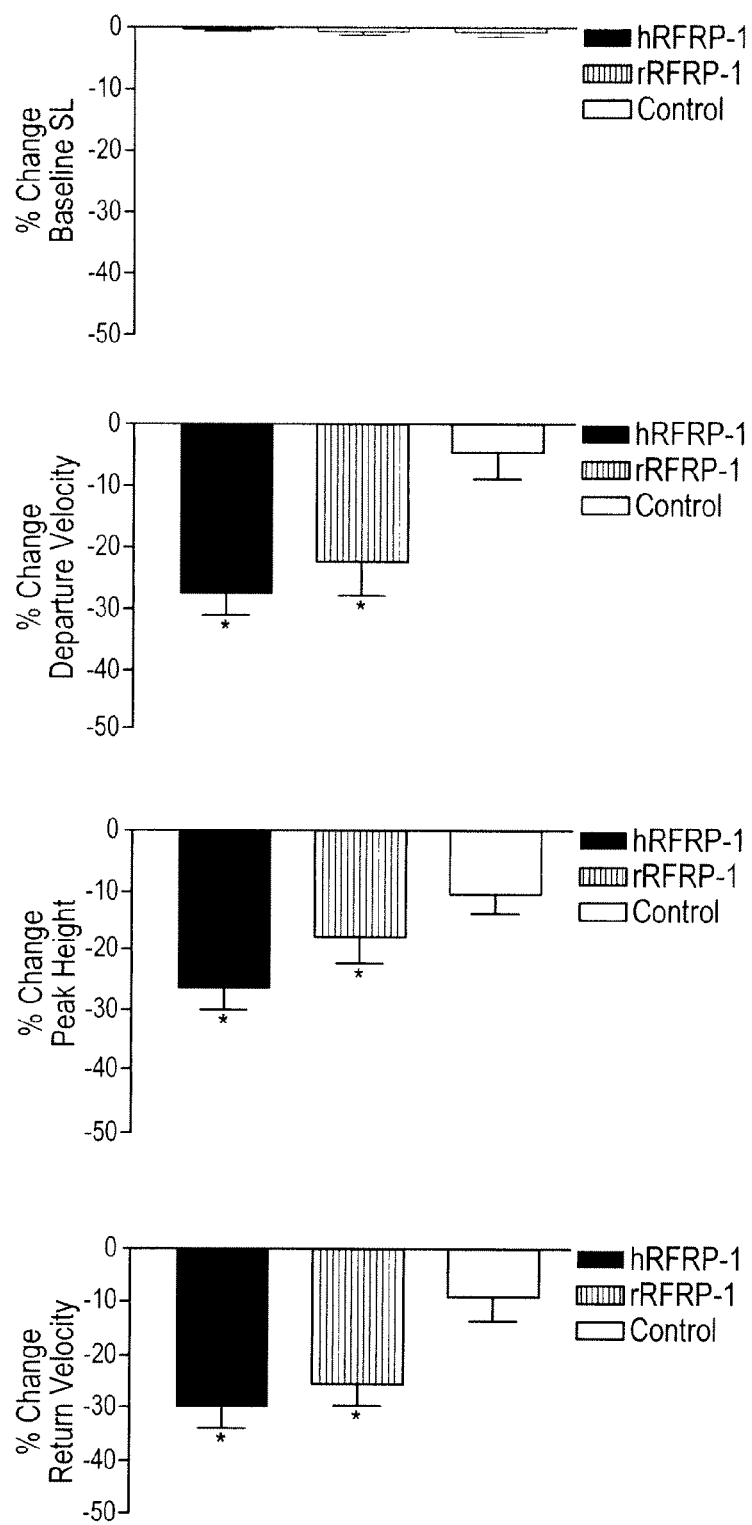
FIG. 3. Percent change in baseline sarcomere length (SL), departure velocity, peak height, and return velocity in response to $10^{-8}$ M rRFRP-1, $10^{-8}$ M hRFRP-1, and control (media, only) in isolated adult rat cardiac myocytes over 15 minutes (Table 3). There were no significant changes in baseline sarcomere length. The influence of $10^{-8}$ M rRFRP-1 and $10^{-8}$ M hRFRP-1 on departure time and in return velocity were comparable and significantly different from control values; however, $10^{-8}$ M rRFRP-1 did not produce the significant decrease in peak shortening observed with $10^{-8}$ M hRFRP-1 and was not significantly different from the media control response. Data were analyzed using 1-way ANOVA followed by a Dunnett's Multiple Comparison Test with $p<0.05$ considered statistically significant (*; Table 3).

Rat RFRP-1 Mimics the Influence of hRFRP-1 on Rat Cardiac Myocyte Contractile Function Rat RFRP-1 (VPHSAANLPLRFamide—SEQ ID NO: 16) differs from hRFRP-1 (MPHSFANLPLRFamide—SEQ ID NO: 2) by two amino acids in the N-terminal amino acid extension; M1→V1 and F5→A5 (Table 2). The influence of $10^{-8}$ M rRFRP-1 was compared to $10^{-8}$ M hRFRP-1 and control (media only) in isolated adult rat cardiac myocytes (FIG. 3; Table 3) to begin an investigation of the structure specificity of RFRP-1 on contractile function. The rat RFRP-1 peptide decreased shortening amplitude, and shortening and re-lengthening rates (−17.7±4.3%, −22.1±6.0%, −25.5±3.9%, respectively; n=12) without significant changes in resting sarcomere length. Thus, similar changes were observed in the shortening and re-lengthening rates with $10^{-8}$ M rRFRP-1 and $10^{-8}$ M hRFRP-1. However, the greater effect of $10^{-8}$ M hRFRP-1 on shortening amplitude compared to $10^{-8}$ M rRFRP-1 and the amino acid differences between the two peptides in the magnitude of hRFRP-1 versus rRFRP-1 effects on shortening amplitude suggest the structure differences of the N-terminal extensions of these two peptides may provide important clues into structure specificity involved in ligand binding and future characterization of a RFRP-1 receptor(s).

TABLE 2

RFamide peptide structures compared; the amino acids and post-translational modification strictly conserved between the RFRP-1 peptides are in bold type (SEQ ID NOs: 14, 2, 16, 39, and 32, respectively).

| Bovine RFRP-1 | | | | | | | | | M | P | P | S | F | A | N | L | P | L | R | F | NH₂ |
|---|---|---|---|---|---|---|---|---|---|---|---|---|---|---|---|---|---|---|---|---|---|
| Human RFRP-1 | | | | | | | | | M | P | H | S | F | A | N | L | P | L | R | F | NH₂ |
| Rat RFRP-1 | | | | | | | | | V | P | H | S | A | A | N | L | P | L | R | F | NH₂ |
| Rat 26RFa (8-26) | L | A | E | E | L | S | S | Y | R | R | R | K | G | G | F | S | F | R | F | NH₂ |
| Rat 26RFa (19-26) | | | | | | | | | | | | K | G | G | F | S | F | R | F | NH₂ |

TABLE 3

The influence of rRFRP-1 on adult rat cardiac myocyte contractile function over 15 minutes (*denotes statistical significance from control, p < 0.05).

| | | % Change (mean ± SEM) | | | |
|---|---|---|---|---|---|
| | n | baseline SL (μm) | dep v (μm/sec) | peak h (μm) | ret v (μm/sec) |
| $10^{-8}$M hRFRP-1 | 14 | −0.01 ± 0.2 | −27.7 ± 3.5* | −26.6 ± 2.9* | −30.1 ± 3.2* |
| $10^{-8}$M rRFRP-1 | 12 | −0.3 ± 0.1 | −22.1 ± 6.0* | −17.7 ± 4.3 | −25.5 ± 3.9* |
| Control | 20 | −0.1 ± 0.1 | −4.0 ± 4.5 | −10.3 ± 3.4 | −8.7 ± 4.6 |

Example 4

Figure 4:
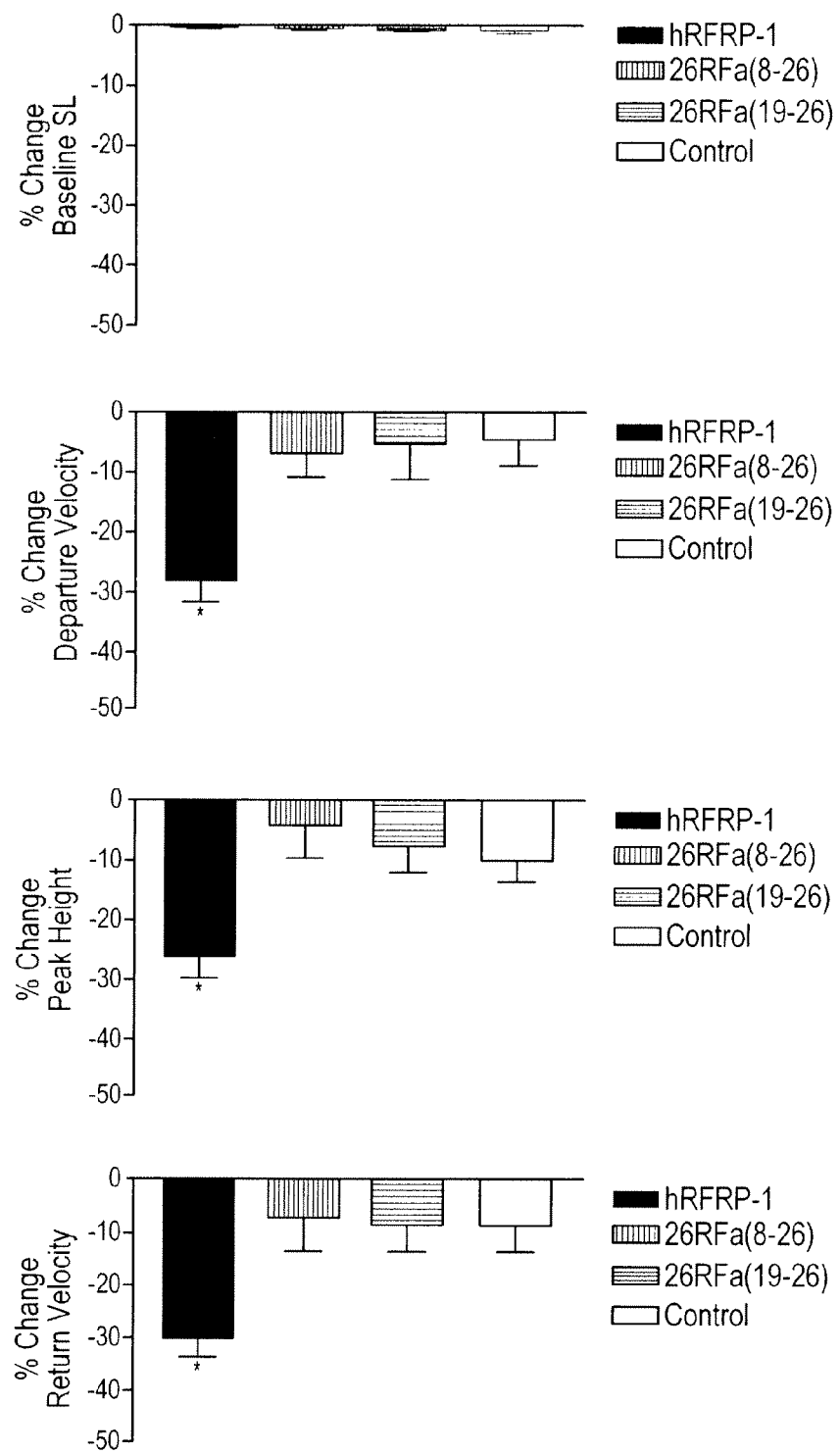
FIG. 4. Percent changes in baseline sarcomere length (SL), departure velocity, peak height, and return velocity in response to 15 minute perfusion with $10^{-8}$ M 26RFa(8-26), $10^{-8}$ M 26RFa(19-26), $10^{-8}$ M hRFRP-1, or control (media only) in isolated adult rat cardiac myocytes (Table 4). There were no significant changes in baseline sarcomere length. There were no significant effects on departure velocity, peak height, and return velocity in response to either $10^{-8}$ M 26RFa(8-26), n=17 or $10^{-8}$ M 26RFa(19-26), n=20. Data were analyzed using 1-way ANOVA followed by a Dunnett's Multiple Comparison Test with $p<0.05$ considered statistically significant (*; Table 4).

The Vertebrate FaRP, 26RFa, does not Mimic RFRP-1 Influence on Rat Cardiac Myocyte Contractile Function The structure specificity of RFRP-1 was further investigated using 26RFa on isolated adult rat cardiac myocytes. Rat 26RFa peptide is a FaRP and, thus, contains an RFamide C terminus identical to RFRP-1; however, there is no similarity in the structure or length of the 26RFa N-terminal extension compared to RFRP-1. The effects of $10^{-8}$ M 26RFa(8-26) (LAEELSSYSRRKGGFSFRFamide—SEQ ID NO: 31) and $10^{-8}$ M 26RFa(19-26) (KGGFSFRFamide—SEQ ID NO: 32) were measured in isolated rat cardiac myocytes (FIG. 4; Table 4). The decreases in shortening amplitude, and shortening and re-lengthening rates in response to $10^{-8}$ M 26RFa(8-26) and $10^{-8}$ M 26RFa(19-26) were modest, and all statistically different from $10^{-8}$ M hRFRP-1 (FIG. 4; Table 4; p<0.05). The responses to the 26RFa peptides were not statistically different from control (FIG. 4; Table 4). These results provide direct evidence that the N-terminal extension present in RFRP-1 is required for its influences on cardiac contractile function. In other words, the strictly conserved C-terminal RFamide, present in all members of the FaRP superfamily including 26RFa peptides, is not sufficient to induce the response produced by RFRP-1 on mammalian cardiac myocyte function. These results demonstrate the 26RFa peptides do not induce a RFRP-1-like response in cardiac myocytes; however, they do not establish whether 26RFa peptides bind to the RFRP-1 receptor.

TABLE 4

The influence of 26RFa peptides on adult rat cardiac myocyte contractile function over 15 minutes (*denotes statistical significance from control, p < 0.05).

| | | % Change (mean ± SEM) | | | |
|---|---|---|---|---|---|
| | n | baseline SL (μm) | dep v (μm/sec) | peak h (μm) | ret v |
| $10^{-8}$M hRFRP-1 | 14 | −0.01 ± 0.2 | −27.7 ± 3.5* | −26.6 ± 2.9* | −30.1 ± 3.2* |
| $10^{-8}$M 26RFa(8-26) | 17 | −0.04 ± 0.1 | −6.0 ± 4.4 | −4.3 ± 5.7 | −7.3 ± 6.3 |
| $10^{-8}$M 26RFa(19-26) | 20 | −0.4 ± 0.2 | −5.3 ± 5.6 | −7.7 ± 4.8 | −8.1 ± 5.0 |
| Control | 20 | −0.1 ± 0.1 | −4.0 ± 4.5 | −10.3 ± 3.4 | −8.7 ± 4.6 |

Example 5

Intravenous Injection of hRFRP-1 Via Mouse Tail Vein Caused Cardiac Dysfunction In Vivo In vivo affect of hRFRP-1 in mouse was investigated. Echocardiography (ECHO) was used to assess the effect of $10^{-8}$M hRFRP-1 (n=3) and control (saline; n=3) on cardiac function via tail vein injection; six C57BL/6 littermates, female, ≈20 grams, and ~4 weeks old. Studies were conducted blind; tail vein injections were done by a registered animal lab technologist. ECHO measurements were done by a registered echocardiologist. Data are percent changes in parameters t=10 minutes post-injection compared to value at t=0 minutes, pre-injection (FIG. 14). The data demonstrate dramatic reduction in heart rate beats per minutes (HR, bpm) in response to $10^{-8}$M hRFRP-1 (100 μl of $10^{-7}$M hRFRP-1 injected). Systole endocardial area (LVDs) showed a dramatic and opposite response, $10^{-8}$M hRFRP-1 (+36%) versus saline (−31%). Also, endocardial stroke volume (SV) differed, $10^{-8}$M hRFRP-1 (−75%) versus saline (+22%). Endocardial ejection fraction (EF %) showed a dramatic response, $10^{-8}$M hRFRP-1 (−60%) versus saline (+25%). An exciting finding is that in response to $10^{-8}$M hRFRP-1 the EF values are indicative of cardiac failure; they fall below 50%. Cardiac output (CO) also showed a dramatic and opposite response, $10^{-8}$M hRFRP-1 (−91%) versus saline (+9%). M mode images illustrate the effects of hRFRP-1; contractility is decreased; 10 minutes post-injection, cardiac function did not recover in marked contrast to post-injection of saline where substantial recovery occurred. Power analysis of these data indicates a 95% confidence level at n=4.

Human RFRP-1 Produces Cardio-Depressant Effects in Mouse.

Figure 5:
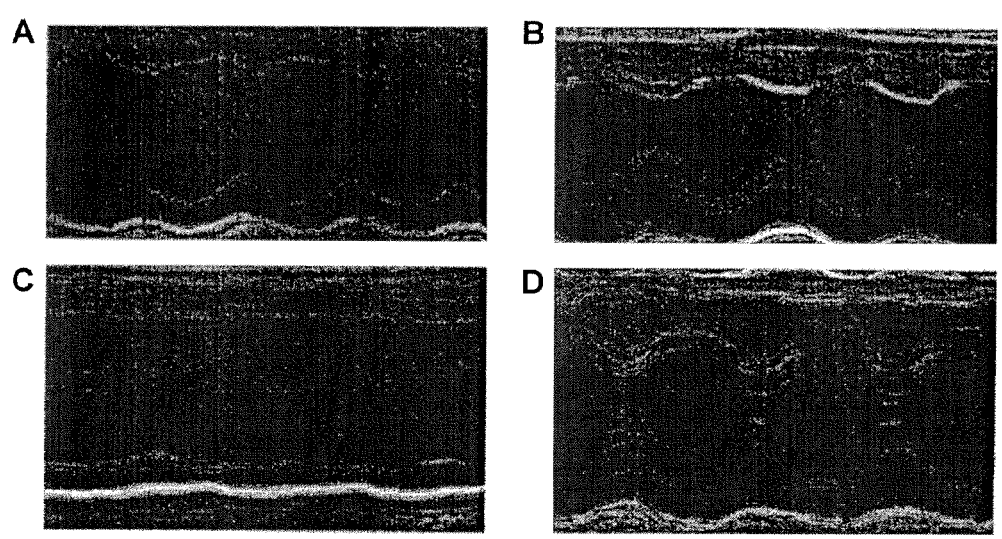
FIG. 5. Representative M-mode images in response to hRFRP-1 and saline on mouse heart. Intravenous administration of hRFRP-1 at 5 µmols/kg bw (n=5) resulted in acute and dramatic effects on heart function (panel A=pre-injection; panel B=5 minutes post-injection). Composite results for echocardiographic studies are shown in Table 5. However, saline (n=4) did not result in dramatic significant changes in cardiac function (panel C=pre-injection; panel D=5 minutes post-injection). Data were analyzed using 1-way ANOVA followed by Dunnett's Multiple Comparison Test with $p<0.05$ considered statistically significant (*; Table 5).

The influence of hRFRP-1 on cardiovascular function in vivo was further studied in determining whether similar cellular and integrated responses are observed in mammals. Cardiac function was measured by echocardiography after peptide or saline (control) delivery via intravenous tail-vein injections in mice. Representative two-dimensional M-mode recordings (FIG. 5) demonstrate the diminished cardiac function in response to 5 μmols/kg bw hRFRP-1 compared to control. At both concentrations (5 μmols and 500 ηmols/kg bw), hRFRP-1 produced a peak effect at 5 minutes post-injection with partial recovery of cardiac function by 15 minutes. The higher dose of hRFRP-1 produced acute and dramatic effects on cardiovascular function (n=5; FIG. 5A pre-injection; FIG. 5B, 5 minutes post-injection; Table 5) compared to the modest variations observed in the saline control group (n=4; FIG. 5C pre-injection; FIG. 5D 5 minutes post-injection; Table 5). Interestingly, the negative chronotropic effect of the lower hRFRP-1 dose (500 ηmols/kg bw) was absent, and although this dose significantly decreased stroke volume, ejection fraction and cardiac output, the relative magnitude was attenuated compared to the higher dose (Table 5). These in vivo data are consistent with a direct dose-dependent effect on myocardium in agreement with the influence of hRFRP-1 observed in isolated rat cardiac myocytes.

TABLE 5

Echocardiographic assessment of mouse cardiovascular function in response to intravenous hRFRP-1 at 5 minutes (*denotes statistical significance from control, $p < 0.05$).

| | % Change (mean ± SEM) | | | |
|---|---|---|---|---|
| | HR | SV | EF % | CO |
| Saline | −17 ± 6% | 17 ± 3% | 32% + 3% | −20 ± 2% |
| 500 ηmol/kg bw hRFRP-1 | −25 ± 2% | −28 ± 10%* | −33% ± 10%* | −44 ± 9%* |
| 5 μmol/kg bw hRFRP-1 | −54 ± 7%* | −57 ± 9%* | −49% ± 8%* | −79 ± 7%* |

Echocardiographic analyses in mice of hRFRP-1, hRFRP-1 and LPLAFamide, LPLAFamide alone, and D-H3-hRFRP-1 via tail-vein injections demonstrated the in vivo effects were consistent with the previous observations when the agents were applied to isolated rat and rabbit cardiac myocytes. Echocardiographic parameters including heart rate (HR), stroke volume (SV), ejection fraction (EF), mitral valve (MV) E and A waves, their amplitudes and ratio (E/A), and cardiac output (CO) were used to make the assessments.

For example, the dramatic decrease on contractile performance shown as a result of application of hRFRP-1 to isolated cells and to whole animals was blocked in vivo by LPLAFamide, a C-terminal hRFRP-1 pentapeptide previously shown to block the effects of hRFRP-1 in isolated cells. LPLAFamide applied alone was shown to have a slight increase in cardiac function in vivo, which may be due to blocking the effects of endogenous hRFRP-1. In addition, D-H3-hRFRP-1, previously shown by the Applicant to be a reverse agonist of hRFRP-1 in isolated rat cardiac myocytes, demonstrated an increase in cardiac function in vivo as measured by echocardiographic parameters.

Example 6

Phosphorylation of Proteins in Response to hRFRP-1 in Isolated Rat Cardiac Myocytes Human RFRP-1 is reported to bind to expressed rfr-2 protein, a putative GPCR; no report describes target molecule phosphorylation in response to hRFRP-1 binding. Protein kinase activation is an important pathway involved in modulating cardiac contractile function. A number of end target proteins involved in excitation-contraction coupling are phosphorylated in response to PKC and/or PKA activation including myofilament proteins cardiac troponin I (cTnI), cardiac troponin T (TnT), and myosin light chain 2 (MLC$_2$). Applicant's data are consistent with phosphorylation of myofilament proteins, e.g., cTnI, TnT, MLC$_2$, in response to $10^{-8}$M hRFRP-1 on rat cardiac myocytes (FIG. 13); following the protocol described in Westfall et al. 2003.

Results showed that PKI, an inhibitor of protein kinase A, (PKA) modifies the activity of hRFRP-1 on isolated ventricular cardiac myocytes.

Human RFRP-1 Effects on Rat Cardiac Myocyte Contractile Function in the Presence of Bis-1, a PKC Inhibitor.

Figure 6:
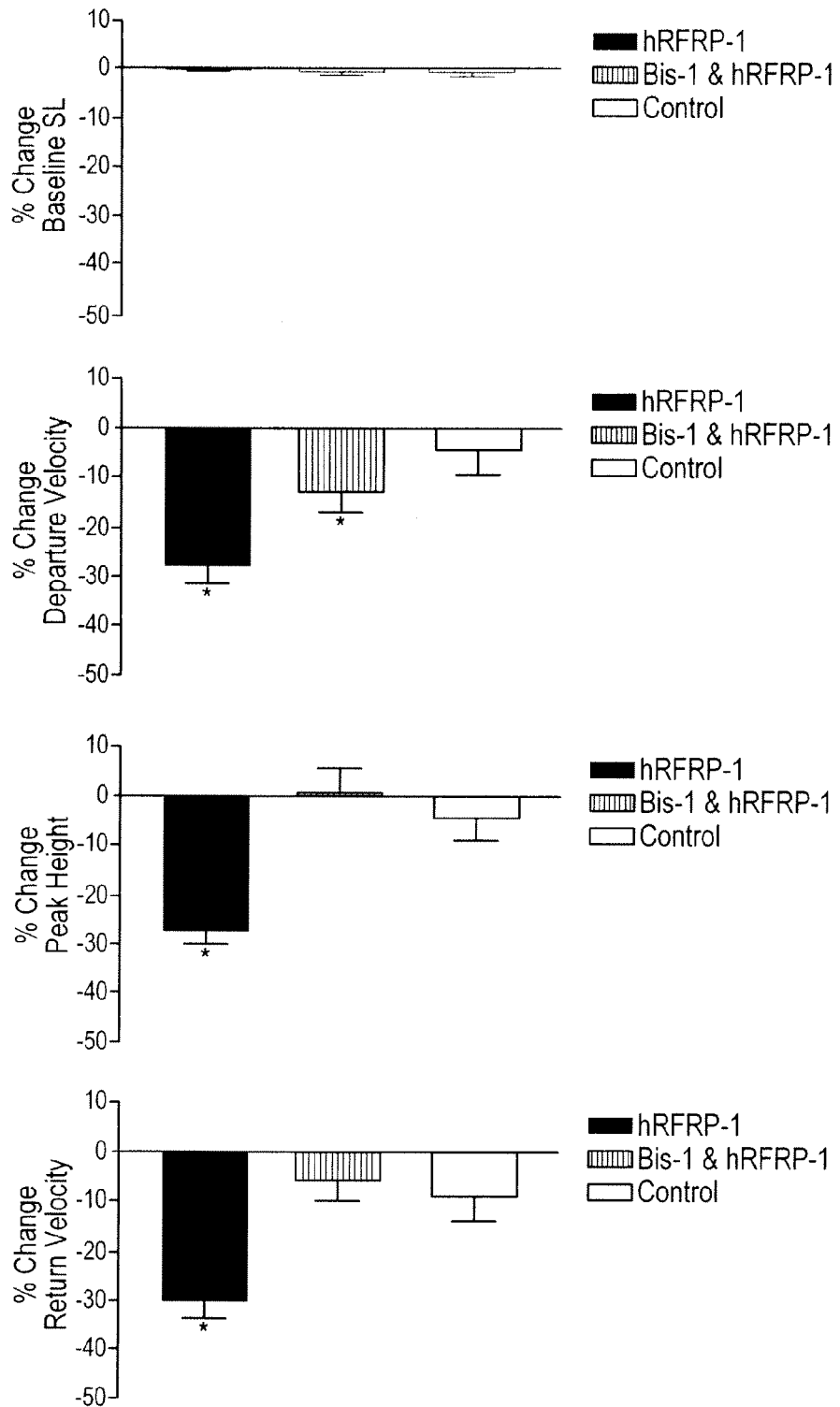
FIG. 6. Adult rat cardiac myocyte contractile function in response to 15 minute perfusion with $10^{-8}$ M hRFRP-1 in the presence of 500 ηM bis-1. Results are shown for (Table 6) baseline sarcomere length (µm) during 15 minutes of perfusion with peptide. The resting sarcomere lengths were 1.76±0.01 µm (C), 1.76±0.01 µm (1 minute), 1.76-0.01 µm (3 minutes), 1.76±0.01 µm (5 minutes), 1.75±0.01 µm (10 minutes), and 1.75±0.01 µm (15 minutes). Table 1 shows percent change in shortening rate, shortening amplitude, and re-lengthening rate during 15 minutes of perfusion with peptide. Values for each concentration (y-axis; hRFRP-1 (log [ ]) were compared to media control (C) with 1-way ANOVA followed by a Dunnett's Multiple Comparison Test with $p<0.05$ considered statistically significant (*; Table 6). The best-fit values for $EC_{50}$ were calculated to be $5\times10^{-11}$ M (shortening rate), $5\times10^{-10}$ M (shortening amplitude), and $5\times10^{-11}$ M (re-lengthening rate). Recordings were made from 7-20, 1-day and 2-day myocytes isolated from n=2-3 hearts.

To initiate studies of the mechanisms involved in the influence of hRFRP-1 on cardiac function, the PKC inhibitor bis-1 was used. The effect of PKC inhibitor bis-1 (500 ηM) on the influence of $10^{-8}$ M hRFRP-1 on shortening and relaxation was measured in isolated adult rat cardiac myocytes over 15 minutes (FIG. 6, Table 6). The PKC inhibitor bis-1 largely blocked the influence of $10^{-8}$ M hRFRP-1 on shortening amplitude, and shortening and re-lengthening rates (−0.58±4.8%, −12.3±4.6%, −5.6±4.7%, respectively; n=23) without significant changes in sarcomere resting length. The effect of bis-1 on hRFRP-1 activity was statistically different from peptide in the absence of the PKC inhibitor. These results provide direct evidence to support the conclusion that RFRP-1 acutely modulates contractile function via activation of the PKC signaling pathway.

TABLE 6

The influence of hRFRP-1 in the presence of Bis-1 on adult rat cardiac myocyte contractile function over 15 minutes (*denotes statistical significance from control, $p < 0.05$).

| | | % Change (mean ± SEM) | | | |
|---|---|---|---|---|---|
| | n | baseline SL (μm) | dep v (μm/sec) | peak h (μm) | ret v |
| $10^{-8}$M hRFRP-1 | 14 | −0.01 ± 0.2 | −27.7 ± 3.5* | −26.6 ± 2.9* | −30.1 ± 3.2* |
| Bis-1; $10^{-8}$M hRFRP-1 | 23 | −0.52 ± 0.2 | −12.3 ± 4.6 | 0.58 ± 4.8 | −5.6 ± 4.7 |
| Control | 20 | −0.1 ± 0.1 | −4.0 ± 4.5 | −10.3 ± 3.4 | −8.7 ± 4.6 |

Example 7

Human RFRP-1 Attenuates Rabbit Cardiac Myocyte Contractile Function

To further evaluate the effects of the conserved RFRP-1 peptide on cardiac function, rabbit cardiac myocytes were utilized. Human RFRP-1 was examined in isolated adult rabbit cardiac myocytes due to their similarity in heart rate compared to humans. Interestingly, sub-nanomolar concentrations of hRFRP-1 significantly reduced mammalian cardiac function. Compared to media only (control), $10^{-10}$ M hRFRP-1 dramatically decreased shortening amplitude and re-lengthening rates in isolated adult rabbit cardiac myocytes (FIGS. 7A and 7B). The shortening rate also decreased in response to $10^{-10}$ M hRFRP-1; however, it was not significant in the myocytes studied. The recordings were made at 0.5 Hz (FIGS. 7A and 7B) and at 1 Hz (results not shown) to assess both shortening and the potential to initiate arrhythmic contractions. Arrhythmic beats and after-contractions were not observed in response to hRFRP-1 at either pacing frequency. In addition, radiolabeling of myocyte proteins increased significantly in response to hRFRP-1 (FIG. 7C). Specifically, a 4.0±1.4-fold increase in phosphorylation was observed above basal value for the band detected at 24 kDa. The phosphorimage illustrates a reproducible increase in phosphorylation of multiple proteins in response to hRFRP-1. The decrease in phosphorylation in response to hRFRP-1 in the presence of bis-1 is consistent with the peptide activating a PKC (data not shown). Together, the functional and phosphorylation results establish that physiologically relevant concentrations of hRFRP-1 dramatically decreased contractile function in both rat and rabbit cardiac myocytes which is consistent with RFRP-1 being a DMS ortholog and suggests hRFRP-1 may play a direct role in modulating mammalian cardiac function. These results suggest RFRP-1 is an endogenous signaling molecule whose effects are mediated by phosphorylation of myocyte proteins by PKC.

In another set of studies, Applicant further observed that at sub-picomolar concentrations hRFRP-1 modulates mammalian cardiac function. $10^{-10}$ M hRFRP-1 was applied to isolated rabbit cardiac myocytes following the method of Westfall et al. 2005; the peptide decreased sarcomere shortening amplitude and slowed relaxation. The effect of $10^{-10}$ M hRFRP-1 (n=20) was statistically different from a control, no peptide, media only (n=12) for peak shortening, return velocity, and time from peak to 50% re-lengthening (TTR50%). Resting length and time to peak (TTP 50%) were not significantly different. p<0.05 (*) was considered significantly different from control (FIG. 17).

Example 8

The Tyrosyl N-Terminal Extended Analog Y-hRFRP-1 is a hRFRP-1 Agonist

Applicant synthesized Y-hRFRP-1 (the peptide: YMPIISFANLPLRFamide—SEQ ID NO: 40) and determined it is a hRFRP-1 agonist in isolated rat cardiac myocytes (FIG. 9A). A tyrosyl-extended analog is an important molecular tool to generate a detectable "tag" for a receptor and investigate its processing, expression, and ligand binding requirements. A tyrosyl group (Y) can be detectable labeled, for example iodinated, tritiated, or biotinylated to generate a detectable agonist; hRFRP-1 does not contain a Y thus avoiding the internal addition of a bulky group which may inhibit peptide-receptor binding.

Example 9

A Structural Analog of hRFRP-1, [Bpa$_3$]hRFRP-1, has the Opposite Effects of hRFRP-1 on Cardiac Function

Discovery of a Reverse Agonist that Increases Cardiac Contractile Function

[Bpa3]hRFRP-1, a structural analog of hRFRP-1 (the modified peptide: MP(Bpa)SFANLPLRFamide—SEQ ID NO: 41), has the opposite effects of hRFRP-1; it increases cardiac function (FIG. 9B). The structure of [Bpa$_3$]hRFRP-1 corresponds to that of the parent peptide MPHSFANLPLRFamide (SEQ ID NO: 2), except that the third amino acid (histidine) is replaced by p-benzoyl-phenylalanine (Bpa). Bpa is a derivative of phenylalanine (Phe; F) and a photoactivatable crosslinker. These data were confirmed from ECHO data images that showed D-H3 hRFRP-1 also increases cardiac function. Further confirmation of D-H3 hRFRP-1 activity was shown by echocardiographic analysis of cardiac parameters when this analog was administered via tail vein injection, after which cardiac function was found to improve.

This discovery is exciting because it suggests mechanisms associated with hRFRP-1, a naturally-occurring peptide, can be targeted to increase cardiac function to counter heart failure. Not only does this discovery identify an analog that increases cardiac function, but the analog can also be covalently crosslinked to its receptor to identify the receptor protein. Thus, the invention encompasses methods of identifying the receptor(s) that hRFRP-1 and [Bpa3]hRFRP-1 bind. The identification of the receptor(s) that hRFRP-1 and [Bpa3]hRFRP-1 bind can be further used to characterize mechanisms associated with decrease and increase in cardiac function, respectively. Bpa-containing hRFRP-1 analogs with Bpa at different positions within hRFRP-1 can be used to produce other valuable agonists and antagonists.

Example 10

An Alanine Scan Identifies Residues Critical for the Effect of hRFRP-1 on Sarcomere Shortening and Relaxation The high degree of RFRP-1 sequence identity across species (Table 7) coupled with its dramatic effects on cardiac function and its presence in brainstem suggests it is physiologically important. The peptides likely contain structure required for binding and for activation of signaling. The structures of these binding and activation cores provide important data to design agonists and antagonists. Applicant analyzed the contribution to activity of the side chain of each amino acid in hRFRP-1 by the systematic single exchange of each residue in the peptide with L-alanine [Beck-Sickinger et al. 1993; Doherty et al. 1993].

TABLE 7

RFRP-1 peptide sequences.

| Human   | M | P | H | S | F | A | N | L | P | L | R | F | NH$_2$ SEQ ID NO: 2  |
|---------|---|---|---|---|---|---|---|---|---|---|---|---|----------------------|
| Bovine  | M | P | P | S | F | A | N | L | P | L | R | F | NH$_2$ SEQ ID NO: 14 |
| Chicken | V | P | N | S | V | A | N | L | P | L | R | F | NH$_2$ SEQ ID NO: 15 |
| Mouse   | V | P | H | S | A | A | N | L | P | L | R | F | NH$_2$ SEQ ID NO: 16 |
| Rat     | V | P | H | S | A | A | N | L | P | L | R | F | NH$_2$ SEQ ID NO: 16 |
| Hamster | V | P | H | S | A | A | N | L | P | L | R | F | NH$_2$ SEQ ID NO: 16 |
| Sheep   | M | P | P | S | A | A | N | L | P | L | R | F | NH$_2$ SEQ ID NO: 17 |
| Frog    | S | L | K | P | A | A | N | L | P | L | R | F | NH$_2$ SEQ ID NO: 18 |

Sequence and structure data are from Dardente et al. 2008 and references within the citation; Ubuka T. et al. (2009) PLoS One 4 (22): e8400; pages 1-7.

An alanine scan was performed to identify residues critical for receptor activation. Applicant synthesized a set of analogs in which each amino acid was replaced, individually except amino acid residue #6, an A, which will be replaced by G. Applicant tested the effect of analogs on isolated rat cardiac myocytes (FIG. 10; n=20). Alanine analogs [A1]hRFRP-1, [A5]hRFRP-1, [A7]hRFRP-1, [A9]hRFRP-1, and [A11]hRFRP-1 were significantly different in peak shortening (peak h) and relaxation (ret v) from the unsubstituted parent peptide, hRFRP-1. Substitution of $R_{11} \rightarrow A$ was dramatically different from hRFRP-1 and similar to control. A truncated analog scan is performed to identify additional hRFRP-1 agonists and antagonists.

The designations [A1]hRFRP-1, [A5]hRFRP-1, [A7]hRFRP-1, [A9]hRFRP-1, and [A11]hRFRP-1 correspond to the parent hRFRP-1 peptide (MPHSFANLPLRFamide—SEQ ID NO: 2), where the first, fifth, $7^{th}$, $9^{th}$, or the $11^{th}$ amino acid is respectively replaced by an alanyl residue (A); and the remaining 11 amino acids in each of the five peptides is the same as the parent peptide. For example, [A1]hRFRP-1 designates the peptide: APHSFANLPLRFamide (SEQ ID NO: 42); and [A7]hRFRP-1 designates the peptide: MPHSFAALPLRFamide (SEQ ID NO: 43); and so forth.

Example 11

The Alanine-Containing Analog [A11]hRFRP-1 is a hRFRP-1 Antagonist

Inactive analogs identified in Applicant's alanine scan may be hRFRP-1 antagonists, which block binding of hRFRP-1, yet do not activate signaling. To identify a functional antagonist Applicant tested hRFRP-1 on isolated myocytes in the presence of an inactive analog. The effects of hRFRP-1 in the presence of [A11]hRFRP-1 was compared to hRFRP-1 alone, and to [A11]hRFRP-1 alone. The effects of $10^{-8}$M hRFRP-1 were dramatically reduced in the presence of $10^{-7}$M [A11]hRFRP-1 compared to $10^{-8}$M hRFRP-1 alone (FIG. 11).

Identification of a hRFRP-1 antagonist in vivo is a powerful molecular tool to attenuate hRFRP-1 function. Furthermore, antagonists are important in delineating ligand-receptor binding and signal pathway activation. Other inactive analogs will be tested to identify additional antagonists. In further experiments, the peptide LPLAFamide was identified as an hRFRP-1 antagonist (FIG. 18). Echocardiographic data showed LPLAFamide blocked the effects of hRFRP-1, and LPLAFamide alone enhances cardiac function.

Example 12

The hRFRP-1 Antagonist, [A11]hRFRP-1, Blocks the Effects of [Bpa3]hRFRP-1

In order to gain insight into the receptor to which [Bpa3]hRFRP-1 binds, Applicant determined its effects in the presence of [A11]hRFRP-1, an inactive alanyl-substituted hRFRP-1 analog, that does not affect cardiac function when administered alone to cardiac myocytes. [A11]hRFRP-1 attenuates the effects of hRFRP-1 (FIG. 1) suggesting it is a hRFRP-1 antagonist. [A11]hRFRP-1 also decreases the effects of [Bpa3]hRFRP-1 (FIG. 12) which can be interpreted to suggest [A11]hRFRP-1 is a [Bpa3]hRFRP-1 antagonist. These data are also consistent with [Bpa3]hRFRP-1 and hRFRP-1 binding to the same receptor.

Example 13

Truncated hRFRP-1 Peptides

The effects of control (media only), hRFRP-1, and truncated hRFRP-1 peptides on departure velocity, peak height and return velocity on isolated adult rat cardiac myocytes were examined (FIG. 15). The tetrapeptide PQRFamide was similarly examined (FIG. 16). The experimental protocol was as described above. All peptides were administered at a concentration of $10^{-8}$M. The following convention is used to indicate each truncation in FIG. 15:

hRFRP-1 describes the peptide: MPHSFANLPLRFamide (SEQ ID NO: 2),

[2-12]hRFRP-1 describes the peptide: PHSFANLPLRFamide (SEQ ID NO: 4).

[3-12]hRFRP-1 describes the peptide: HSFANLPLRFamide (SEQ ID NO: 44),

[4-12]hRFRP-1 describes the peptide: SFANLPLRFamide (SEQ ID NO: 45),

[5-12]hRFRP-1 describes the peptide: FANLPLRFamide (SEQ ID NO: 46),

[6-12]hRFRP-1 describes the peptide: ANLPLRFamide (SEQ ID NO: 47),

[7-12]hRFRP-1 describes the peptide: NLPLRFamide (SEQ ID NO: 48),

[8-12]hRFRP-1 describes the peptide: LPLRFamide (SEQ ID NO: 3),

[9-12]hRFRP-1 describes the peptide: PLRFamide,

[10-12]hRFRP-1 describes the peptide: LRFamide,

In these sets of experiments, the peptides LPLRFamide (SEQ ID NO: 3), FANLPLRFamide (SEQ ID NO: 46), and PQRFamide demonstrated the capability to bind and affect myocyte contractile function when individually administered to myocytes; and, in a manner similar to the parent peptide hRFRP-1.

Any of the truncated peptides described in this EXAMPLE are tested for their ability to modulate cardiac function in vivo (e.g. by mouse tail vain injection as described herein); and/or for their ability to affect the binding or activity of hRFRP-1 on isolated myocytes using experimental protocols similar to these described in EXAMPLES 11 and 12 or expressed receptor protein. Thus, any of the inactive truncated peptides can be readily tested as a candidate hRFRP-1 antagonist in vivo or in vitro.

Peptides influence cardiac dysfunction; however, peptidergic modulation of contractile performance remains relatively uncharacterized. Here Applicant identified a human peptide that modulates mammalian contractile performance. Members of the FMRFamide-related peptide (FaRP) family contain a C-terminal RFamide but structurally variant N-terminal extensions. The EXAMPLES set forth above demonstrate that dromyosuppressin (DMS), an invertebrate FaRP, directly modulated *Drosophila melanogaster* cardiac function in a dose-dependent manner in vivo. The DMS orthologs human RFamide-related peptide-1 (hRFRP-1) and rat RFRP-1 rapidly and reversibly decreased shortening and relaxation in isolated mammalian cardiac myocytes in a dose dependent manner. These functional effects coincided with increased protein phosphorylation of myocyte proteins. The protein kinase C (PKC) inhibitor bisindolylmaleimide-1 blocked hRFRP-1 activity. In addition, intravenous injection of hRFRP-1 in mice produced cardio-depressant effects to decrease heart rate, stroke volume, ejection fraction, and cardiac output. Collectively these discoveries suggest RFRP-1 is an endogenous cardiac signaling molecule that activates PKC. The specificity and structural requirements of RFRP-1 were demonstrated using the mammalian FaRP, 26RFa, related to RFRP-1 by only an RFamide; 26RFa did not alter myocyte contractile function. Taken together, the discovery of these negative chronotropic, inotropic, and lusitropic effects of hRFRP-1 are significant; they show direct acute cellular and organ-level responses in mammalian heart. This discovery is the first identification of a FaRP with dramatic cardio-depressant effects in mammals, and provides a new area in the field of peptidergic modulation of contractile performance.

The EXAMPLES set forth above demonstrate the specific cardiac actions of both invertebrate and mammalian FaRP myosuppressin orthologs. Dose-dependent cardiac effects are found at the organ system level in both invertebrates (FIG. 1) and mammals (FIG. 5) and at the cellular level using two mammalian models and two mammalian orthologs (FIGS. 2-4, 6, 7). These cardiac responses developed over a concentration range that would be expected if a peptide is released as a neuro-hormonal modulator of cardiovascular function. The consistency of the cardio-depressant effects in multiple mammalian models and with the two mammalian orthologs suggests this peptide group serves a functionally conserved role in modulating cardiac performance. Studies with the 26RFa peptides (FIG. 4) demonstrate the conserved RFamide C terminus of the FaRP family is not sufficient to produce this response. Rather, for the activity of the endogenous vertebrate RFRP-1, the N-terminal amino acid extension common to vertebrate RFRP-1 is required. Overall, the results set forth in the above EXAMPLES demonstrate that the myosuppressin peptide family is a novel pathway for modulating cardiac function. Applicant has now discovered the effects of these highly conserved mammalian orthologs on mammalian cardiovascular physiology. The mammalian orthologs include those described in Ubuka et al. 2009, Fukusumi et al. 2001, Hinuma et al. 2000, and Lin et al. 2001.

Members of a FaRP subgroup generally have similar functional activities, but are different from other subgroups within the RFamide superfamily. The present study indicates the actions of the LRFamide subgroup acting as cardiodepressants in both invertebrates (FIG. 1) and mammals (FIGS. 2-4, 6, 7). The conservation of activities indicates LRFamides likely act through a common mechanism within the heart. Recently, another vertebrate FaRP, 26RFa was reported to increase heart rate and blood pressure in rat (Fang et al., 2009). As indicated above, the studies described herein show no significant effects of this FaRP on isolated cardiac myocyte shortening or relaxation (FIG. 5). The structure-specific, high affinity, response to mammalian RFRP-1 is consistent with a novel peptidergic receptor, most likely linked to one or more cellular signaling pathways. In addition, the substantial functional response to nanomolar RFRP-1 (FIGS. 2-4, 7) is consistent with a pathway utilizing a high affinity receptor. The identity of the RFRP-1 cardiac receptor and molecular signaling mechanisms are not yet known. However, other FaRPs may act through G-protein coupled receptors (Liu, Q. Et al. (2001), Fukusumi, S. Et al. (2001), Ukena, K., and Tsutsui, K. (2001)).

The results set forth in the EXAMPLES herein also demonstrate some differences in the functional effects of RFRP on isolated mammalian cardiac myocytes compared to cardiac function in the intact mouse (FIGS. 2-4, 6, 7 versus FIG. 5). The profound decrease in heart rate was not reflected in detected rhythm disturbances in the isolated myocyte. This difference may be due to effects on neural targets present in the in vivo studies. While rhythm disturbances were not detected at pacing frequencies ranging from 0.2-1 Hz in the 0.2, 0.5, and 1 Hz isolated myocyte studies, it remains possible this aspect of the response may not be evident at the lower pacing frequencies used for functional studies in isolated myocytes. The hRFRP-1 induced decrease in systolic function observed in vivo are consistent with the cellular response, an indication that the in vivo effect is due at least in part to a direct suppression of cardiac myocyte contractile function. However, the slowing of relaxation observed in isolated adult myocytes was not detected in vivo. This slowing of in vitro re-lengthening and lack of change in in vivo diastolic performance may reflect variability in the non-invasive assessment of diastolic performance, attenuated detection due to rate-related changes in function (Dias F A et al., J Mol Cell Cardiol 41: 330; 2006) and/or the influence of factors such as load and compensatory responses within a whole animal model.

The present results are also in contrast to earlier work using non-vertebrate orthologs in mammalian models. Avian or invertebrate orthologs (Mues et al, (1982); Barnard, C. S., and Dockray G. J. (1984), Dockray, G. J. et al. (1983)) reportedly produce hypertension, which was not apparent throughout the 15 minute recording (FIG. 5). Invertebrate and avian orthologs may have structural differences leading to multiple actions on mammalian cardiovascular function compared to hRFRP-1, when administered to mammalian models. Alternatively, the divergent responses may be due to protocol differences. Earlier studies used invasive blood pressure measurements in contrast to the non-invasive echocardiography analysis used here. These heterologous, non-endogenous non-vertebrate FaRPs may target different organs and/or cellular pathways when administered to mammalian animal models.

Neurohormones play a critical role in modulating heart function under physiological as well as acute and chronic pathophysiological conditions. Although β-adrenergic signaling has been intensively studied under physiological and pathophysiological conditions, (Fang, Q. Et al. (2009)), other neurally-mediated signaling pathways may play significant roles in the regulation of heart function (Brodde D E (1996); Lymperop A. et al. (2007). Of particular interest are small peptidergic signaling molecules with cardioregulatory properties. The studies described herein identify cardiac specific actions of a known invertebrate peptide, and demonstrate that a novel mammalian ortholog belonging to the same peptide family produces a highly specific and dramatic depressant effect on mammalian cardiac myocytes and on in vivo cardiac performance. The present work describes the substantial and consistent cardiac response to a novel mammalian FaRP, which provides a target for diagnostic and/or therapeutic treatments. Future insight into hRFRP-1 synthesis, release, and signaling is useful for the development of therapeutic strategies to prevent or attenuate cardiac dysfunction.

Example 13

Identification of an RFRP_1 Receptor

NPFFR2 mRNA was isolated from isolated rat cardiac ventricular myocytes and cDNA was generated. The cDNA was sequenced (SEQ ID NO: 49; amino acid sequence— SEQ ID NO: 50) which demonstrated that the NPFFR2 transcript in present in rat heart. NPFFR2 is a receptor to which RFRP-1 binds in vitro binding studies using expressed receptor protein. Data demonstrated and argued for the presence of a RFRP-1 signaling pathway acting through the putative G-protein coupled receptor (GPCR) being present in isolated cardiac myocytes.

NPFFR2 mRNA was also isolated from human cardiac ventricular tissue, from which a cDNA was generated and sequenced (SEQ ID NO: 51; amino acid sequence—SEQ ID NO: 52) to establish the NPFFR2 transcript in present in human heart. These data further demonstrated and argued for the presence of a RFRP-1 signaling pathway acting through the putative GPCR being present in isolated cardiac myocytes.

Example 14

Assessment of Signaling Pathways

Amplification of 26RFa mRNA from isolated rat cardiac ventricular myocytes was unsuccessful, although a 26RFa cDNA (SEQ ID NO: 53; amino acid sequence—SEQ ID NO: 54) was isolated from brain mRNA (a control to demonstrate the PCR primers were capable of amplifying 26RFa transcript in brain but not in myocytes), thus providing additional evidence for RFRP-1 being the naturally-occurring RFamide signaling molecule present in ventricular myocytes.

Amplification of GPR103 (putative 26RFa receptor) mRNA from isolated rat cardiac ventricular myocytes was also unsuccessful, although a GPR103 cDNA from rat brain mRNA (SEQ ID NO: 55; amino acid sequence—SEQ ID NO: 56) (a control to demonstrate the PCR primers were capable of amplifying GPR103 transcript in brain but not in myocytes) was generated thus providing additional evidence for RFRP-1 being the naturally-occurring RFamide signaling molecule present in ventricular myocytes.

Amplification of NPFFR1 (putative NPFF receptor) mRNA from isolated rat cardiac ventricular myocytes was unsuccessful, but NPFFR1 cDNA from brain mRNA was generated (SEQ ID NO: 57; amino acid sequence 58), (a control to demonstrate the PCR primers were capable of amplifying NPFFR1 transcript in brain but not in myocytes) thus providing additional evidence for RFRP-1 being the naturally-occurring RFamide signaling molecule present in ventricular myocytes and signaling through NPFFR2.

Example 15 hRFRP-1 Antisera

Antisera both monoclonal and polyclonal are proven reagents to diagnose and treat disease. Monoclonal antisera (meaning antibodies or antisera) have certain advantages over polyclonal, e.g., mass production is cheaper and specificity is to one peptidergic epitope, although polyclonal antisera, which recognize multiple epitopes, can be advantageous in diagnosis especially if a previously unknown, aberrant structural form of hRFRP-1 exists in a patient, the avidity and detection of the variant form is likely to be higher when using a polyclonal antisera than a monoclonal antibody.

As a diagnostic agent, antisera specific to hRFRP-1 identifies overexpression or under expression of the peptide or identify an aberrant hRFRP-1 structure and, thus, identifies a patient at risk for cardiovascular disease. Accordingly, methods of the disclosure include those comprising the step contacting a test sample with hRFRP-1 antisera and determining expression level of hRFRP-1. Methods wherein expression is over a threshold normal level, as determined in one or more individuals with normal cardiac function, indicates over expression of hRFRP-1. In various aspects, overexpression is indicative of the existence of or potential for cardiac disease in the individual from whom the test sample was derived.

Overexpression of hRFRP-1 (too much of the peptide) may decrease cardiac function below normal, thus antisera to hRFRP-1 would be used in a therapeutic strategy to address the abnormality and return physiological functions to normal. Accordingly, the disclosure provides methods comprising the step of contacting a test sample with hRFRP-1 antisera to determine hRFRP-1 expression, wherein expression over a threshold normal value, determined from an individual with normal cardiac function, indicates the existence of or potential for cardiac abnormality.

Under expression of hRFRP-1 (too little of the peptide) may increase cardiac function above normal, thus a therapeutic strategy would be put in place, e.g., a hRFRP-1 super agonist, to address the abnormality and return physiological functions to normal. Accordingly, the disclosure provides methods comprising the step of contacting a test sample with hRFRP-1 antisera to determine hRFRP-1 expression, wherein expression under a threshold normal value, determined from an individual with normal cardiac function, indicates the existence of or potential for cardiac abnormality.

An aberrant hRFRP-1 structure may increase or decrease cardiac function dependent upon whether the difference in structure leads to a more or less potent variant of the naturally-occurring peptide and, thus, cause an imbalance in normal physiological functions. Antisera to hRFRP-1 would be used in a therapeutic strategy to address the increased or decreased cardiac function and return physiological functions to normal.

As a therapeutic agent, hRFRP-1 antisera may be used to lower the amount of peptide present and, thus, alleviate symptoms related to heart failure or reduced cardiac function. Accordingly, the disclosure provides a method for treating a cardiac condition comprising the step of administering an amount of hRFRP-1 antisera in an amount effective to treat the cardiac condition.

REFERENCES

1. Jessup, M., and Brozena S. (2003) *N. Engl. J. Med.* 348, 2007-2018
2. Mues, G. Et al. (1982) *Life Sci.* 31, 2555-2561
3. Barnard, C. S., and Dockray G. J. (1984) *Regul. Pept.* 8, 209-215
4. Dockray, G. J. Et al. (1983) *Nature* 305, 328-330
5. Price, D. A., and Greenberg, M. J. (1977) *Science* 197, 670-671
6. Fukusumi, S. et al. (2006) *Peptides* 27, 1073-1086
7. Nichols. R. (1992) *J. Mol. Neurosci.* 3, 213-218
8. Nichols, R. (2003) *Annu. Rev. Entomol.* 48, 485-503
9. Robb, S. Et al. (1989) *Biochem. Biophys. Res. Commun.* 160, 850-856
10. Robb, S., and Evans, P. (1994) *J. Exp. Biol.* 197, 437-442
11. Wasielewski, O., and Skonieczna, M. (2008) *J. Comp. Physiol. B* 178, 877-885
12. Stevens, J. S. Et al. (2009) *J. Exp. Biol.* 212, 3961-3976
13. Angioy, A. M. Et al. (2007) *Peptides* 28, 585-593
14. Hinuma, S. Et al. (2000) *Nat. Cell Biol.* 2, 703-708
15. Liu, Q. Et al. (2001) *J. Biol. Chem.* 276, 36961-36969
16. Fukusumi, S. Et al. (2001) *Biochim. Biophys. Acta* 1540, 221-232
17. Ukena, K., and Tsutsui, K. (2001) *Neurosci. Lett.* 300, 153-156
18. Yano, T. Et al. 2003) *Brain Res.* 982, 156-167
19. Nichols, R. Et al. (1999) *J. Neurogenet.* 13, 89-104
20. Zornik, E. Et al. (1999) *Peptides* 20, 45-51
21. Westfall, M. V. Et al. (1997) *Methods Cell Biol.* 52, 307-322
22. Westfall, M. V. and Borton, A. R. (2003) *J. Biol. Chem.* 278, 33694-33700.
23. Westfall, M. V., Lee, A. M., and Robinson, D. A. (2005) *J. Biol. Chem.* 280, 41324-41331
24. Boluyt, M. O. Et al. (2004) *J. Appl. Physiol.* 96, 822-828
25. McCormick, J., and Nichols, R. (1993) *J. Comp. Neurol.* 338, 278-288
26. Holman, G. M. Et al. (1986) *Comp. Biochem. Physiol. C* 85, 219-224
27. Fang, Q. Et al. (2009) *Eur. J. Pharmacol.* 621, 61-66
28. Dias, F. A. L. et al. (2006) *J. Mol. Cell. Cardiol.* 41, 330-339
29. Brodde, O. E. (1996) *Basic Res. Cardiol.* 91, 35-40
30. Lymperopoulos, A. Et al. (2007) *Trends Mol. Med.* 13, 503-511
31. Angioy, A M, et al, 2007, Peptides 28: 585-93.
32. Beck-Sickinger, A G, et al, 1994, Eur J Biochem 3: 947-58
33. Dardente, H, et al, 2008, J Neuroendocrinol 20: 1252-59
34. Doherty, A M, et al, 1993, J Med Chem 36: 2585-94
35. McCormick, J. et al, 1993, J Comp Neurol 338: 278-88
36. Shoelson. S E, et al, 1993, J Biol Chem 268: 4085-91
37. Westfall, M V, 2003, Methods Mol Biol 219: 159-66
38. Westfall, M V, et al, 2003, J Biol Chem 278: 33694-700
39. Westfall, M V, et al, 2005, J Biol Chem 280: 41324-31
40. Fukusumi, S, et al, 2001, Biochim Biophys Acta 1540: 221-232.
41. Ukena, K, et al, 2001, Neurosci Lett 300: 153-156.
42. Yano, T, et al, 2003, Brain Res. 982: 156-167.
43. Nichols R, et al., 2010, Peptides. November; 31(11): 2067-74.

---

The invention claimed is:

1. An isolated peptide comprising the amino acid sequence of SEQ ID NO: 2 having
   (i) one or more amino acid substitutions at amino acid positions 1-11 of SEQ ID NO: 2 and/or
   (ii) an N-terminal truncation of no more than eight amino acids of SEQ ID NO: 2,
   wherein said peptide comprises an amino acid at position 9 of SEQ ID NO: 2 that is P or a modified version thereof; an amino acid at position 10 of SEQ ID NO: 2 that is L or Q or a modified version thereof;
   wherein the amino acid at position 5 of SEQ ID NO: 2, when present, is F or a modified version thereof; the amino acid at position 7 of SEQ ID NO: 2, when present, is N or a modified version thereof; wherein the amino acid at position 11 is not R;
   wherein said peptide comprises a modified amino acid at one or more amino acid positions 1-11 of SEQ ID NO: 2, said modified amino acid being a D-amino acid, or a chemical compound used as an alternative to an amino acid in synthesis of peptidomimetic compounds, an amino acid derivative, a synthetic amino acid, or a non-native amino acid,
   and said peptide modulates cardiac function in a vertebrate; or a salt, amide or ester thereof.

2. The peptide of claim 1 wherein the amino acid at position 3 of SEQ ID NO: 2, when present, is K, P, N, Bpa, or H or a modified version thereof;
   the amino acid at position 4 of SEQ ID NO: 2, when present, is P or S or a modified version thereof;
   the amino acid at position 6 of SEQ ID NO: 2, when present, is A or a modified version thereof;
   the amino acid at position 8 of SEQ ID NO: 2, when present, is V, L, or A or a modified version thereof; and/or
   the amino acid at position 11 of SEQ ID NO: 2 is A, or a modified version thereof.

3. The peptide of claim 1, wherein the amino acid at position 11 of SEQ ID NO: 2 is A, V or L or a modified version thereof.

4. The peptide of claim 1 wherein the peptide comprises an N-terminal truncation of two amino acids.

5. The peptide of claim 1, wherein the amino acid at position 3 of SEQ ID NO: 2, when present, is Bpa.

6. A pharmaceutical composition comprising a pharmaceutically acceptable carrier and an isolated peptide according to claim 1.

7. A method of screening for a compound that modulates cardiac function in a vertebrate, said method comprising:
   contacting a group of one or more myocytes with an isolated peptide of claim 1, and measuring an effect indicative of cardiac function in said group due to said contacting.

8. The peptide of claim 1, comprising the amino acid sequence PLXF, PQXF, APLXF (SEQ ID NO: 5), APQXF (SEQ ID NO: 6), VPLXF (SEQ ID NO: 9), or VPQXF (SEQ ID NO: 10) at the C-terminus of the peptide, wherein X is any natural or modified amino acid other than L-arginine.

* * * * *

UNITED STATES PATENT AND TRADEMARK OFFICE
CERTIFICATE OF CORRECTION

PATENT NO. : 9,527,889 B2  
APPLICATION NO. : 14/582553  
DATED : December 27, 2016  
INVENTOR(S) : Ruthann Nichols et al.

Page 1 of 1

It is certified that error appears in the above-identified patent and that said Letters Patent is hereby corrected as shown below:

In the Specification

Column 1, Lines 22-24, please delete:

"This invention was made with government support under R21HL093627 awarded by the National Institute of Health (NIH). The government has certain rights in this invention."

and insert:

--This invention was made with government support under grants HL093627 and HL067254 awarded by the National Institutes of Health. The government has certain rights in the invention.--

Signed and Sealed this  
Twenty-eighth Day of February, 2017

Michelle K. Lee  
*Director of the United States Patent and Trademark Office*